United States Patent
Li et al.

(10) Patent No.: US 12,410,136 B2
(45) Date of Patent: Sep. 9, 2025

(54) PYRIDINYL MORPHOLINE COMPOUND, PREPARATION METHOD THEREFOR, AND APPLICATION THEREOF

(71) Applicants: SHANGHAI ZHONGZE THERAPEUTICS, CO. LTD., Shanghai (CN); SHANGHAI INSTITUTE OF PHARMACEUTICAL INDUSTRY, Shanghai (CN)

(72) Inventors: Jianqi Li, Shanghai (CN); Yangli Qi, Shanghai (CN); Xiaowen Chen, Shanghai (CN); Junwei Xu, Shanghai (CN); Ruixiang Yuan, Shanghai (CN); Qiang Pu, Shanghai (CN)

(73) Assignees: SHANGHAI ZHONGZE THERAPEUTICS, CO. LTD., Shanghai (CN); SHANGHAI INSTITUTE OF PHARMACEUTICAL INDUSTRY, Shanghai (CN)

( * ) Notice: Subject to any disclaimer, the term of this patent is extended or adjusted under 35 U.S.C. 154(b) by 516 days.

(21) Appl. No.: 18/007,840

(22) PCT Filed: May 28, 2021

(86) PCT No.: PCT/CN2021/096683
§ 371 (c)(1),
(2) Date: Dec. 2, 2022

(87) PCT Pub. No.: WO2021/244416
PCT Pub. Date: Dec. 9, 2021

(65) Prior Publication Data
US 2023/0242486 A1    Aug. 3, 2023

(30) Foreign Application Priority Data
Jun. 5, 2020 (CN) .......................... 202010506972.3

(51) Int. Cl.
| | | |
|---|---|---|
| C07D 213/74 | (2006.01) |
| C07D 213/87 | (2006.01) |
| C07D 401/04 | (2006.01) |
| C07D 405/04 | (2006.01) |
| C07D 405/12 | (2006.01) |
| C07D 405/14 | (2006.01) |
| C07D 409/04 | (2006.01) |
| C07D 409/14 | (2006.01) |

(52) U.S. Cl.
CPC ......... *C07D 213/74* (2013.01); *C07D 213/87* (2013.01); *C07D 401/04* (2013.01); *C07D 405/04* (2013.01); *C07D 405/12* (2013.01); *C07D 405/14* (2013.01); *C07D 409/04* (2013.01); *C07D 409/14* (2013.01)

(58) Field of Classification Search
None
See application file for complete search history.

(56) References Cited

U.S. PATENT DOCUMENTS

| | | |
|---|---|---|
| 5,047,406 A | 9/1991 | Caprathe et al. |
| 8,802,678 B2 | 8/2014 | Capet et al. |
| 9,388,148 B2 | 7/2016 | Haupt et al. |

(Continued)

FOREIGN PATENT DOCUMENTS

| | | |
|---|---|---|
| CN | 101511805 A | 8/2009 |
| CN | 105339357 A | 2/2016 |
| CN | 106255688 A | 12/2016 |

(Continued)

OTHER PUBLICATIONS

Zimnisky et al., Cariprazine, a dopamine D(3)-receptor-preferring partial agonist, blocks phencyclidine-induced impairments of working memory, attention set-shifting, and recognition memory in the mouse. Psychopharmacology (Berl). Mar. 2013;226(1):91-100 (Year: 2013).*

(Continued)

*Primary Examiner* — Jeffrey S Lundgren
*Assistant Examiner* — Anthony Joseph Seitz
(74) *Attorney, Agent, or Firm* — Nath, Goldberg & Meyer; Joshua B. Goldberg

(57) ABSTRACT

Disclosed in the present invention are a pyridinyl morpholine compound, a preparation method therefor, and an application thereof. The present invention provides a pyridinyl morpholine compound as represented by formula I, a pharmaceutically acceptable salt thereof or a hydrate of the pharmaceutically acceptable salt thereof. The compound can be used as an antagonist for one or more of $D_2$, $D_3$ or $5\text{-HT}_{2A}$, and is used for preparing a drug for treating schizophrenia.

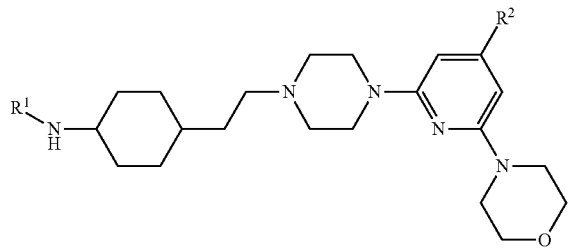

I

18 Claims, No Drawings

(56) References Cited

U.S. PATENT DOCUMENTS 9,840,501 B2 * 12/2017 Galley .................... A61P 25/18
2010/0075979 A1 3/2010 Gobbi et al.

FOREIGN PATENT DOCUMENTS

| CN | 107793350 A | 3/2018 |
| CN | 107793408 A | 3/2018 |
| WO | 2010034648 A1 | 4/2010 |
| WO | 2010070370 A1 | 6/2010 |
| WO | 2011073705 A1 | 6/2011 |

OTHER PUBLICATIONS

Sep. 1, 2021 International Search Report issued in International Patent Application No. PCT/CN2021/096683.
Sep. 1, 2021 Written Opinion of the International Searching Authority issued in International Patent Application No. PCT/CN2021/096683.
Dec. 2, 2022 Chinese First search report issued in Chinese Patent Application No. 22020105069723.
Dec. 2, 2022 Chinese First Office Action issued in Chinese Patent Application No. 2020105069723.
Berge et al., "Pharmaceutical Salts", Journal of Pharmaceutical Science 66: 1-19 (1977).
Journal of Pharmacology and Experimental Therapeutics 2010, 333(1): 328.
Dmitry I. Bugaenko, Quaternary N-(2-Pyridyl)-DABCO Salts: One-Pot in Situ Formation from Pyridine-N-oxides and Reactions with Nucleophiles: A Mild and Selective Route to Substituted N-(2-Pyridyl)-N'-ethylpiperazines, Journal of Organic Chemistry (Jan. 20, 2017)vol. 82, Issue 4, pp. 2136-2149.

\* cited by examiner

PYRIDINYL MORPHOLINE COMPOUND, PREPARATION METHOD THEREFOR, AND APPLICATION THEREOF

This is a National Phase Application filed under 35 U.S.C. 371 as a national stage of PCT/CN2021/096683, filed May 28, 2021, an application claiming the benefit of Chinese Application No. 202010506972.3, filed Jun. 5, 2020, the content of each of which is hereby incorporated by reference in its entirety.

TECHNICAL FIELD

The present disclosure relates to a pyridinyl morpholine compound, a preparation method therefor and a use thereof.

BACKGROUND

Schizophrenia is the most harmful one of mental diseases and is known as the "cancer" in mental diseases. The clinical manifestation of schizophrenia is three major symptoms: positive symptom, negative symptom and cognitive impairment. Positive symptom includes delusion, hallucination, etc.; negative symptom includes apathy, paramania, social withdrawal, bizarre behavior, catatonic excitement, etc.; cognitive impairment includes working and learning memory loss, etc. Modern medicine considers schizophrenia to be a collection of symptoms and signs of unknown etiology. With the deterioration of social environment and the increase of life pressure, the incidence of schizophrenia is increasing year by year.

In recent years, the research on neurotransmitters and receptors related to schizophrenia has been more active, and it has been found that in some patients with schizophrenia, the neuroendocrine is affected due to abnormal function of central neurotransmitters and receptors, and the above research results are used for clinical and the development of new therapeutic drugs. A large number of studies have shown that the mental disease is associated with abnormal function of central monoamine neurotransmitter and receptor, while the central dopamine (DA)-ergic system and 5-hydroxytryptamine (5-HT)-ergic system are closely related to human mental activities. Studies have shown that dysfunction of the DA and 5-HT-ergic systems can easily lead to schizophrenia.

At present, commercially available antipsychotic drugs mainly act on DA and 5-HT-ergic systems, and are divided into classical antipsychotic drugs and non-classical antipsychotic drugs according to their mechanism of action and the number of targets, the former mainly acting on the DA-ergic system ($D_2$ receptor antagonists), the latter acting on the DA and 5-HT-ergic systems (such as $D_2$/$5-HT_{2A}$ receptor dual antagonists). At present, the main first-line clinical drugs are non-classical antipsychotic drugs, and classical antipsychotic drugs lead to extrapyramidal effects (EPS) and hyperprolactinemia due to the excessive antagonism with substantia nigra-striatum and nodule-funnel $D_2$ receptors. In addition, because classical antipsychotic drugs act solely on the DA-ergic system, they are only effective for positive symptoms of schizophrenia, and ineffective against negative symptom and cognitive impairment. Non-classical antipsychotic drugs such as clozapine, ziprasidone, risperidone, aripiprazole, brexpiprazole, cariprazine, etc., can treat both positive and negative symptoms, but there is no significant improvement in cognitive function, and all have corresponding side effects, such as obesity, akathisia, sedation, insomnia, anxiety, type II diabetes mellitus, etc. Therefore, there is currently no marketed drug that can effectively reduce the above side effects while improving the overall spectrum of schizophrenia. It is an important direction for the research and development of antischizophrenic drugs to find new antischizophrenic drugs with high efficiency, low toxicity and wide therapeutic spectrum.

DA receptors include five subtypes, $D_1$, $D_2$, $D_3$, $D_4$ and $D_5$, and belong to two families, namely $D_1$ family ($D_1$ and $D_5$) and $D_2$ family ($D_2$, $D_3$, $D_4$). At present, the more studied are $D_2$ receptor family 1011. $D_2$ receptors are mainly distributed in the center of the substantia nigra, striatum, caudate nucleus, accumbens nucleus and limbic system. The existing antischizophrenic drugs all play the role on antischizophrenia positive symptom by antagonizing $D_2$ receptor. $D_3$ receptor is highly homologous to $D_2$ receptor, and $D_3$ receptor in the brain is mainly distributed in the mesopallium and limbic system, blocking $D_3$ receptor, and can improve learning and memory and improve cognitive function. Therefore, selective antagonism of $D_3$ receptor has a good application prospect as an antischizophrenic drug. However, compared with the $D_2$ receptor, the $D_3$ receptor mRNA is less distributed in the brain, so it is required that the drug should have $D_3$ receptor selectivity while acting on the $D_2$ and $D_3$ receptors, that is, the affinity for $D_3$ is 10 times stronger than the $D_2$ receptor affinity or more, in order to exert physiological effects such as cognitive improvement. A large number of studies have shown that $5-HT_{2A}$ receptor antagonist can relieve the inhibition of excitation ignition of DA-ergic neurons in the limbic system, restore the function of DA-ergic neurons, and thus improve negative symptom. Meanwhile, the antagonism of the $5-HT_{2A}$ receptor can effectively reduce the EPS side effects due to the $D_2$ overblocking. Therefore, new antischizophrenic drugs that simultaneously act on $D_2$, $D_3$ and $5-HT_{2A}$ receptors and have $D_3$ receptor subtype selectivity have become a new direction for the development of antischizophrenic drugs, and provide a new direction for the development of related drugs.

Studies have found that the side effects of first-line antischizophrenic drugs such as sedation and obesity are mainly related to their strong histamine $H_1$ receptor binding effect. Commercially available antischizophrenic drugs (clozapine, risperidone, aripiprazole) and the newly marketed cariprazine have strong or moderate-intensity sedative side effect, which are mainly related to their high $H_1$ receptor affinity, such as clozapine (1.2 nM, Ki), risperidone (15 nM, Ki), aripiprazole (29.7 nM, Ki), cariprazine (23 nM, Ki). Antischizophrenic drugs are long-term medications, and the patient's long-term sedation will seriously affect their normal work, learning, interpersonal communication and other social activities, making it difficult for patients to return to society; in evaluating preclinical efficacy stage, strong sedative effect will interfere with the objective evaluation of the animal cognitive function behavior results.

Therefore, the ideal new antischizophrenic drugs not only have strong affinity for $D_2$, $D_3$, and $5-HT_{2A}$ receptors, reasonable selectivity for $D_3$/$D_2$ receptor, but also have weak or no affinity for $H_1$ receptor, which is a key technical and important scientific problem in the research and development field of this new drug.

WO2010034648A1 discloses a series of selective dopamine $D_3$ receptor modulator compound as shown in structural general formula I having the activity of treating cognitive deficits. The compound structure contains fragments of pyridine piperazine cyclohexylamino as described below.

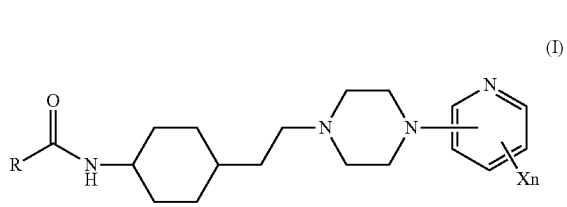

wherein, X independently represents halogen, $C_{1-6}$ alkyl, $C_{1-6}$ haloalkyl or alkoxy;

n is 1 or 2;

R is $C_{1-6}$ alkyl or alkoxy, wherein Ci-6 alkyl can be substituted by —$CONH_2$ or 3- to 6-membered cycloalkyl.

The compound in this patent has an affinity for the $D_3$ receptor between 1.7 to 17.0 ($K_i$ value).

Chinese patent CN1829703B discloses (thio)aminoformylcyclohexane derivatives as $D_2/D_3$ receptor antagonists, and discloses cariprazine

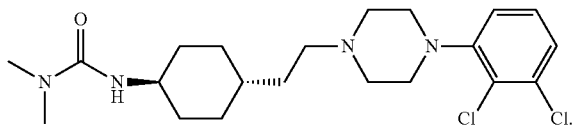 [SMILES: CN(C)C(=O)N[C@H]1CC[C@H](CCN2CCN(c3cccc(Cl)c3Cl)CC2)CC1]

CONTENT OF THE PRESENT INVENTION

The technical problem actually solved in the present disclosure is the defect that the existing antischizophrenic drugs have a single structure, for this purpose, the present disclosure provides a pyridinyl morpholine compound, a preparation method therefor and a use thereof. The pyridinyl morpholine compound not only has strong affinity for $D_2$, $D_3$, and 5-$HT_{2A}$ receptors, reasonable selectivity for $D_3/D_2$ receptor, but also has weak or no affinity for histamine $H_1$ receptor, and has low toxicity.

The present disclosure provides a pyridinyl morpholine compound represented by formula I, a pharmaceutically acceptable salt thereof, or a hydrate of the pharmaceutically acceptable salt thereof:

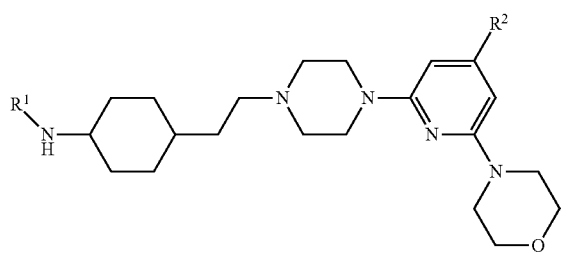

I wherein, $R^1$ is

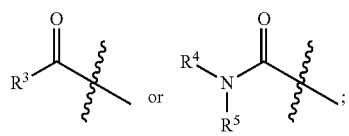

$R^3$ is $C_1$-$C_3$ alkyl, "$C_1$-$C_3$ alkyl substituted by one $C_1$-$C_3$ alkoxy", $C_3$-$C_6$ cycloalkyl, phenyl, "5- to 6-membered heteroaryl with 1 to 2 heteroatoms selected from one or more of N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom;

$R^4$ and $R^5$ are independently hydrogen or $C_1$-$C_3$ alkyl;

$R^2$ is phenyl, "5- to 6-membered heteroaryl with 1 to 2 heteroatoms selected from one or more of N, O and S", or, phenyl substituted by one or more $R^{2-1}$;

$R^{2-1}$ is independently $C_1$-$C_3$ alkoxy or halogen.

In a certain embodiment, certain substituents in the pyridinyl morpholine compound represented by formula I, the pharmaceutically acceptable salt thereof or the hydrate of the pharmaceutically acceptable salt thereof can further have the following definitions, and the definitions of the substituents not involved in the following are as described in any of the above schemes (this paragraph is hereinafter referred to as "in a certain embodiment"):

In a certain embodiment, the pyridinyl morpholine compound represented by formula I can be pyridinyl morpholine compound represented by formula I-1 and/or pyridinyl morpholine compound represented by formula I-2:

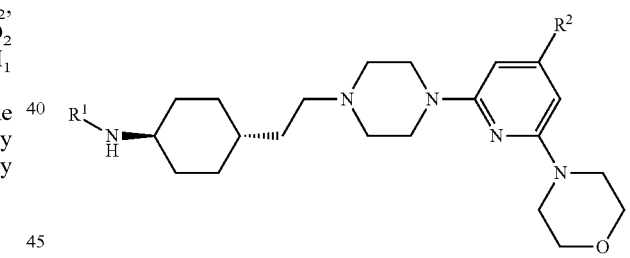

I-1

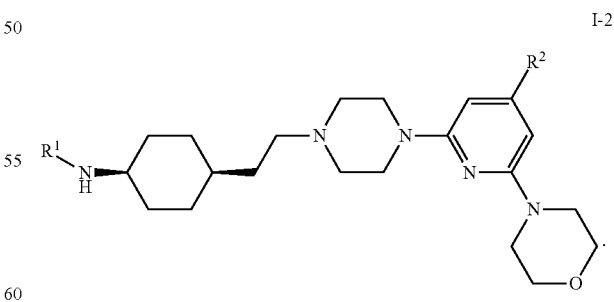

I-2

In a certain embodiment, the pyridinyl morpholine compound represented by formula I can be pyridinyl morpholine compound represented by formula I-1:

I-1

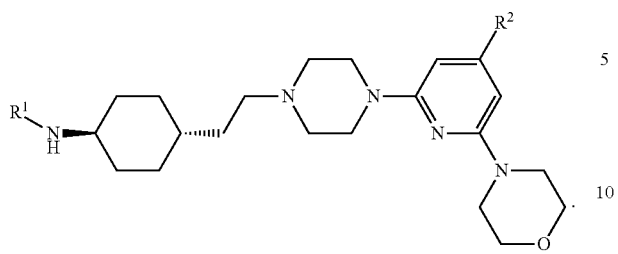

In a certain embodiment, $R^3$ is $C_1$-$C_3$ alkyl,

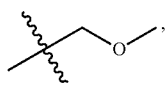 [SMILES: *COC]

$C_3$-$C_6$ cycloalkyl, "5- to 6-membered heteroaryl with one heteroatom selected from N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom.

In a certain embodiment, $R^3$ is $C_1$-$C_3$ alkyl,

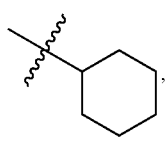

furanyl, pyridyl, tetrahydropyrrolyl, morpholinyl, piperidinyl or piperazinyl.

In a certain embodiment, $R^3$ is furanyl, pyridyl or tetrahydropyrrolyl.

In a certain embodiment, $R^3$ is $C_1$-$C_3$ alkyl,

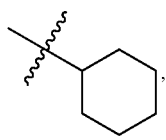 [SMILES: *C1CCCCC1]

furanyl, pyridyl, tetrahydropyrrolyl or piperazinyl.

In a certain embodiment, $R^3$ is "5- to 6-membered heteroaryl with 1 heteroatom selected from N and O" or tetrahydropyrrolyl.

In a certain embodiment, $R^3$ is $C_3$ alkyl, "$C_1$-$C_3$ alkyl substituted by one $C_1$-$C_3$ alkoxy", phenyl, tetrahydropyrrolyl, morpholinyl, piperidinyl, piperazinyl or methylpiperazinyl.

In a certain embodiment, $R^2$ is phenyl, "5- to 6-membered heteroaryl with 1 heteroatom selected from N, O and S", or phenyl substituted by one $R^{2-1}$.

In a certain embodiment, $R^2$ is phenyl, "5- to 6-membered heteroaryl with 1 heteroatom selected from N and S", or phenyl substituted by one $R^{2-1}$.

In a certain embodiment, $R^4$ and $R^5$ are independently $C_1$-$C_3$ alkyl.

In a certain embodiment, $R^{2-1}$ is $C_1$-$C_3$ alkoxy or fluorine.

In a certain embodiment: Where, $R^1$ is

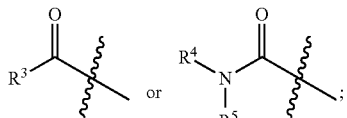

$R^3$ is $C_1$-$C_3$ alkyl,

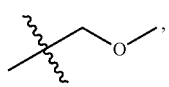 [SMILES: *COC]

$C_3$-$C_6$ cycloalkyl, "5- to 6-membered heteroaryl with one heteroatom selected from N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom;

$R^4$ and $R^5$ are independently hydrogen or $C_1$-$C_3$ alkyl;

$R^2$ is phenyl, "5- to 6-membered heteroaryl with one heteroatom selected from N, O and S", or, phenyl substituted by one or more $R^{2-1}$;

$R^{2-1}$ is independently $C_1$-$C_3$ alkoxy or halogen.

In a certain embodiment:
Where, $R^3$ is $C_1$-$C_3$ alkyl,

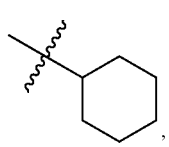

furanyl, pyridyl, tetrahydropyrrolyl, morpholinyl, piperidinyl or piperazinyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$.

In a certain embodiment:
Where, $R^3$ is furanyl, pyridyl or tetrahydropyrrolyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$;

$R^{2-1}$ is independently $C_1$-$C_3$ alkoxy or halogen;

$R^{2-1}$ is independently $C_1$-$C_3$ alkoxy or halogen.

In a certain embodiment:
Where, $R^3$ is $C_1$-$C_3$ alkyl,

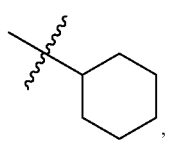 [SMILES: *C1CCCCC1]

uranyl, pyridyl, tetrahydropyrrolyl or piperazinyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$;

$R^{2-1}$ is independently $C_1$-$C_3$ alkoxy or halogen.

In a certain embodiment:

Where, $R^3$ is "5- to 6-membered heteroaryl with 1 heteroatom selected from N and O" or tetrahydropyrrolyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$;

$R^{2-1}$ is independently $C_1$-$C_3$ alkoxy or halogen.

In a certain embodiment:

$R^3$ is $C_3$ alkyl, "$C_1$-$C_3$ alkyl substituted by one $C_1$-$C_3$ alkoxy", phenyl, tetrahydropyrrolyl, morpholinyl, piperidinyl, piperazinyl or methylpiperazinyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$;

$R^{2-1}$ is independently $C_1$-$C_3$ alkoxy or halogen.

In a certain embodiment, when $R^3$ is $C_1$-$C_3$ alkyl, the $C_1$-$C_3$ alkyl can be methyl, ethyl, n-propyl, or isopropyl.

In a certain embodiment, when $R^3$ is $C_1$-$C_3$ alkyl substituted by one $C_1$-$C_3$ alkoxy, the $C_1$-$C_3$ alkoxy can be methoxy.

In a certain embodiment, when $R^3$ is $C_1$-$C_3$ alkyl substituted by one $C_1$-$C_3$ alkoxy, the $C_1$-$C_3$ alkyl can be methyl.

In a certain embodiment, when $R^3$ is $C_1$-$C_3$ alkyl substituted by one $C_1$-$C_3$ alkoxy, the $C_1$-$C_3$ alkyl substituted by one $C_1$-$C_3$ alkoxy can be

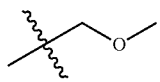

In a certain embodiment, when $R^3$ is $C_1$-$C_3$ alkoxy, the $C_1$-$C_3$ alkoxy can be ethoxy.

In a certain embodiment, when $R^3$ is $C_3$-$C_6$ cycloalkyl, the $C_3$-$C_6$ cycloalkyl can be cyclopropyl or cyclohexyl.

In a certain embodiment, when $R^3$ is "5- to 6-membered heteroaryl with 1 to 2 heteroatoms selected from one or more of N, O and S", the "the 5- to 6-membered heteroaryl with 1 to 2 heteroatoms selected from one or more of N, O and S" can be "5- to 6-membered heteroaryl with 1 heteroatom selected from N, O and S", can also be furanyl or pyridyl, can further be

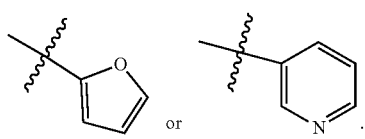 [SMILES: *c1ccco1 ; *c1cccnc1]

In a certain embodiment, when $R^3$ is "5- to 6-membered heterocycloalkyl with one heteroatom of N, and 0 or 1 heteroatom selected from N, O and S", the "5- to 6-membered heterocycloalkyl with one heteroatom of N, and 0 or 1 heteroatom selected from N, O and S" can be

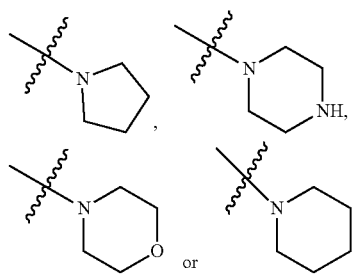

In a certain embodiment, when $R^3$ is "5- to 6-membered heterocycloalkyl with one heteroatom of N, and 0 or 1 heteroatom selected from N, O and S substituted by one $C_1$-$C_3$ alkyl", the $C_1$-$C_3$ alkyl can be methyl, ethyl, n-propyl, or isopropyl, can also be methyl.

In a certain embodiment, "5- to 6-membered heterocycloalkyl with one heteroatom of N, and 0 or 1 heteroatom selected from N, O and S substituted by one $C_1$-$C_3$ alkyl", the "5- to 6-membered heterocycloalkyl with one heteroatom of N, and 0 or 1 heteroatom selected from N, O and S" can be

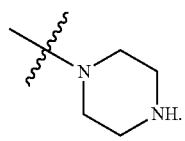 [SMILES: *N1CCNCC1]

In a certain embodiment, when $R^3$ is "5- to 6-membered heterocycloalkyl with one heteroatom of N, and 0 or 1 heteroatom selected from N, O and S substituted by one $C_1$-$C_3$ alkyl", the "5- to 6-membered heterocycloalkyl with one heteroatom of N, and 0 or 1 heteroatom selected from N, O and S substituted by one $C_1$-$C_3$ alkyl" can be

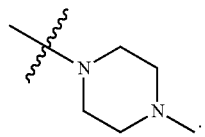 [SMILES: *N1CCN(C)CC1]

In a certain embodiment, when $R^4$ is $C_1$-$C_3$ alkyl, the $C_1$-$C_3$ alkyl can be methyl, ethyl, n-propyl, or isopropyl.

In a certain embodiment, when $R^5$ is $C_1$-$C_3$ alkyl, the $C_1$-$C_3$ alkyl can be methyl, ethyl, n-propyl, or isopropyl.

In a certain embodiment, $R^1$ can be

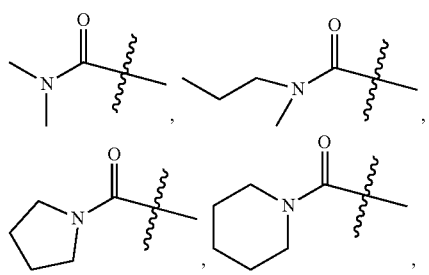

-continued

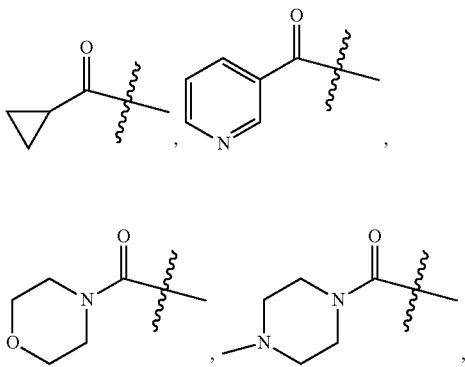
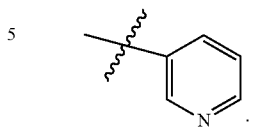
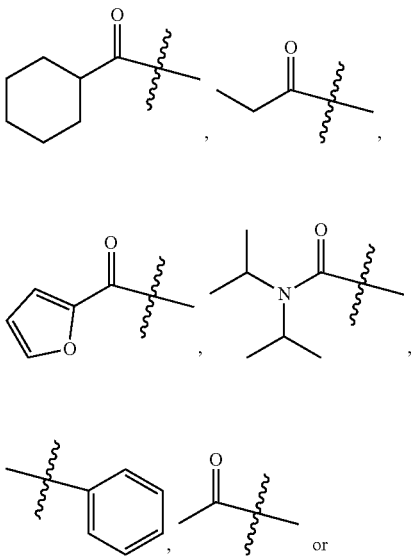
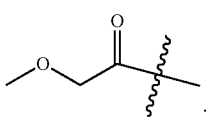

In a certain embodiment, when $R^2$ is "5- to 6-membered heteroaryl with 1 to 2 heteroatoms selected from one or more of N, O and S", the "5- to 6-membered heteroaryl with 1 to 2 heteroatoms selected from one or more of N, O and S" can be "5- to 6-membered heteroaryl with 1 heteroatom selected from N, O and S", can also be furanyl, thienyl, pyrrolyl or pyridyl, can further be

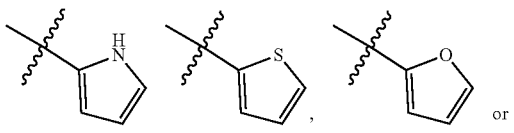 or

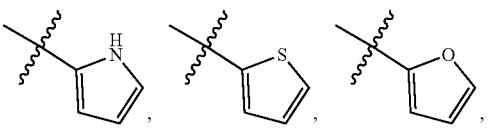

In a certain embodiment, when $R^{2-1}$ is $C_1$-$C_3$ alkoxy, the $C_1$-$C_3$ alkoxy can be methoxy, ethoxy, propoxy or isopropoxy, can also be methoxy.

In a certain embodiment, when $R^{2-1}$ is halogen, the halogen can be fluorine, chlorine, bromine or iodine, can also be fluorine.

In a certain embodiment, $R^2$ can be

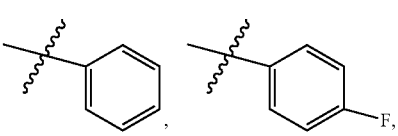

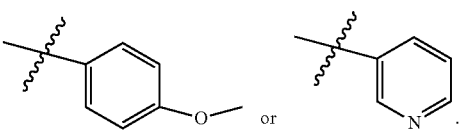

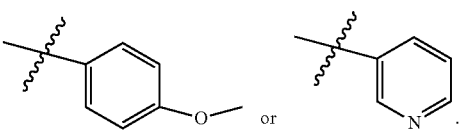

In a certain embodiment, in the pharmaceutically acceptable salt, the salt is hydrochloride, hydrobromide, sulfate, methanesulfonate or trifluoroacetate.

In a certain embodiment, in the pharmaceutically acceptable salt, relative to the pyridinyl morpholine compound represented by formula I, the number of the acid molecular contained in the salt is 0.5 to 2;

in a certain embodiment, in the hydrate of the pharmaceutically acceptable salt, the salt is hydrochloride, hydrobromide, sulfate, trifluoroacetate, methanesulfonate or palmitate;

in a certain embodiment, in the hydrate of the pharmaceutically acceptable salt, relative to the pyridinyl morpholine compound represented by formula I, the number of the acid molecular contained in the hydrate of the salt is 0.5 to 2;

in a certain embodiment, in the hydrate of the pharmaceutically acceptable salt, relative to the pyridinyl morpholine compound represented by formula I, the number of the water molecular contained in the hydrate of the salt is 0.5 to 2.

In a certain embodiment, in the pyridinyl morpholine compound represented by formula I, the pharmaceutically acceptable salt thereof or the hydrate of the pharmaceutically acceptable salt thereof, the pyridinyl morpholine compound represented by formula I can be any one of the following compounds:

| No. | Structure |
|---|---|
| I-1 | 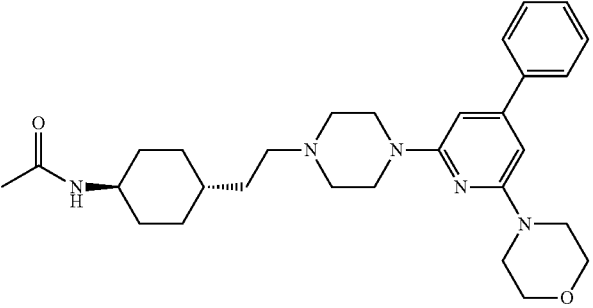 [SMILES: CC(=O)N[C@H]1CC[C@H](CCN2CCN(c3cc(-c4ccccc4)cc(N4CCOCC4)n3)CC2)CC1] |
| I-2 | 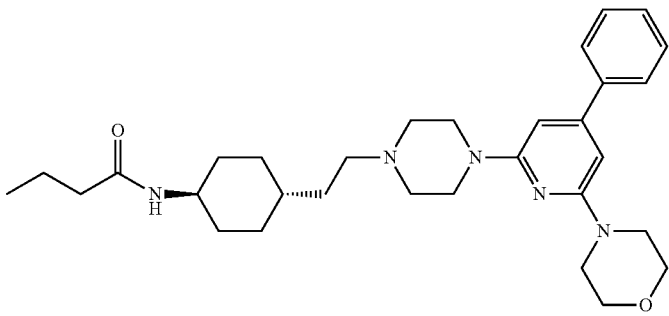 [SMILES: CCCC(=O)N[C@H]1CC[C@H](CCN2CCN(c3cc(-c4ccccc4)cc(N4CCOCC4)n3)CC2)CC1] |
| I-3 | 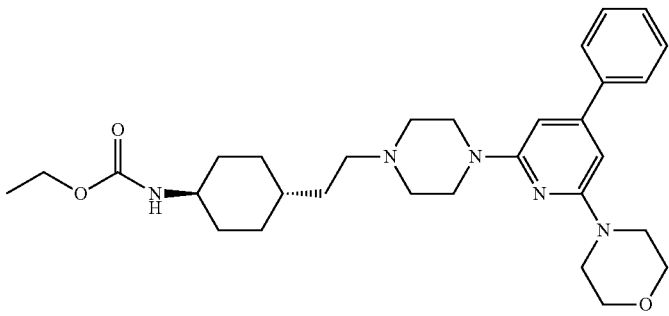 [SMILES: CCOC(=O)N[C@H]1CC[C@H](CCN2CCN(c3cc(-c4ccccc4)cc(N4CCOCC4)n3)CC2)CC1] |
| I-4 | 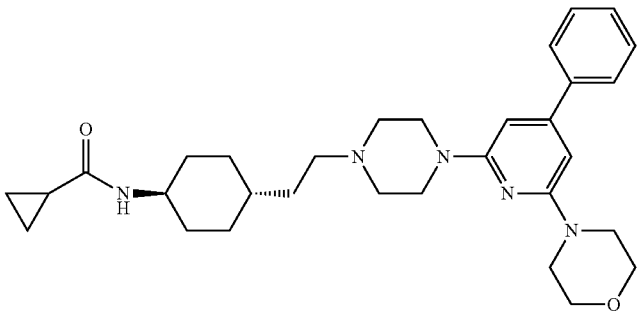 |
| I-5 | 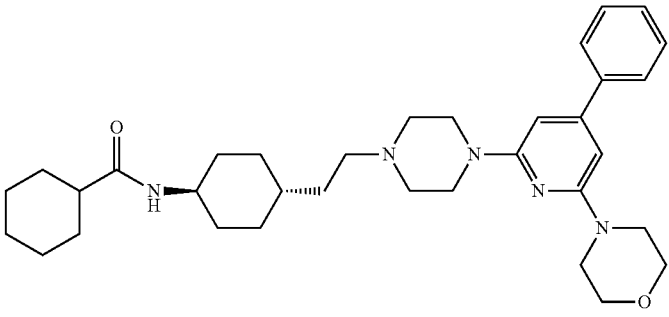 [SMILES: O=C(N[C@H]1CC[C@H](CCN2CCN(c3cc(-c4ccccc4)cc(N4CCOCC4)n3)CC2)CC1)C1CCCCC1] |

| No. | Structure |
|---|---|
| I-6 | 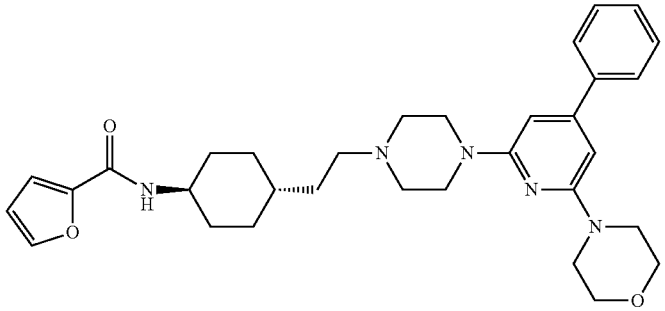 [SMILES: O=C(N[C@H]1CC[C@H](CCN2CCN(c3cc(-c4ccccc4)cc(N4CCOCC4)n3)CC2)CC1)c1ccco1] |
| I-7 | 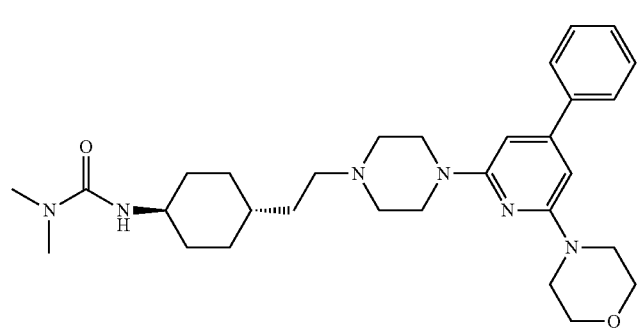 [SMILES: CN(C)C(=O)N[C@H]1CC[C@H](CCN2CCN(c3cc(-c4ccccc4)cc(N4CCOCC4)n3)CC2)CC1] |
| II-1 | 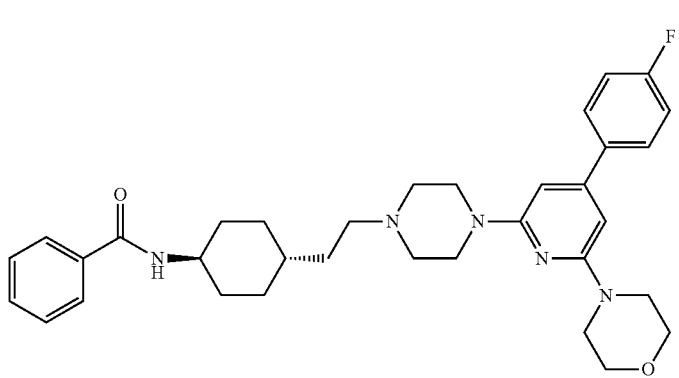 [SMILES: O=C(N[C@H]1CC[C@H](CCN2CCN(c3cc(-c4ccc(F)cc4)cc(N4CCOCC4)n3)CC2)CC1)c1ccccc1] |
| II-2 | 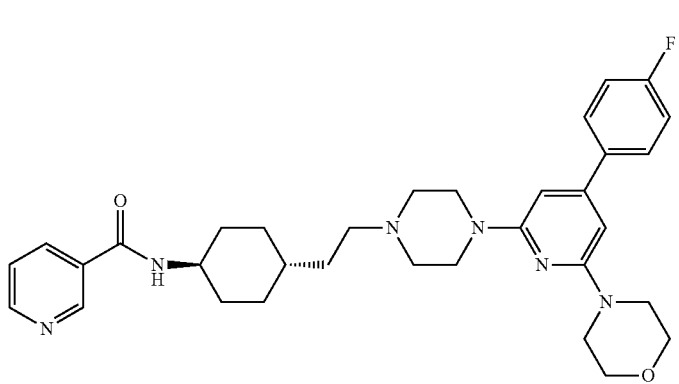 |

-continued

| No. | Structure |
|---|---|
| II-3 | 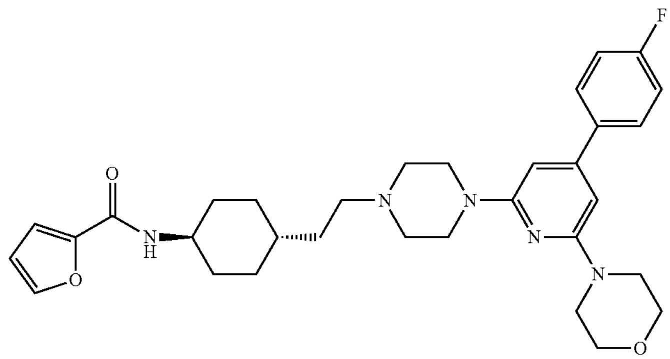 [SMILES: O=C(N[C@H]1CC[C@H](CCN2CCN(c3cc(-c4ccc(F)cc4)cc(N4CCOCC4)n3)CC2)CC1)c1ccco1] |
| II-4 | 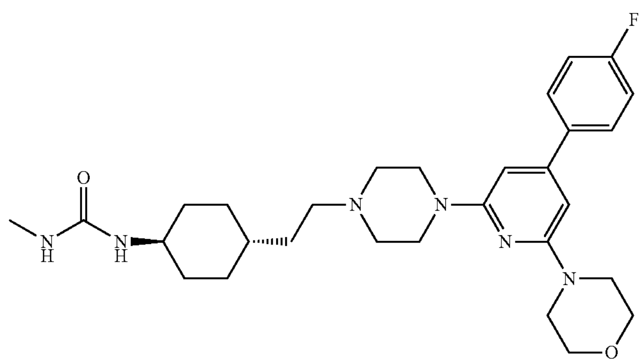 [SMILES: CNC(=O)N[C@H]1CC[C@H](CCN2CCN(c3cc(-c4ccc(F)cc4)cc(N4CCOCC4)n3)CC2)CC1] |
| II-5 | 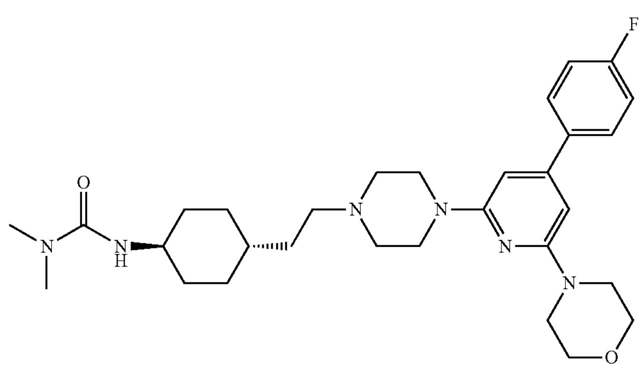 |
| II-6 | 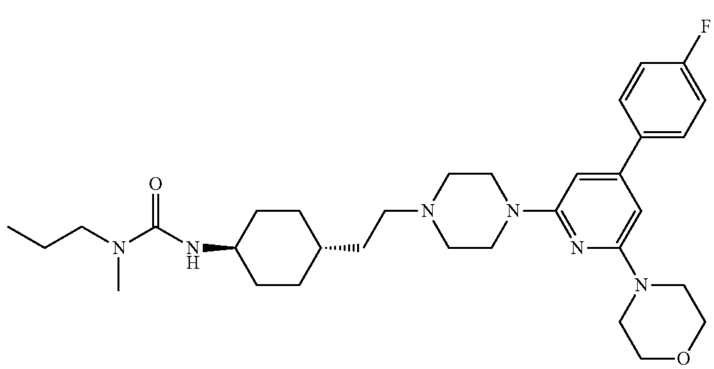 [SMILES: CCCN(C)C(=O)N[C@H]1CC[C@H](CCN2CCN(c3cc(-c4ccc(F)cc4)cc(N4CCOCC4)n3)CC2)CC1] |

| No. | Structure |
|---|---|
| III-1 | *(chemical structure)* |
| III-2 | *(chemical structure)* |
| III-3 | *(chemical structure)* |
| III-4 | *(chemical structure)* |

-continued
| No. | Structure |
|---|---|
| IV-1 | 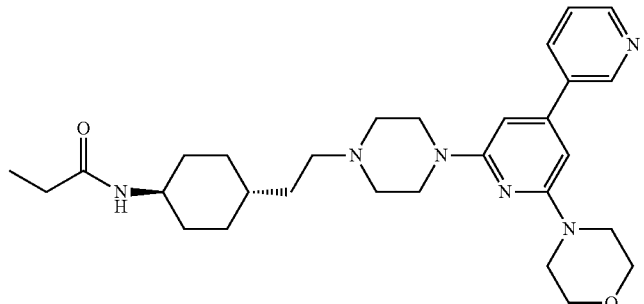 |
| IV-2 | 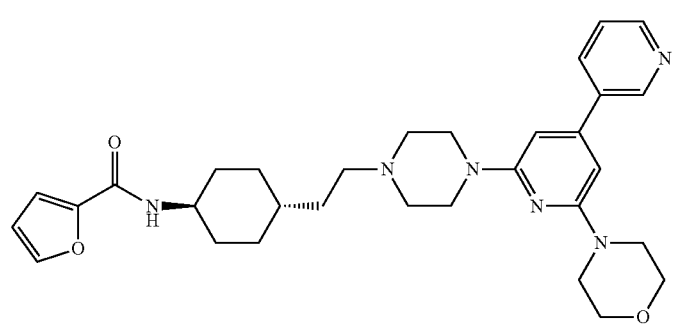 [SMILES: O=C(N[C@H]1CC[C@H](CCN2CCN(c3cc(-c4cccnc4)cc(N4CCOCC4)n3)CC2)CC1)c1ccco1] |
| IV-3 | 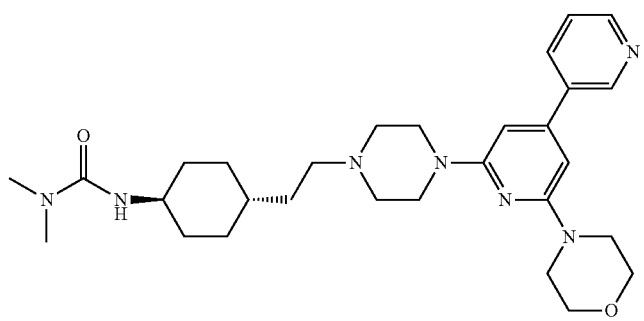 [SMILES: CN(C)C(=O)N[C@H]1CC[C@H](CCN2CCN(c3cc(-c4cccnc4)cc(N4CCOCC4)n3)CC2)CC1] |
| IV-4 | 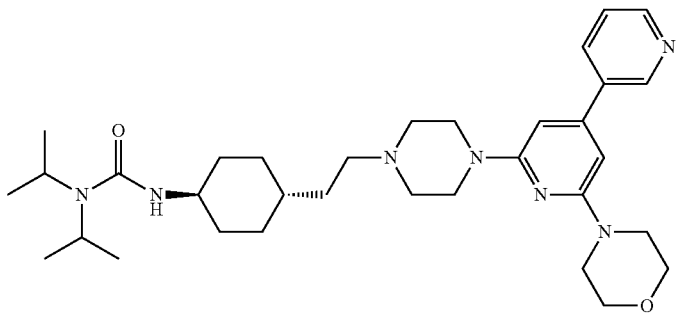 [SMILES: CC(C)N(C(=O)N[C@H]1CC[C@H](CCN2CCN(c3cc(-c4cccnc4)cc(N4CCOCC4)n3)CC2)CC1)C(C)C] |
| V-1 | 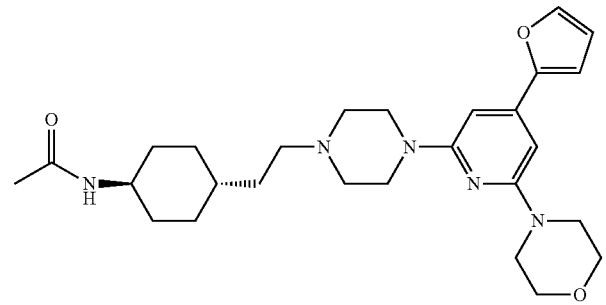 |

-continued
| No. | Structure |
|---|---|
| V-2 | 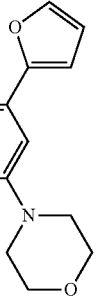 |
| V-3 | 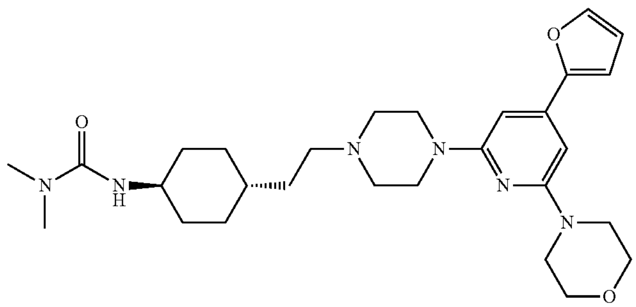 |
| V-4 | 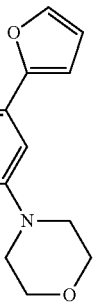 |
| V-5 | 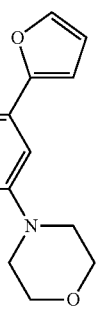 |
| VI-1 | 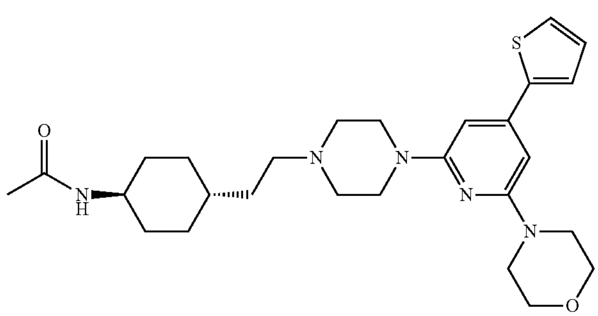 [SMILES: CC(=O)N[C@H]1CC[C@H](CCN2CCN(c3cc(-c4cccs4)cc(N4CCOCC4)n3)CC2)CC1] |

| No. | Structure |
|---|---|
| VI-2 | 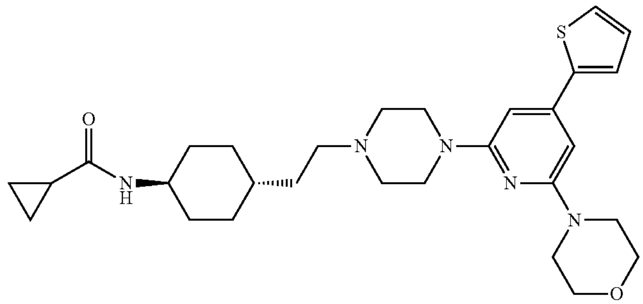 [SMILES: O=C(N[C@H]1CC[C@H](CCN2CCN(c3cc(-c4cccs4)cc(N4CCOCC4)n3)CC2)CC1)C1CC1] |
| VI-3 | 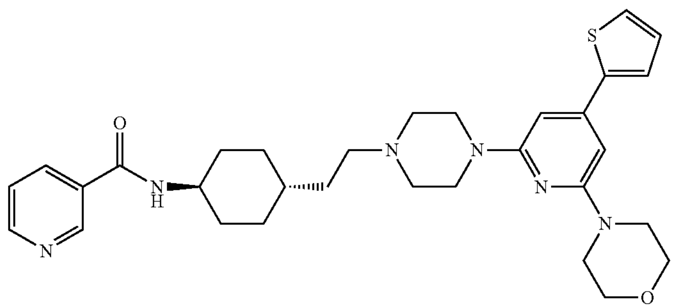 [SMILES: O=C(N[C@H]1CC[C@H](CCN2CCN(c3cc(-c4cccs4)cc(N4CCOCC4)n3)CC2)CC1)c1cccnc1] |
| VI-4 | 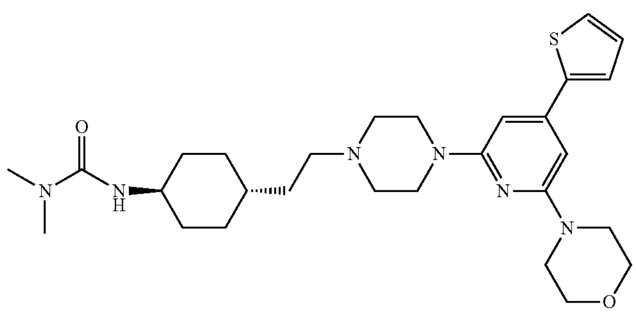 [SMILES: CN(C)C(=O)N[C@H]1CC[C@H](CCN2CCN(c3cc(-c4cccs4)cc(N4CCOCC4)n3)CC2)CC1] |
| VI-5 | 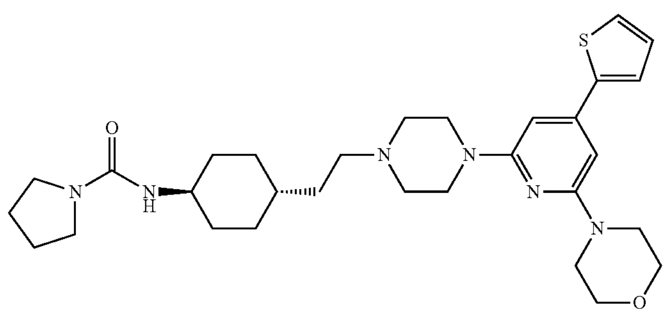 [SMILES: O=C(N[C@H]1CC[C@H](CCN2CCN(c3cc(-c4cccs4)cc(N4CCOCC4)n3)CC2)CC1)N1CCCC1] |
| VII-1 | 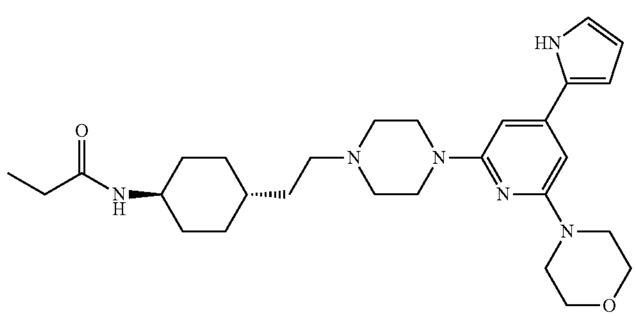 |

| No. | Structure |
|---|---|
| VII-2 | 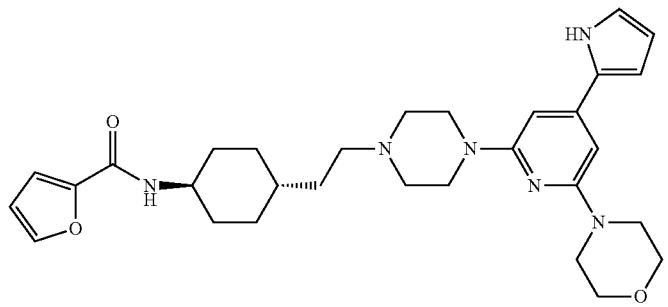 [SMILES: O=C(N[C@H]1CC[C@H](CCN2CCN(c3cc(-c4ccc[nH]4)cc(N4CCOCC4)n3)CC2)CC1)c1ccco1] |
| VII-3 | 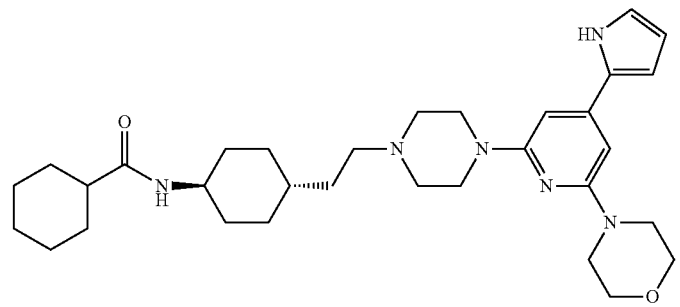 |
| VII-4 | 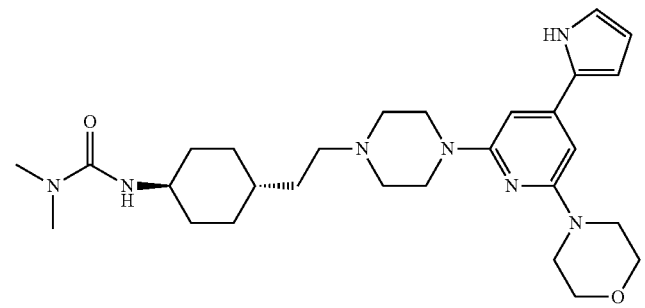 |
| VII-5 | 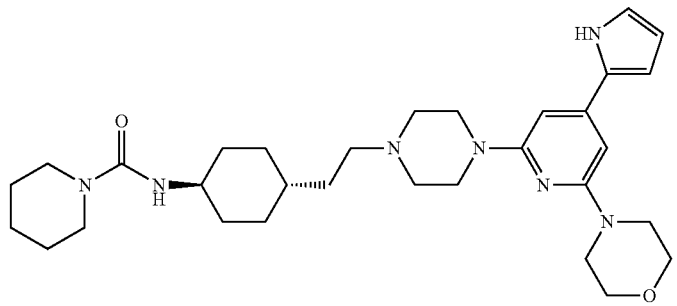 [SMILES: O=C(N[C@H]1CC[C@H](CCN2CCN(c3cc(-c4ccc[nH]4)cc(N4CCOCC4)n3)CC2)CC1)C1CCCCC1] |

In a certain embodiment, the pyridinyl morpholine compound represented by formula I can be any one of the following compounds:
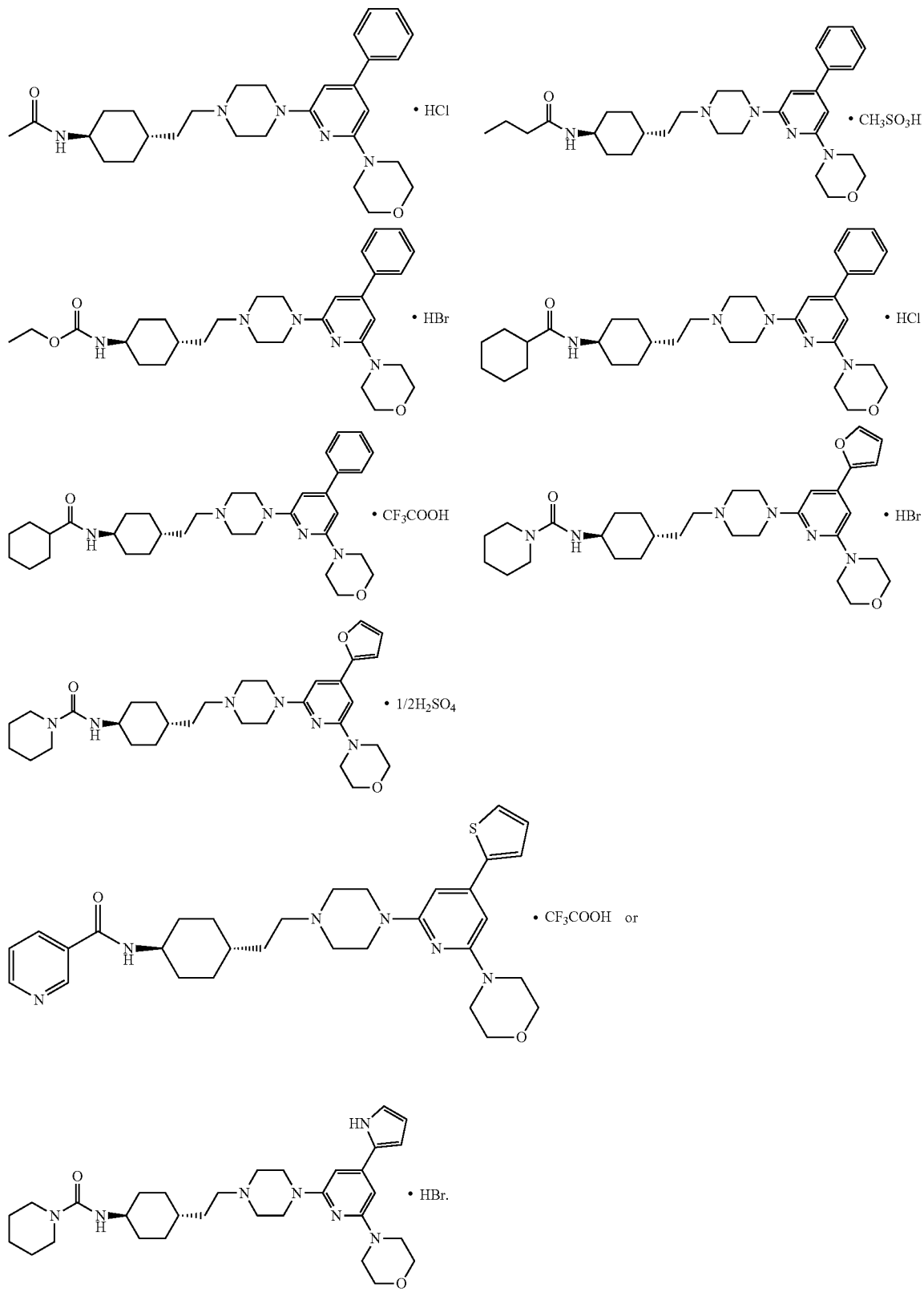

In a certain embodiment, the hydrate of the pharmaceutically acceptable salt of the pyridinyl morpholine compound represented by formula I can be the following compound:

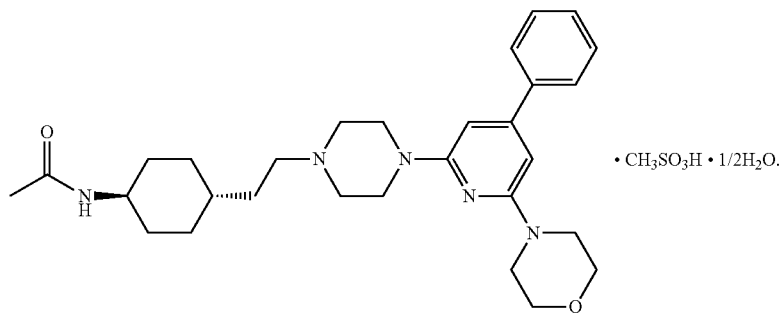 [SMILES: CC(=O)N[C@H]1CC[C@H](CCN2CCN(c3cc(-c4ccccc4)cc(N4CCOCC4)n3)CC2)CC1]

The present disclosure also provides a preparation method of the pyridinyl morpholine compound represented by formula I or the geometric isomer thereof, comprising conducting an amidation reaction as shown below with a compound represented by formula 6 and substance Y to obtain the pyridinyl morpholine compound represented by formula I; the substance Y is a compound represented by formula A or formula B;

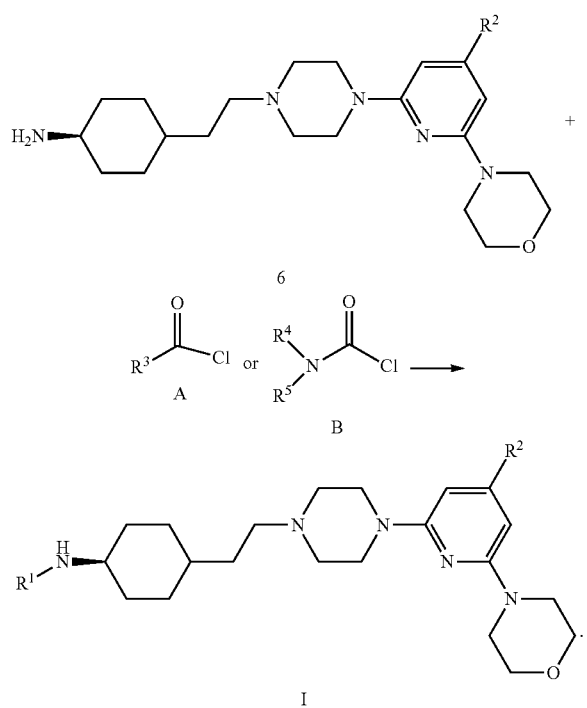

The present disclosure also provides a preparation method of the pharmaceutically acceptable salt or the hydrate of the salt of the pyridinyl morpholine compound represented by formula I or the geometric isomer thereof, comprising the following steps: in water and ethanol, performing a salt forming reaction between the pyridine morpholine compound represented by formula I and an acid to obtain the pharmaceutically acceptable salt or the hydrate of the salt of the pyridinyl morpholine compound represented by formula I.

In the preparation method, the acid can be hydrochloric acid, hydrobromic acid, sulfuric acid, methanesulfonic acid or trifluoroacetic acid.

In the preparation method, the acid and the water can be added in the form of an acid aqueous solution. The acid aqueous solution can be a 5% acid aqueous solution.

The present disclosure also provides a pharmaceutical composition, comprising substance X and pharmaceutical excipients; the substance X is the pyridinyl morpholine compound represented by formula I, the pharmaceutically acceptable salt thereof, or the hydrate of the pharmaceutically acceptable salt thereof.

In a certain embodiment of the pharmaceutical composition, the amount of the substance X can be changed according to the route of administration, patient age, patient body weight, patient sex, the type and severity of the disease for treatment, etc., which can be in a therapeutically effective amount, for example, 0.5-200 mg/kg body weight/day.

In a certain embodiment of the pharmaceutical composition, the content of the substance X can be 0.1%-99.5% (weight ratio).

In a certain embodiment of the pharmaceutical composition, the pharmaceutical excipient is a conventional pharmaceutical excipient in the pharmaceutical field, for example, spice, sweetener, diluent, excipient (such as water), filler (such as starch, sucrose, lactose, microcrystalline cellulose, etc.), adhesive (such as cellulose derivative, gelatin and polyvinyl pyrrolidone, etc.), wetting agent (such as glycerol, etc.), surfactant (such as hexadecanol, etc.), disintegrant (such as calcium carbonate, crospovidone, sodium starch glycolate, etc.), lubricant (such as talcum powder, sodium stearyl fumarate, calcium stearate and magnesium stearate, etc.).

In a certain embodiment of the pharmaceutical composition, the pharmaceutical excipient can be (1) sucrose, corn starch and magnesium stearate; or (2) water for injection.

In a certain embodiment of the pharmaceutical composition, the dosage form of the pharmaceutical composition can be tablet, capsule, powder, syrup, liquid, suspension or injection.

In a certain embodiment of the pharmaceutical composition, the administration mode of the pharmaceutical composition can be oral administration or injection administration.

In a certain embodiment of the pharmaceutical composition, the pharmaceutical composition can be a pharmaceutical composition for the treatment of schizophrenia.

The pharmaceutical composition of the present disclosure can be prepared by any method known in the art.

The present disclosure also provides use of the substance X in the manufacture of a medicament for the treatment of schizophrenia; the substance X is the above mentioned pyridinyl morpholine compound represented by formula I, the pharmaceutically acceptable salt thereof, or the hydrate of the pharmaceutically acceptable salt thereof.

The present disclosure also provides use of the substance X in the manufacture of an antagonist; the substance X is the above mentioned pyridinyl morpholine compound represented by formula I, the pharmaceutically acceptable salt thereof, or the hydrate of the pharmaceutically acceptable salt thereof, and the antagonist is selected from one or more of $D_2$ antagonist, $D_3$ antagonist and 5-$HT_{2A}$ antagonist.

Unless otherwise stated, the following terms appearing in the description and claims of the present disclosure have the following definitions:

The term "pharmaceutically acceptable" refers to salts, solvents, excipients, etc. that are generally non-toxic, safe, and suitable for patient use. The "patient" is preferred mammal, more preferably human.

The term "pharmaceutically acceptable salt" refers to the salt prepared by the compound of the present disclosure and a relatively nontoxic and pharmaceutically acceptable acid or base. When the compound of the present disclosure contains a relatively acidic functional group, a base addition salt can be obtained by bringing the prototype form of the compound into contact with a sufficient amount of pharmaceutically acceptable base in a suitable inert solvent. Pharmaceutically acceptable base addition salts include, but are not limited to, lithium salt, sodium salt, potassium salt, calcium salt, aluminum salt, magnesium salt, zinc salt, bismuth salt, ammonium salt, diethanolamine salt. When the compound of the present disclosure contains a relatively basic functional group, an acid addition salt can be obtained by bringing the prototype form of the compound into contact with a sufficient amount of pharmaceutically acceptable acid in a suitable inert solvent. The pharmaceutically acceptable acids include inorganic acids, and the inorganic acids include but are not limited to: hydrochloric acid, hydrobromic acid, hydroiodic acid, nitric acid, carbonic acid, phosphoric acid, phosphorous acid, sulfuric acid, etc. The pharmaceutically acceptable acid includes organic acid, and the organic acid includes but is not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid)), amino acid (such as glutamic acid, arginine), etc. When compounds of the present disclosure contain relatively acidic and relatively basic functional groups, they can be converted into base addition salts or acid addition salts. For details, see Berge et al., "Pharmaceutical Salts", Journal of Pharmaceutical Science 66: 1-19 (1977), or, Handbook of Pharmaceutical Salts: Properties, Selection, and Use (P. Heinrich Stahl and Camille G. Wermuth, ed., Wiley-VCH, 2002).

As mentioned above, the term "hydrate of pharmaceutically acceptable salt" refers to substance formed by combining the compound of the present disclosure with 1. a relatively nontoxic and pharmaceutically acceptable acid or base and 2. stoichiometric or non-stoichiometric water. The "hydrate of pharmaceutically acceptable salt" includes but is not limited to hydrochloric acid monohydrate of the compound of the present disclosure.

When an arbitrary variable (e.g., $R^{2-1}$) appears many times in the definition of a compound, the definition of each occurrence of the variable has nothing to do with the definitions of other occurrences, and their meanings are independent of each other and have no influence on each other. Therefore, if a group is substituted by 1, 2 or 3 $R^{2-1}$, that is, the group may be substituted by up to 3 $R^{2-1}$ groups, the definition of this position $R^{2-1}$ is independent of the definition of the remaining position $R^{2-1}$. Additionally, combinations of substituents and/or variables are permissible only if such combinations result in stable compounds.

The term "alkyl" refers to a saturated straight or branched monovalent hydrocarbon group having one to three carbon atoms (e.g., $C_1$-$C_3$ alkyl). Embodiments of alkyl include but are not limited to methyl, ethyl, 1-propyl, 2-propyl.

The term "cycloalkyl" refers to a saturated, monocyclic, cyclic hydrocarbon atomic groups having three to six carbon atoms (e.g., $C_3$-$C_6$ cycloalkyl).

The term "heterocycloalkyl" refers to a saturated monocyclic group having 3 to 6 ring atoms, wherein at least one ring atom is a heteroatom independently selected from oxygen, sulfur, and nitrogen, and the remaining ring atoms are C.

The term "heteroaryl" refers to an aromatic monocyclic group having 5 to 6 ring atoms, wherein at least one ring atom is a heteroatom independently selected from oxygen, sulfur, and nitrogen, and the remaining ring atoms are C.

The term "pharmaceutical excipients" refers to the excipients and additives used in the manufacture of drugs and the formulation of prescriptions, which are all substances contained in pharmaceutical preparations except active ingredients. See Pharmacopoeia of the People's Republic of China (2015 Edition) Part IV, or, Handbook of Pharmaceutical Excipients (Raymond C Rowe, 2009 Sixth Edition).

The term "treatment" refers to a therapeutic therapy. Regarding to a specific disease, the treatment refers to: (1) alleviation of one or more biological manifestations of a disorder or disease, (2) interfering with (a) one or more points in the biological cascade leading to or causing a disease or (b) one or more biological manifestations of the disease, (3) improvement of one or more symptoms, effects or side effects associated with the disease, or one or more symptoms, effects or side effects associated with the disease or treatment thereof, or (4) slowdown of the progression of a disease or one or more biological manifestations of the disease.

The term "therapeutically effective amount" refers to an amount of compound that, when administered to a patient in need thereof, is sufficient to effectively treat the disorders or diseases described herein. The "therapeutically effective amount" is changed according to the compound, the disease and its severity, and the age of the patient to be treated, and can be adjusted as needed by those skilled in the art.

On the basis of not violating the common sense in the field, the above-mentioned preferred conditions can be arbitrarily combined to obtain the preferred embodiments of the present disclosure.

The reagents and raw materials used in the present disclosure are commercially available.

The positive progressive effect of the present disclosure is:

1. The compound of the present disclosure not only has strong affinity for $D_2$, $D_3$, and 5-$HT_{2A}$ receptors, reasonable selectivity for $D_3$/$D_2$ receptor, but also has obvious characteristics of receptor action mechanism.

2. The compound of the present disclosure has weak or no affinity for $H_1$ receptor, has low side effects related to the receptor, and has good target selectivity.

3. The compound of the present disclosure has good anti-schizophrenia effects on various animal models in vivo, and has broad-spectrum anti-schizophrenia effects.

4. The compound of the present disclosure has low acute toxicity and good druggability and safety.

DETAILED DESCRIPTION OF THE PREFERRED EMBODIMENT

The present disclosure is further described below by way of embodiments, but the present disclosure is not thereby limited to the scope of the described embodiments. The experimental methods not specified in the specific conditions in the following embodiments are selected according to the conventional methods and conditions, or according to the commodity instructions.

The compounds of the present disclosure can be prepared by the following general synthetic method. Further, the present disclosure also refers to the methods reported in WO2010070370 and WO2011073705 to synthesize the compound cariprazine hydrochloride reported in the literature, which is used as a control sample for in vitro and in vivo activity screening.

General Synthetic Method:

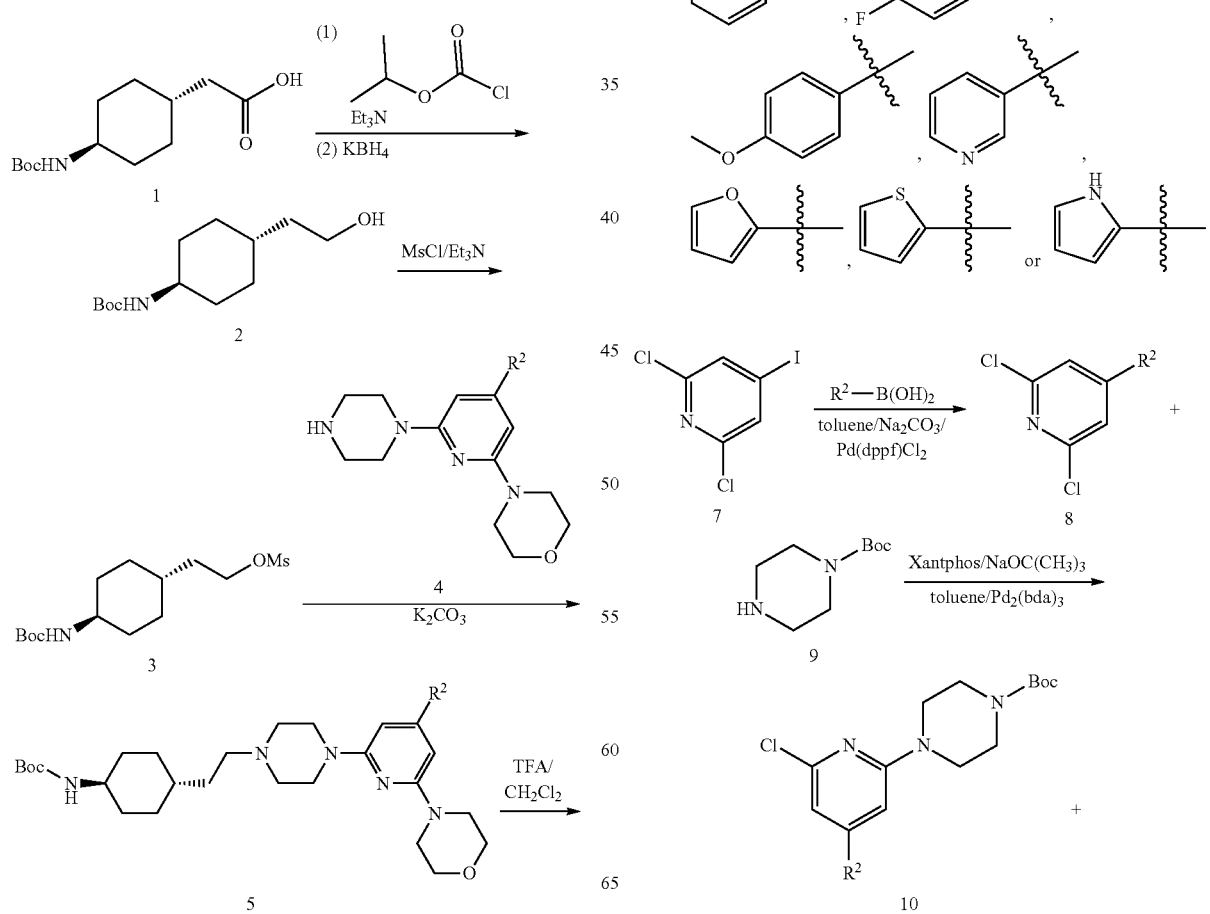

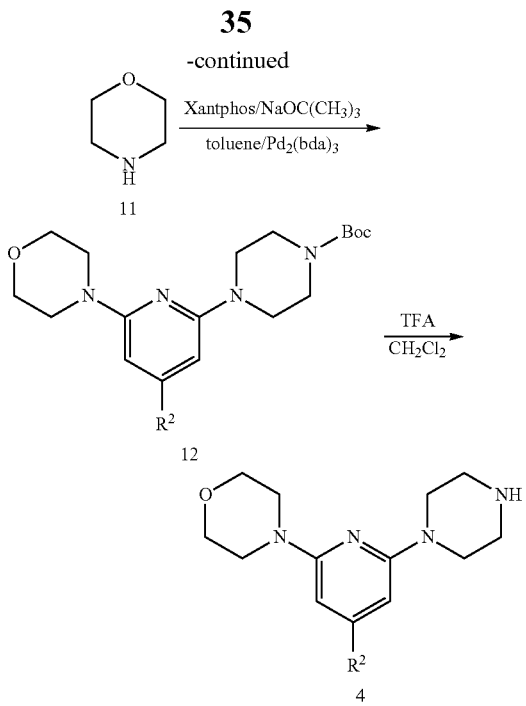

Synthesis of Intermediate 2

Compound 1 (25.7 g, 0.1 mol) was added to dichloromethane (200 mL), and then the mixture was cooled to 0° C. in an ice bath, and triethylamine (0.25 mol) was added dropwise, and isopropyl chloroformate (0.12 mol) was slowly added dropwise. The mixture was stirred at room temperature for 3 to 5 hours, cooled to 5° C., and then cold water (1 L) was added thereto, and the mixture was stirred for 0.5 hours, and the layers was separated. The organic layer was washed with saturated brine, evaporated to dryness. Under the protection of $N_2$, anhydrous THF was added thereto, and the temperature was lowered to 0° C., and then $KBH_4$ (8.1 g, 0.15 mol) was slowly added in batches. The mixture was stirred at room temperature for 4 to 5 hours, then cooled to 5° C. or less, and saturated ammonium chloride solution was slowly added dropwise until bubbles were not formed. The system was concentrated under reduced pressure to near dryness, and water/dichloromethane were added thereto, and the layers were separated, and then the organic layer was washed with saturated $Na_2CO_3$ solution, water, and saturated brine successively, then evaporated to dryness to obtain intermediate 2.

Synthesis of Intermediate 3

Intermediate 2 (9.7 g, 0.04 mol) and triethylamine (0.12 mol) were added to dichloromethane (100 mL), and a solution of methanesulfonyl chloride (0.048 mol) in dichloromethane (40 mL) was slowly added dropwise at about 0° C., and then the mixture was stirred at room temperature for 2 to 4 hours. The reaction solution was washed with water, 1% aqueous sodium hydroxide solution, water, and saturated brine successively, evaporated to dryness, and recrystallized with 95% ethanol to obtain intermediate 3.

Synthesis of Intermediate 4

2,6-Dichloro-4-iodopyridine (5 g, 18.33 mmol), arylboronic acid compound (18.33 mmol), Pd(dppf)Cl$_2$ (0.68 g, 1.83 mmol), toluene (120 mL), sodium carbonate (7.74 g, 55.21 mmol) were added to a 250 mL single-necked flask. Under the protection of nitrogen, the mixture was reacted at external temperature of 80° C. for 14 to 18 hours, and the completion of reaction was detected by TLC. The mixture was cooled to room temperature, filtered, and the filtrate was concentrated and purified by column chromatography to obtain product 8.

The product 8 (15.47 mmol), N-Boc-piperazine (2.88 g, 15.47 mmol), Xantphos (4,5-bis(diphenylphosphino)-9,9-dimethylxanthene) (0.9 g, 1.55 mmol), Pd$_2$(dba)$_3$ (0.35 g, 0.39 mmol), sodium tert-butanol (2.97 g, 23.21 mmol) and toluene (80 mL) were added to a 250 mL single-necked flask. Under the protection of nitrogen, the mixture was reacted at external temperature of 80° C. for 10 to 16 hours, and the completion of reaction was detected by TLC. The mixture was cooled to room temperature, filtered, and the filtrate was concentrated and purified by column chromatography to obtain product 10. The product 10 (3.75 mmol), morpholine (0.34 g, 3.75 mmol), Xantphos (4,5-bis(diphenylphosphino)-9,9-dimethylxanthene) (0.21 g, 0.37 mmol), Pd$_2$(dba)$_3$ (0.09 g, 0.1 mmol), sodium tert-butanol (0.72 g, 7.5 mmol) and toluene (20 mL) were added to a 100 mL single-necked flask. Under the protection of nitrogen, the mixture was reacted at external temperature of 80° C. for 10 to 15 hours, and the completion of reaction was detected by TLC. The mixture was cooled to room temperature, filtered, and the filtrate was concentrated and purified by column chromatography to obtain product 12. The product was dissolved in CH$_2$Cl$_2$ (50 mL), and then 5 equivalents of trifluoroacetic acid was added, and the reaction solution was stirred at room temperature for 8 to 10 hours, and the completion of reaction was detected by TLC. The pH of the reaction solution was adjusted to 10 to 12 with 20% NaOH aqueous solution, and the reaction solution was stirred for 10 min, and then the layers were separated. The organic layer was washed with H$_2$O (30 mL×2) and saturated brine (50 mL×2) successively, dried over anhydrous Na$_2$SO$_4$ for 1 hour, filtered and concentrated to obtain intermediate 4.

Synthesis of Intermediate 5

Intermediates 3 (6.4 g, 0.02 mol), intermediate 4 (0.018 mol), anhydrous potassium carbonate (5.5 g, 0.04 mol) were added to acetonitrile (100 mL), and the reaction was refluxed overnight, filtered. The filter cake was washed twice with acetonitrile, and the filtrate was combined, evaporated to dryness, and then the residue was recrystallized with anhydrous ethanol to obtain intermediates 5.

Synthesis of Intermediate 6

Intermediate 5 (10 mmol) was added to dichloromethane (40 mL), and then trifluoroacetic acid (7 mL) was slowly added dropwise, and the mixture was stirred at room temperature overnight. The system was washed with water, 5% NaOH aqueous solution, and saturated brine successively, and the organic layer was concentrated to dryness to obtain intermediate 6.

Synthesis of Compound Represented by General Formula (I)

Intermediate 6 (5 mmol), triethylamine (6 mmol), and dichloromethane (10 mL) were added to a 50 mL three-necked flask, and a solution of acyl chloride (5.5 mmol) in dichloromethane (10 mL) was added dropwise at 0 to 5° C.

After the dropwise addition was completed, the mixture was stirred at room temperature for 2-5 hours, and the system was washed with water and saturated brine successively. The organic layer was concentrated to dryness, and recrystallized with anhydrous ethanol to obtain the compound of the present disclosure.

Synthesis of the Salt of Compound Represented by General Formula (I)

The compound represented by general formula (I) was placed in 5% acid/ethanol and refluxed to dissolve, and the mixture was cooled to precipitate the salt of the compound, and the acid can be hydrochloric acid, hydrobromic acid, sulfuric acid, methanesulfonic acid, trifluoroacetic acid.

In the above general method, $R^3$ is $C_1$-$C_3$ alkyl, "$C_1$-$C_3$ alkyl substituted by one $C_1$-$C_3$ alkoxy", $C_3$-$C_6$ cycloalkyl, phenyl, "5- to 6-membered heteroaryl with 1 to 2 heteroatoms selected from one or more of N, O and S", "5- to 6-membered heterocycloalkyl with one of N atom, and 0 or 1 heteroatom selected from N, O and S", or, "5- to 6-membered heterocycloalkyl with one of N atom, and 0 or 1 heteroatom selected from N, O and S" substituted by one $C_1$-$C_3$ alkyl; the heterocycloalkyl is connected to the carbonyl in $R^1$ by N atom;

$R^4$ and $R^5$ are independently hydrogen or $C_1$-$C_3$ alkyl.

Example 1

Preparation of N-(trans-4-(2-(4-(6-morpholino-4-phenylpyridin-2-yl)piperazin-1-yl)ethyl)cyclohexyl) acetamide (I-1) and the salt thereof trans-4-(2-(4-(6-Morpholino-4-phenylpyridin-2-yl) piperazin-1-yl)ethyl)cyclohexyl)-1-amine (intermediate 6-1, prepared according to the general synthetic method)

(1.0 g, 2.2 mmol) [孟成1] and triethylamine (3.3 mmol) were added to $CH_2Cl_2$ (20 mL), and the mixture was stirred, and a solution of acetyl chloride (0.2 g, 2.4 mmol) in $CH_2Cl_2$ (5 mL) was added dropwise at 0 to 5° C. After the dropwise addition was completed, the mixture was stirred at room temperature for 2-4 hours, and the system was washed with water and saturated brine successively, and then the organic layer was concentrated to dryness, and recrystallized with anhydrous ethanol to obtain 0.8 g of white solid with a yield of 74%.

$^1$H NMR (CDCl$_3$ δ:ppm) δ 7.52-7.51 (m, 2H), 7.46 (d, J=4.2 Hz, 2H), 7.36-7.35 (m, 2H), 7.08-7.06 (m, 1H), 6.25 (s, 2H), 3.88-3.86 (m, 1H), 3.85-3.79 (m, 4H), 3.59 (brs, 4H), 3.54-3.48 (m, 4H), 2.56 (brs, 4H), 2.48-2.35 (m, 2H), 2.12-2.03 (m, 2H), 2.01 (s, 3H), 1.85 (d, J=12.6 Hz, 2H), 1.53-1.43 (m, 2H), 1.22-1.20 (m, 5H). ESI-MS:492[M+H$^+$].

Preparation of the Hydrochloride of Compound I-1

Compound I-1 (0.5 g, 1.0 mmol) and 5% hydrochloric acid aqueous solution (1.1 mmol) were added to ethanol (10 mL), refluxed to dissolve, cooled to precipitate a white solid, and filtered to obtain 0.4 g of white solid with a yield of 75.7%.

Element analysis: $C_{29}H_{41}N_5O_2 \cdot HCl$ (theoretical value %: C, 65.95; H, 8.02; N, 13.26; experimental value %: C, 65.90; H, 8.13; N, 13.21).

Preparation of the Methanesulfonate Hemihydrate of Compound I-1

Compound I-1 (0.5 g, 1.0 mmol) and methanesulfonic acid aqueous solution (1.1 mmol) were added to ethanol (10 mL), refluxed to dissolve, cooled to precipitate a white solid, and filtered to obtain 0.41 g of white solid with a yield of 77.6%.

Element analysis: $C_{29}H_{41}N_5O_2 \cdot CH_4O_3S \cdot \frac{1}{2}H_2O$ (theoretical value %: C, 60.38; H, 7.77, N, 11.74; experimental value %: C, 60.29; H, 7.83; N, 11.57).

Example 2

Preparation of N-(trans-4-(2-(4-(6-morpholino-4-phenylpyridin-2-yl)piperazin-1-yl)ethyl)cyclohexyl) butyramide (I-2) and the salt thereof Intermediate 6-1 (5.0 mmol) (prepared according to the general synthetic method) and butyryl chloride (5.5 mmol) were used as raw materials, and 2.1 g of compound I-2 as white solid with a yield of 80% was obtained according to the preparation method of compound I-1.

$^1$H NMR (CDCl$_3$ δ:ppm) δ 7.53-7.52 (m, 2H), 7.44 (d, J=4.2 Hz, 2H), 7.35-7.34 (m, 2H), 7.07-7.05 (m, 1H), 6.23 (s, 2H), 3.84-3.82 (m, 1H), 3.81-3.75 (m, 4H), 3.56 (brs, 4H), 3.51-3.45 (m, 4H), 2.53 (brs, 4H), 2.46-2.33 (m, 2H), 2.31 (t, J=5.6 Hz, 2H) 2.10-2.01 (m, 2H), 1.84 (d, J=12.6 Hz, 2H), 1.50-1.42 (m, 2H), 1.34-1.32 (m, 2H), 1.21-1.19 (m, 5H), 0.58 (s, 3H). ESI-MS:520[M+H$^+$].

Preparation of the Methanesulfonate of Compound I-2

Compound I-2 (1.0 mmol) and methanesulfonic acid aqueous solution (1.0 mmol) were used as raw materials, and 0.45 g of white solid with a yield of 73% was obtained according to the synthetic method of the hydrochloride of compound I-1.

Element analysis: $C_{31}H_{45}N_5O_2 \cdot CH_4O_3S$ (theoretical value %: C, 62.41; H, 8.02; N, 11.37; experimental value %: C, 62.58; H, 7.89; N, 11.44).

Example 3

Preparation of ethyl ((trans)-4-(2-(4-(6-morpholino-4-phenylpyridin-2-yl)piperazin-1-yl)ethyl)cyclohexyl)carbamate (I-3) and the salt thereof Intermediate 6-1 (5.0 mmol) (prepared according to the general synthetic method) and ethyl chloroformate (5.5 mmol) were used as raw materials, and 1.9 g of compound I-3 as white solid with a yield of 72.8% was obtained according to the preparation method of compound I-1.

$^1$H NMR (CDCl$_3$, δ:ppm) δ 7.55-7.54 (m, 2H), 7.47 (d, J=4.2 Hz, 2H), 7.37-7.36 (m, 2H), 7.06-7.04 (m, 1H), 6.25 (s, 2H), 3.94 (q, J=7.0 Hz, 2H), 3.83-3.81 (m, 1H), 3.80-3.74 (m, 4H), 3.55 (brs, 4H), 3.50-3.44 (m, 4H), 2.55 (brs, 4H), 2.47-2.34 (m, 2H), 2.11-2.02 (m, 2H), 1.86 (d, J=12.6 Hz, 2H), 1.51-1.43 (m, 2H), 1.22-1.20 (m, 5H), 1.06 (t, J=7.0 Hz, 3H). ESI-MS:522[M+H$^+$].

Preparation of the Hydrobromide of Compound I-3

Compound I-3 (1 mmol) and 5% hydrobromic acid aqueous solution (1 mmol) were used as raw materials, and 0.48 g of white solid with a yield of 80% was obtained according to the synthetic method of the hydrochloride of compound I-1.

Element analysis: $C_{30}H_{43}N_5O_3 \cdot HBr$ (theoretical value %: C, 59.79; H, 7.36; N, 11.62; experimental value %: C, 59.84; H, 7.27; N, 11.69).

Example 4

Preparation of N-((trans)-4-(2-(4-(6-morpholino-4-phenylpyridin-2-yl)piperazin-1-yl)ethyl)cyclohexyl) cyclopropanecarboxamide (I-4)

Intermediate 6-1 (5.0 mmol) (prepared according to the general synthetic method), cyclopropanecarbonyl chloride (5.5 mmol) were used as raw materials, and 2.2 g of compound I-4 as white solid with a yield of 84.6% was obtained according to the preparation method of compound I-1.

$^1$H NMR (CDCl$_3$, δ:ppm) δ 7.55-7.54 (m, 2H), 7.48 (d, J=4.2 Hz, 2H), 7.39-7.38 (m, 2H), 7.11-7.09 (m, 1H), 6.27 (s, 2H), 3.90-3.88 (m, 1H), 3.87-3.81 (m, 4H), 3.61 (brs, 4H), 3.56-3.50 (m, 4H), 2.58 (brs, 4H), 2.49-2.34 (m, 2H), 2.14-2.05 (m, 2H), 1.91 (d, J=12.6 Hz, 2H), 1.48-1.41 (m, 3H), 1.26-1.24 (m, 5H), 0.83-0.81 (m, 2H), 0.54-0.52 (m, 2H).

ESI-MS:518[M+H$^+$].

Example 5

Preparation of N-((trans)-4-(2-(4-(6-morpholino-4-phenylpyridin-2-yl)piperazin-1-yl)cyclohexyl)cyclohexanecarboxamide (I-5) and the salt thereof Intermediate 6-1 (5.0 mmol) (prepared according to the general synthetic method) and cyclohexanecarbonyl chloride (5.5 mmol) were used as raw materials, and 2.0 g of compound I-5 as white solid with a yield of 71% was obtained according to the preparation method of compound I-1.

$^1$H NMR (CDCl$_3$, δ:ppm) δ 7.51-7.50 (m, 2H), 7.45 (d, J=4.2 Hz, 2H), 7.35-7.34 (m, 2H), 7.07-7.05 (m, 1H), 6.24 (s, 2H), 3.89-3.87 (m, 1H), 3.84-3.78 (m, 4H), 3.58 (brs, 4H), 3.53-3.47 (m, 4H), 2.54 (brs, 4H), 2.46-2.33 (m, 3H), 2.11-2.02 (m, 2H), 1.87 (d, J=12 Hz, 2H), 1.68-1.59 (m, 5H), 1.51-1.41 (m, 7H), 1.21-1.19 (m, 5H). ESI-MS:560[M+H$^+$].

Preparation of the Hydrochloride of Compound I-5

Compound I-5 (1 mmol) and 5% hydrochloric acid aqueous solution (1 mmol) were used as raw materials, and 0.48 g of white solid with a yield of 81% was obtained according to the synthetic method of the hydrochloride of compound I-1.

Element analysis: $C_{34}H_{49}N_5O_2 \cdot HCl$ (theoretical value %: C, 68.49; H, 8.45; N, 11.75; experimental value %: C, 68.38; H, 8.39; N, 11.86).

Preparation of the Trifluoroacetate of Compound I-5

Compound I-5 (1 mmol) and 5% trifluoroacetic acid aqueous solution (1 mmol) were used as raw materials, and 0.56 g of white solid with a yield of 83% was obtained according to the synthetic method of the hydrochloride of compound I-1.

Element analysis: $C_{34}H_{49}N_5O_2 \cdot CF_3CO_2H$ (theoretical value %: C, 64.17; H, 7.48; N, 10.39; experimental value %: C, 64.29; H, 7.27; N, 10.55).

Example 6

Preparation of N-((trans)-4-(2-(4-(6-morpholino-4-phenylpyridin-2-yl)piperazin-1-yl)ethyl)cyclohexyl) furan-2-carboxamide (I-6)

Intermediate 6-1 (5.0 mmol) and furan-2-carbonyl chloride (5.5 mmol) were used as raw materials, and 2.3 g of target compound I-6 as off-white solid with a yield of 85% was obtained according to the preparation method of compound I-1.

$^1$H NMR (CDCl$_3$, δ:ppm) δ 7.58-7.56 (m, 2H), 7.46-7.35 (m, 4H), 7.09 (d, J=3.4 Hz, 1H), 6.49 (dd, J=3.4, 1.8 Hz, 1H), 6.23 (s, 1H), 6.17 (d, J=10.5 Hz, 2H), 3.92-3.91 (m, 1H), 3.86-3.80 (m, 4H), 3.60 (brs, 4H), 3.55-3.49 (m, 4H), 2.58 (brs, 4H), 2.49-2.36 (m, 2H), 2.13-2.03 (m, 2H), 1.83 (d, J=12.6 Hz, 2H), 1.54-1.44 (m, 2H), 1.23-1.20 (m, 5H). ESI-MS:544[M+H$^+$].

Example 7

Preparation of 1,1-dimethyl-3-(trans-4-(2-(4-(6-morpholino-4-phenylpyridin-2-yl)piperazin-1-yl) ethyl)cyclohexyl)urea (I-7)

Intermediate 6-1 (5.0 mmol) and dimethylcarbamoyl chloride (5.5 mmol) were used as raw materials, and 2.0 g of target compound I-7 as white solid with a yield of 77% was obtained according to the preparation method of compound I-1.

$^1$H NMR (CDCl$_3$, δ:ppm) δ 7.54-7.53 (m, 2H), 7.48 (d, J=4.2 Hz, 2H), 7.38-7.37 (m, 2H), 7.10-7.08 (m, 1H), 6.27 (s, 2H), 3.89-3.87 (m, 1H), 3.86-3.80 (m, 4H), 3.61 (brs, 4H), 3.56-3.50 (m, 4H), 3.01 (s, 6H), 2.58 (brs, 4H), 2.50-2.37 (m, 2H), 2.14-2.05 (m, 2H), 1.87 (d, J=12.6 Hz, 2H), 1.55-1.45 (m, 2H), 1.24-1.22 (m, 5H). ESI-MS:521 [M+H$^+$].

Example 8

Preparation of N-(trans-4-(2-(4-(4-(4-fluorophenyl)-6-morpholinopyridin-2-yl)piperazin-1-yl)ethyl)cyclohexyl)benzamide (II-1)

trans-4-(2-(4-(4-(4-Fluorophenyl)-6-morpholinopyridin-2-yl)piperazin-1-yl)ethyl)cyclohexan-1-amine (intermediate 6-2, prepared according to the general synthetic method) (5.0 mmol) and benzoyl chloride (5.5 mmol) were used as raw materials, and 2.1 g of target compound II-1 as off-white solid with a yield of 73% was obtained according to the preparation method of compound I-1.

$^1$H NMR (CDCl$_3$, δ:ppm) δ 7.84-7.82 (m, 3H), 7.80 (dd, J=8.7, 5.6 Hz, 2H), 7.56-7.54 (m, 3H), 7.30 (d, J=8.7 Hz, 2H), 6.46 (s, 1H), 6.41 (s, 1H), 3.74-3.70 (m, 8H), 3.48-3.46 (m, 4H), 3.13 (brs, 4H), 2.97 (t, J=7.6 Hz, 2H), 1.75-1.73 (m, 4H), 1.56-1.55 (m, 2H), 1.21-1.19 (m, 3H), 1.07-0.91 (m, 2H). ESI-MS:572[M+H$^+$].

Example 9

Preparation of N-(trans-4-(2-(4-(4-(4-fluorophenyl)-6-morpholinopyridin-2-yl)piperazin-1-yl)ethyl)cyclohexyl)nicotinamide (II-2)

Intermediate 6-2 (5.0 mmol) and nicotinoyl chloride (5.5 mmol) were used as raw materials, and 2.4 g of target compound II-2 as white solid with a yield of 84% was obtained according to the preparation method of compound I-1.

$^1$H NMR (DMSO-d$_6$, δ:ppm) δ 8.13-8.11 (m, 3H), 7.78-7.76 (m, 3H), 7.64 (d, J=7.9 Hz, 1H), 7.30 (d, J=8.7 Hz, 2H), 6.48 (s, 1H), 6.43 (s, 1H), 3.76-3.62 (m, 8H), 3.51-3.49 (m, 4H), 3.16 (brs, 4H), 3.03 (t, J=7.6 Hz, 2H), 1.78-1.76 (m, 4H), 1.59-1.58 (m, 2H), 1.24-1.22 (m, 3H), 1.10-0.93 (m, 2H).

ESI-MS:573[M+H$^+$].

Example 10

Preparation of N-(trans-4-(2-(4-(4-(4-fluorophenyl)-6-morpholinopyridin-2-yl)piperazin-1-yl)ethyl)cyclohexyl)furan-2-carboxamide (II-3)

Intermediate 6-2 (5.0 mmol) and furan-2-carbonyl chloride (5.5 mmol) were used as raw materials, and 2.0 g of target compound II-3 as white solid with a yield of 71% was obtained according to the preparation method of compound I-1.

$^1$H NMR (DMSO-d$_6$, δ:ppm) δ 7.81 (dd, J=8.7, 5.6 Hz, 2H), 7.30-7.28 (m, 4H), 7.18 (d, J=7.9 Hz, 1H), 6.61-6.60 (m, 1H), 6.46 (s, 1H), 6.41 (s, 11H), 3.73-3.69 (m, 8H), 3.49-3.47 (m, 4H), 3.13 (brs, 4H), 3.00 (t, J=7.6 Hz, 2H), 1.75-1.73 (m, 4H), 1.56-1.55 (m, 2H), 1.21-1.19 (m, 3H), 1.07-0.90 (m, 2H). ESI-MS:562[M+H$^+$].

Example 11

Preparation of 1-(trans-4-(2-(4-(4-(4-fluorophenyl)-6-morpholinopyridin-2-yl)piperazin-1-yl)ethyl)cyclohexyl)-3-methylurea (II-4)

Intermediate 6-2 (5.0 mmol) and N-methylcarbamoyl chloride (5.5 mmol) were used as raw materials, and 2.2 g of target compound II-4 as off-white solid with a yield of 84% was obtained according to the preparation method of compound I-1.

$^1$H NMR (DMSO-d$_6$, δ:ppm) δ 7.90 (s, 1H), 7.80 (dd, J=8.7, 5.6 Hz, 2H), 7.29 (d, J=8.7 Hz, 2H), 6.45 (s, 11H), 6.40 (s, 11H), 5.86 (d, J=7.9 Hz, 11H), 3.72-3.68 (m, 8H), 3.47-3.45 (m, 4H), 3.12 (brs, 4H), 2.99 (t, J=7.6 Hz, 2H), 2.70 (s, 3H), 1.74-1.72 (m, 4H), 1.55-1.54 (m, 2H), 1.20-1.18 (m, 3H), 1.06-0.89 (m, 2H).

ESI-MS:525[M+H$^+$].

Example 12

Preparation of 3-(trans-4-(2-(4-(4-(4-fluorophenyl)-6-morpholinopyridin-2-yl)piperazin-1-yl)ethyl)cyclohexyl)-1,1-dimethylurea (II-5)

Intermediate 6-2 (5.0 mmol) and N,N-dimethylcarbamoyl chloride (5.5 mmol) were used as raw materials, and 1.9 g of target compound II-5 as white solid with a yield of 70% was obtained according to the preparation method of compound I-1.

$^1$H NMR (DMSO-d$_6$, δ:ppm) δ 7.79 (dd, J=8.7, 5.6 Hz, 2H), 7.29 (d, J=8.7 Hz, 2H), 6.45 (s, 1H), 6.40 (s, 1H), 5.87 (d, J=7.9 Hz, 1H), 3.72-3.68 (m, 8H), 3.47-3.45 (m, 4H), 3.12 (brs, 4H), 2.99 (t, J=7.6 Hz, 2H), 2.74 (s, 6H), 1.74-1.72 (m, 4H), 1.55-1.54 (m, 2H), 1.20-1.18 (m, 3H), 1.06-0.89 (m, 2H). ESI-MS:539[M+H$^+$].

Example 13

Preparation of 3-(trans-4-(2-(4-(4-(4-fluorophenyl)-6-morpholinopyridin-2-yl)piperazin-1-yl)ethyl)cyclohexyl)-1-methyl-1-propylurea (II-6)

Intermediate 6-2 (5.0 mmol), N-methyl-N-propanecarbonyl chloride (5.5 mmol) were used as raw materials, and 2.4 g of target compound II-6 as off-white solid with a yield of 85% was obtained according to the preparation method of compound I-1.

$^1$H NMR (DMSO-d$_6$, δ:ppm) δ 7.79 (dd, J=8.7, 5.6 Hz, 2H), 7.29 (d, J=8.7 Hz, 2H), 6.45 (s, 1H), 6.40 (s, 1H), 5.87 (d, J=7.9 Hz, 1H), 3.72-3.68 (m, 8H), 3.47-3.45 (m, 4H), 3.20 (t, J=7.6 Hz, 2H), 3.12 (brs, 4H), 3.10 (s, 6H), 2.99 (t, J=7.6 Hz, 2H), 1.74-1.72 (m, 4H), 1.63-1.61 (m, 2H), 1.55-1.54 (m, 2H), 1.20-1.18 (m, 3H), 1.06-0.89 (m, 2H), 0.86 (t, J=7.6 Hz, 2H).

ESI-MS:567[M+H$^+$].

Example 14

Preparation of N-(trans-4-(2-(4-(4-(4-methoxyphenyl)-6-morpholinopyridin-2-yl)piperazin-1-yl)ethyl)cyclohexyl)tetrahydropyrrole-1-carboxamide (III-1)

trans-4-(2-(4-(4-(4-Methoxyphenyl)-6-morpholinopyridin-2-yl)piperazin-1-yl)ethyl)cyclohexan-1-amine (intermediate 6-3, prepared according to the general synthetic method) (5.0 mmol) and pyrrolidine-1-carbonyl chloride (5.5 mmol) were used as raw materials, and 2.0 g of target compound III-1 as white solid with a yield of 71% was obtained according to the preparation method of compound I-1.

$^1$H NMR (DMSO-d$_6$, δ:ppm) δ 7.69 (d, J=8.7 Hz, 2H), 7.05-6.97 (m, 2H), 6.45 (s, 1H), 6.39 (s, 1H), 5.88 (d, J=7.8 Hz, 1H), 3.95-3.74 (m, 5H), 3.70-3.67 (m, 6H), 3.45-3.42 (m, 4H), 3.40-3.29 (m, 1H), 3.19 (brs, 4H), 3.15-3.12 (m, 4H), 3.07 (t, J=8.1 Hz, 2H), 1.84-1.82 (m, 4H), 1.74-1.72 (m, 4H), 1.63-1.49 (m, 2H), 1.20-1.18 (m, 3H), 0.98-0.96 (m, 2H). ESI-MS:577[M+H$^+$].

Example 15

Preparation of N-(trans-4-(2-(4-(4-(4-methoxyphenyl)-6-morpholinopyridin-2-yl)piperazin-1-yl)ethyl)cyclohexyl)morpholine-4-carboxamide (III-2)

Intermediate 6-3 (5.0 mmol) and morpholine-4-carbonyl chloride (5.5 mmol) were used as raw materials, and 2.7 g of target compound III-2 as off-white solid with a yield of 91% was obtained according to the preparation method of compound I-1.

$^1$H NMR (DMSO-d$_6$, δ:ppm) δ 7.70 (d, J=8.7 Hz, 2H), 7.06-6.98 (m, 2H), 6.46 (s, 1H), 6.40 (s, 1H), 5.87 (d, J=7.8 Hz, 1H), 3.95-3.74 (m, 5H), 3.70-3.67 (m, 6H), 3.60-3.68 (m, 4H), 3.45-3.42 (m, 4H), 3.35-3.34 (m, 4H), 3.40-3.29 (m, 1H), 3.19 (brs, 4H), 3.07 (t, J=8.1 Hz, 2H), 1.74-1.72 (m, 4H), 1.63-1.49 (m, 2H), 1.20-1.18 (m, 3H), 0.98-0.96 (m, 2H).

ESI-MS:593[M+H$^+$].

Example 16

Preparation of N-(trans-4-(2-(4-(4-(4-methoxyphenyl)-6-morpholinopyridin-2-yl)piperazin-1-yl)ethyl)cyclohexyl)piperidine-1-carboxamide (III-3)

Intermediate 6-3 (5.0 mmol) and piperidine-1-carbonyl chloride (5.5 mmol) were used as raw materials, and 2.1 g of target compound III-3 as off-white solid with a yield of 71% was obtained according to the preparation method of compound I-1.

$^1$H NMR (DMSO-d$_6$, δ:ppm) δ 7.69 (d, J=8.7 Hz, 2H), 7.05-6.97 (m, 2H), 6.45 (s, 1H), 6.39 (s, 1H), 5.88 (d, J=7.8 Hz, 1H), 3.93-3.72 (m, 9H), 3.69-3.66 (m, 6H), 3.44-3.41 (m, 4H), 3.39-3.28 (m, 11H), 3.18 (brs, 4H), 3.06 (t, J=8.1 Hz, 2H), 1.75-1.71 (m, 8H), 1.64-1.50 (m, 4H), 1.18-1.16 (m, 3H), 0.97-0.95 (m, 2H). ESI-MS:591[M+H$^+$].

Example 17

Preparation of N-(trans-4-(2-(4-(4-(4-methoxyphenyl)-6-morpholinopyridin-2-yl)piperazin-1-yl)ethyl)cyclohexyl)-4-methylpiperazine-1-carboxamide (III-4)

Intermediate 6-3 (5.0 mmol) and 4-methylpiperazine-1-carbonyl chloride (5.5 mmol) were used as raw materials, and 2.6 g of target compound III-4 as off-white solid with a yield of 86% was obtained according to the preparation method of compound I-1.

$^1$H NMR (DMSO-d$_6$, δ:ppm) δ 7.69 (d, J=8.7 Hz, 2H), 7.05-6.97 (m, 2H), 6.45 (s, 11H), 6.39 (s, 11H), 5.88 (d, J=7.8 Hz, 1H), 3.95-3.74 (m, 5H), 3.70-3.67 (m, 6H), 3.45-3.42 (m, 4H), 3.39-3.29 (m, 5H), 3.19 (brs, 4H), 3.07 (t, J=8.1 Hz, 2H), 2.32-2.30 (m, 4H), 2.22 (s, 3H), 1.74-1.72 (m, 4H), 1.63-1.49 (m, 2H), 1.20-1.18 (m, 3H), 0.98-0.96 (m, 2H). ESI-MS:606[M+H$^+$].

Example 18

Preparation of N-(trans-4-(2-(4-(6'-morpholino-[2,4'-bipyridin]-2'-yl)piperazin-1-yl)ethyl)cyclohexyl)propionamide (IV-1)

trans-4-(2-(4-(6'-Morpholino-[3,4'-bipyridin]-2'-yl)piperazin-1-yl)ethyl)cyclohexan-1-amine (intermediate 6-4, prepared according to the general synthetic method) (5.0 mmol) and pyridine-2-carbonyl chloride (5.5 mmol) were used as raw materials, and 1.9 g of target compound IV-1 as off-white solid with a yield of 75% was obtained according to the preparation method of compound I-1.

$^1$H NMR (DMSO-d$_6$, δ:ppm) δ 8.94 (dd, J=2.4, 0.8 Hz, 1H), 8.62 (dd, J=4.8, 1.6 Hz, 1H), 8.13 (dt, J=8.0, 1.9 Hz, 1H), 7.52-7.44 (m, 1H), 6.53 (s, 1H), 6.47 (s, 1H), 5.87 (d, J=7.8 Hz, 1H), 3.71-3.69 (m, 8H), 3.49-3.47 (m, 4H), 3.38-3.30 (m, 1H), 3.10 (brs, 4H), 2.97 (t, J=7.6 Hz, 2H), 2.35 (q, J=7.6 Hz, 2H), 1.75-1.73 (m, 4H), 1.53-1.52 (m, 2H), 1.20-1.18 (m, 3H), 1.05 (t, J=7.6 Hz, 3H), 0.98-0.96 (m, 2H).

ESI-MS:507[M+H$^+$].

Example 19

Preparation of N-(trans-4-(2-(4-(6'-morpholino-[2,4'-bipyridin]-2'-yl)piperazin-1-yl)ethyl)cyclohexyl)furan-2-carboxamide (IV-2) and the salt thereof Intermediate 6-4 (5.0 mmol) and furan-2-carbonyl chloride (5.5 mmol) were used as raw materials, and 2.3 g of target compound IV-2 as white solid with a yield of 85% was obtained according to the preparation method of compound I-1.

$^1$H NMR (DMSO-d$_6$, δ:ppm) δ 8.95 (dd, J=2.4, 0.8 Hz, 1H), 8.61 (dd, J=4.8, 1.6 Hz, 1H), 8.14 (dt, J=8.0, 1.9 Hz, 1H), 7.53-7.45 (m, 1H), 7.22-7.20 (m, 3H), 6.60-6.59 (m, 1H), 6.53 (s, 1H), 6.47 (s, 1H), 3.71-3.69 (m, 8H), 3.49-3.47 (m, 4H), 3.38-3.30 (m, 1H), 3.10 (brs, 4H), 2.97 (t, J=7.6 Hz, 2H), 1.75-1.73 (m, 4H), 1.53-1.52 (m, 2H), 1.20-1.18 (m, 3H), 0.98-0.96 (m, 2H).

ESI-MS:545[M+H$^+$].

Preparation of the Hydrochloride of Compound IV-2

Compound IV-2 (1 mmol), 5% hydrochloric acid aqueous solution (1 mmol) were used as raw materials, and 0.49 g of white solid with a yield of 84% was obtained according to the preparation method of the hydrochloride of compound I-1.

Element analysis: C$_{31}$H$_{40}$N$_6$O$_3$·HCl (theoretical value %: C, 64.07; H, 7.11; N, 14.46; experimental value %: C, 64.21; H, 7.00; N, 14.69).

Example 20

Preparation of 1,1-dimethyl-3-(trans-4-(2-(4-(6'-morpholino-[2,4'-bipyridin]-2'-yl)piperazin-1-yl)ethyl)cyclohexyl)urea (IV-3)

Intermediate 6-4 (5.0 mmol) and dimethylcarbamoyl chloride (5.5 mmol) were used as raw materials, and 2.1 g of target compound IV-3 as white solid with a yield of 81% was obtained according to the preparation method of compound I-1.

$^1$H NMR (DMSO-d$_6$, δ:ppm) δ 8.95 (dd, J=2.4, 0.8 Hz, 1H), 8.61 (dd, J=4.8, 1.6 Hz, 1H), 8.14 (dt, J=8.0, 1.9 Hz, 1H), 7.53-7.45 (m, 1H), 6.53 (s, 1H), 6.47 (s, 1H), 5.87 (d, J=7.8 Hz, 1H), 3.71-3.69 (m, 8H), 3.49-3.47 (m, 4H), 3.38-3.30 (m, 1H), 3.10 (brs, 4H), 2.97 (t, J=7.6 Hz, 2H), 2.74 (s, 6H), 1.75-1.73 (m, 4H), 1.53-1.52 (m, 2H), 1.20-1.18 (m, 3H), 0.98-0.96 (m, 2H). ESI-MS:522[M+H$^+$].

Example 21

Preparation of 1,1-diisopropyl-3-(trans-4-(2-(4-(6'-morpholino-[2,4'-bipyridin]-2'-yl)piperazin-1-yl)ethyl)cyclohexyl)urea (IV-4)

Intermediate 6-4 (5.0 mmol) and diisopropylcarbamoyl chloride (5.5 mmol) were used as raw materials, and 2.0 g of target compound IV-4 as white solid with a yield of 69% was obtained according to the preparation method of compound I-1.

$^1$H NMR (DMSO-d$_6$, δ:ppm) δ 8.95 (dd, J=2.4, 0.8 Hz, 1H), 8.61 (dd, J=4.8, 1.6 Hz, 1H), 8.14 (dt, J=8.0, 1.9 Hz, 1H), 7.53-7.45 (m, 1H), 6.53 (s, 1H), 6.47 (s, 1H), 5.87 (d, J=7.8 Hz, 1H), 3.91-3.90 (m, 2H), 3.71-3.69 (m, 8H), 3.49-3.47 (m, 4H), 3.38-3.30 (m, 1H), 3.10 (brs, 4H), 2.97 (t, J=7.6 Hz, 2H), 1.75-1.73 (m, 4H), 1.53-1.52 (m, 2H), 1.45-1.42 (m, 12H), 1.20-1.18 (m, 3H), 0.98-0.96 (m, 2H). ESI-MS:578[M+H$^+$].

Example 22

Preparation of N-(trans-4-(2-(4-(4-(furan-2-yl)-6-morpholinopyridin-2-yl)piperazin-1-yl)ethyl)cyclohexyl)acetamide (V-1)

trans-4-(2-(4-(4-(Furan-2-yl)-6-morpholinopyridin-2-yl)piperazin-1-yl)ethyl)cyclohexan-1-amine (intermediate 6-5, prepared according to the general synthetic method) (5.0 mmol) and acetyl chloride (5.5 mmol) were used as raw materials, and 2.1 g of target compound V-1 as white solid with a yield of 87% was obtained according to the preparation method of compound I-1.

$^1$H NMR (DMSO-d$_6$, δ:ppm) δ 7.79 (d, J=1.7 Hz, 1H), 7.16 (d, J=3.4 Hz, 1H), 6.63 (dd, J=3.4, 1.8 Hz, 1H), 6.49-6.47 (m, 2H), 5.90 (d, J=7.8 Hz, 1H), 3.71-3.69 (m, 8H), 3.45-3.43 (m, 4H), 3.36-3.32 (m, 1H), 3.11 (brs, 4H), 2.98 (t, J=7.6 Hz, 2H), 2.01 (s, 3H), 1.74-1.72 (m, 4H), 1.55-1.54 (m, 2H), 1.20-1.18 (m, 3H), 0.98-0.96 (m, 2H). ESI-MS:482[M+H$^+$].

Example 23

Preparation of N-(trans-4-(2-(4-(4-(furan-2-yl)-6-morpholinopyridin-2-yl)piperazin-1-yl)ethyl)cyclohexyl)-2-methoxyacetamide (V-2)

Intermediate 6-5 (5.0 mmol) and 2-methoxyacetyl chloride (5.5 mmol) were used as raw materials, and 2.2 g of target compound V-2 as white solid with a yield of 86% was obtained according to the preparation method of compound I-1.

$^1$H NMR (DMSO-d$_6$, δ:ppm) δ 7.78 (d, J=1.7 Hz, 1H), 7.15 (d, J=3.4 Hz, 1H), 6.63 (dd, J=3.4, 1.8 Hz, 1H), 6.49-6.47 (m, 2H), 5.96 (d, J=7.8 Hz, 1H), 4.46 (s, 2H), 3.70-3.68 (m, 8H), 3.44-3.42 (m, 4H), 3.45 (s, 3H), 3.36-3.32 (m, 1H), 3.11 (brs, 4H), 2.98 (t, J=7.6 Hz, 2H), 1.74-1.72 (m, 4H), 1.55-1.54 (m, 2H), 1.20-1.18 (m, 3H), 0.98-0.96 (m, 2H). ESI-MS:512[M+H$^+$].

Example 24

Preparation of 3-(trans-4-(2-(4-(4-(furan-2-yl)-6-morpholinopyridin-2-yl)piperazin-1-yl)ethyl)cyclohexyl)-1,1-dimethylurea (V-3)

Intermediate 6-5 (5.0 mmol) and dimethylcarbamoyl chloride (5.5 mmol) were used as raw materials, and 2.1 g of target compound V-3 as white solid with a yield of 82% was obtained according to the preparation method of compound I-1.

$^1$H NMR (DMSO-d$_6$, δ:ppm) δ 7.78 (d, J=1.7 Hz, 1H), 7.15 (d, J=3.4 Hz, 1H), 6.63 (dd, J=3.4, 1.8 Hz, 11H), 6.49-6.47 (m, 2H), 5.87 (d, J=7.8 Hz, 1H), 3.70-3.68 (m, 8H), 3.44-3.42 (m, 4H), 3.36-3.32 (m, 1H), 3.11 (brs, 4H), 2.98 (t, J=7.6 Hz, 2H), 2.74 (s, 6H), 1.74-1.72 (m, 4H), 1.55-1.54 (m, 2H), 1.20-1.18 (m, 3H), 0.98-0.96 (m, 2H). ESI-MS:511[M+H$^+$].

Example 25

Preparation of N-(trans-4-(2-(4-(4-(furan-2-yl)-6-morpholinopyridin-2-yl)piperazin-1-yl)ethyl)cyclohexyl)piperidine-1-carboxamide (V-4) and the salt thereof Intermediate 6-5 (5.0 mmol) and piperidine-1-carbonyl chloride (5.5 mmol) were used as raw materials, and 2.4 g of target compound V-4 as white solid with a yield of 87% was obtained according to the preparation method of compound I-1.

$^1$H NMR (DMSO-d$_6$, δ:ppm) δ 7.77 (d, J=1.7 Hz, 1H), 7.14 (d, J=3.4 Hz, 1H), 6.62 (dd, J=3.4, 1.8 Hz, 1H), 6.48-6.46 (m, 2H), 5.87 (d, J=7.8 Hz, 1H), 3.92-3.88 (m, 4H), 3.70-3.68 (m, 8H), 3.44-3.42 (m, 4H), 3.36-3.32 (m, 1H), 3.11 (brs, 4H), 2.98 (t, J=7.6 Hz, 2H), 1.82-1.80 (m, 4H), 1.74-1.72 (m, 4H), 1.62-1.60 (m, 2H), 1.55-1.54 (m, 2H), 1.20-1.18 (m, 3H), 0.99-0.97 (m, 2H). ESI-MS:551 [M+H$^+$].

Preparation of the Hydrobromide of Compound V-4

Compound V-4 (1 mmol) and 5% hydrobromic acid aqueous solution (1 mmol) were used as raw materials, and 0.5 g of white solid with a yield of 79% was obtained according to the preparation method of the hydrochloride of compound I-1.

Element analysis: C$_{31}$H$_{46}$N$_6$O$_3$·HBr (theoretical value %: C, 58.95; H, 7.50; N, 13.30; experimental value %: C, 58.79; H, 7.58; N, 13.47).

Preparation of the Sulfate of Compound V-4

Compound V-4 (1 mmol) and 5% sulfuric acid (0.5 mmol) were used as raw materials, and 0.28 g of white solid with a yield of 60% was obtained according to the preparation method of the hydrochloride of compound I-1.

Element analysis: C$_{31}$H$_{46}$N$_6$O$_3$·½H$_2$SO$_4$ theoretical value %: C, 62.08; H, 7.90; N, 14.01; experimental value %: C, 62.30; H, 7.72; N, 14.14).

Example 26

Preparation of N-(trans-4-(2-(4-(4-(furan-2-yl)-6-morpholinopyridin-2-yl)piperazin-1-yl)ethyl)cyclohexyl)morpholine-4-carboxamide (V-5)

Intermediate 6-5 (5.0 mmol) and morpholine-4-carbonyl chloride (5.5 mmol) were used as raw materials, and 2.4 g of target compound V-5 as white solid with a yield of 87% was obtained according to the preparation method of compound I-1.

$^1$H NMR (DMSO-d$_6$, δ:ppm) δ 7.78 (d, J=1.7 Hz, 1H), 7.15 (d, J=3.4 Hz, 1H), 6.63 (dd, J=3.4, 1.8 Hz, 1H), 6.49-6.47 (m, 2H), 5.87 (d, J=7.8 Hz, 1H), 3.70-3.68 (m, 8H), 3.59-3.56 (m, 4H), 3.44-3.42 (m, 4H), 3.37-3.31 (m, 5H), 3.11 (brs, 4H), 2.98 (t, J=7.6 Hz, 2H), 1.74-1.72 (m, 4H), 1.55-1.54 (m, 2H), 1.20-1.18 (m, 3H), 0.98-0.96 (m, 2H). ESI-MS:553[M+H*].

Example 27

Preparation of N-(trans-4-(2-(4-(6-morpholino-4-(thiophen-2-yl)pyridin-2-yl)piperazin-1-yl)ethyl)cyclohexyl)acetamide (VI-1)

trans-4-(2-(4-(4-(Thiophen-2-yl)-6-morpholinopyridin-2-yl)piperazin-1-yl)ethyl)cyclohexan-1-amine (intermediate 6-6, prepared according to the general synthetic method) (5.0 mmol) and acetyl chloride (5.5 mmol) were used as raw materials, and 2.2 g of target compound VI-1 as white solid with a yield of 88% was obtained according to the preparation method of compound I-1.

$^1$H NMR (DMSO-d$_6$, δ:ppm) δ 7.82 (d, J=1.7 Hz, 1H), 7.44 (d, J=3.4 Hz, 1H), 6.73 (dd, J=3.4, 1.8 Hz, 1H), 6.49-6.47 (m, 2H), 5.97 (d, J=7.8 Hz, 1H), 3.75-3.73 (m, 8H), 3.49-3.47 (m, 4H), 3.40-3.36 (m, 1H), 3.15 (brs, 4H), 3.02 (t, J=7.6 Hz, 2H), 2.01 (s, 3H), 1.76-1.74 (m, 4H), 1.57-1.56 (m, 2H), 1.22-1.20 (m, 3H), 1.01-0.99 (m, 2H). ESI-MS:498[M+H$^+$].

Example 28

Preparation of N-(trans-4-(2-(4-(6-morpholino-4-(thiophen-2-yl)pyridin-2-yl)piperazin-1-yl)ethyl)cyclohexyl)cyclopropanecarboxamide (VI-2)

Intermediate 6-6 (5.0 mmol) and cyclopropanecarbonyl chloride (5.5 mmol) were used as raw materials, and 2.4 g of target compound VI-2 as white solid with a yield of 92% was obtained according to the preparation method of compound I-1.

$^1$H NMR (Chloroform-d, δ:ppm) δ 7.82 (d, J=1.7 Hz, 1H), 7.44 (d, J=3.4 Hz, 1H), 6.73 (dd, J=3.4, 1.8 Hz, 1H), 6.49-6.47 (m, 2H), 5.95 (d, J=7.8 Hz, 1H), 3.75-3.73 (m, 8H), 3.49-3.47 (m, 4H), 3.40-3.36 (m, 1H), 3.15 (brs, 4H), 3.02 (t, J=7.6 Hz, 2H), 1.76-1.74 (m, 4H), 1.57-1.54 (m, 3H), 1.22-1.20 (m, 3H), 1.01-0.99 (m, 2H), 0.81-0.79 (m, 2H), 0.60-0.58 (m, 2H). ESI-MS:524[M+H$^+$].

Example 29

Preparation of N-(trans-4-(2-(4-(6-morpholino-4-(thiophen-2-yl)pyridin-2-yl)piperazin-1-yl)ethyl)cyclohexyl)nicotinamide (VI-3) and the salt thereof Intermediate 6-6 (5.0 mmol) and nicotinoyl chloride (5.5 mmol) were used as raw materials, and 1.9 g of target compound VI-3 as white solid with a yield of 68% was obtained according to the preparation method of compound I-1.

$^1$H NMR ((CDCl$_3$, δ:ppm) δ 8.87 (dd, J=2.4, 1.2 Hz, 1H) 8.56-8.55 (m, 1H), 8.16 (dd, J=7.6, 2.4 Hz, 1H), 7.83-7.81 (m, 2H), 7.46-7.44 (m, 2H), 6.73 (dd, J=3.4, 1.8 Hz, 1H), 6.49-6.47 (m, 2H), 3.75-3.73 (m, 8H), 3.49-3.47 (m, 4H), 3.40-3.36 (m, 1H), 3.15 (brs, 4H), 3.02 (t, J=7.6 Hz, 2H), 1.76-1.74 (m, 4H), 1.57-1.56 (m, 2H), 1.22-1.20 (m, 3H), 1.01-0.99 (m, 2H).
ESI-MS:561[M+H$^+$].

Preparation of the Hydrochloride of Compound VI-3

Compound VI-3 (1 mmol) and 5% hydrochloric acid aqueous solution (1 mmol) were used as raw materials, and 0.48 g of white solid with a yield of 80% was obtained according to the preparation method of the hydrochloride of compound I-1.

Element analysis: $C_{31}H_{40}N_6O_2S \cdot HCl$ (theoretical value %: C, 62.35; H, 6.92; N, 14.07; experimental value %: C, 62.45; H, 6.55; N, 14.26).

Preparation of the Trifluoroacetate of Compound VI-3

Compound VI-3 (1 mmol) and 5% trifluoroacetic acid aqueous solution (1 mmol) were used as raw materials, and 0.57 g of white solid with a yield of 85% was obtained according to the preparation method of the hydrochloride of compound I-1.

Element analysis: $C_{31}H_{40}N_6O_2S \cdot CF_3CO_2H$ (theoretical value %: C, 58.74; H, 6.12; N, 12.45; experimental value %: C, 58.59; H, 6.34; N, 12.66).

Example 30

Preparation of 1,1-dimethyl-3-(trans-4-(2-(4-(6-morpholino-4-(thiophen-2-yl)pyridin-2-yl)piperazin-1-yl)ethyl)cyclohexyl)urea (VI-4)

Intermediate 6-6 (5.0 mmol) and dimethylcarbamoyl chloride (5.5 mmol) were used as raw materials, and 1.8 g of target compound VI-4 as white solid with a yield of 68% was obtained according to the preparation method of compound I-1.

$^1$H NMR (CDCl$_3$, δ:ppm) δ 7.83 (d, J=1.7 Hz, 1H), 7.46 (d, J=3.4 Hz, 1H), 6.75 (dd, J=3.4, 1.8 Hz, 1H), 6.49-6.47 (m, 2H), 5.93 (d, J=7.8 Hz, 1H), 3.75-3.73 (m, 8H), 3.49-3.47 (m, 4H), 3.40-3.36 (m, 1H), 3.15 (brs, 4H), 3.02 (t, J=7.6 Hz, 2H), 2.71 (s, 6H), 1.76-1.74 (m, 4H), 1.57-1.56 (m, 2H), 1.22-1.20 (m, 3H), 1.01-0.99 (m, 2H). ESI-MS: 527[M+H$^+$].

Example 31

Preparation of N-(trans-4-(2-(4-(6-morpholino-4-(thiophen-2-yl)pyridin-2-yl)piperazin-1-yl)ethyl)cyclohexyl)tetrahydropyrrole-1-carboxamide (VI-5)

Intermediate 6-6 (5.0 mmol) and pyrroline-4-carbonyl chloride (5.5 mmol) were used as raw materials, and 2.0 g of target compound VI-5 as white solid with a yield of 72% was obtained according to the preparation method of compound I-1.

$^1$H NMR (CDCl$_3$, δ:ppm) δ 7.82 (d, J=1.7 Hz, 1H), 7.44 (d, J=3.4 Hz, 1H), 6.73 (dd, J=3.4, 1.8 Hz, 1H), 6.49-6.47 (m, 2H), 5.97 (d, J=7.8 Hz, 1H), 3.75-3.73 (m, 8H), 3.49-3.47 (m, 4H), 3.40-3.36 (m, 1H), 3.31-3.29 (m, 4H), 3.15 (brs, 4H), 3.02 (t, J=7.6 Hz, 2H), 1.78-1.74 (m, 8H), 1.57-1.56 (m, 2H), 1.22-1.20 (m, 3H), 1.00-0.98 (m, 2H). ESI-MS:553[M+H$^+$].

Example 32

Preparation of N-(trans-4-(2-(4-(6-morpholino-4-(1H-pyrrol-2-yl)pyridin-2-yl)piperazin-1-yl)ethyl)cyclohexyl)propionamide (VII-1)

trans-4-(2-(4-(4-(Pyrrol-2-yl)-6-morpholinopyridin-2-yl)piperazin-1-yl)ethyl)cyclohexan-1-amine (intermediate 6-7, prepared according to the general synthetic method) (5.0 mmol) and propionyl chloride (5.5 mmol) were used as raw materials, and 2.1 g of target compound VII-1 as white solid with a yield of 85% was obtained according to the preparation method of compound I-1.

$^1$H NMR (DMSO-d$_6$, δ:ppm) δ 12.02 (brs, 1H), 7.02 (d, J=1.7 Hz, 1H), 6.89 (d, J=3.4 Hz, 1H), 6.43 (dd, J=3.4, 1.8 Hz, 1H), 6.26-6.24 (m, 2H), 5.85 (d, J=7.8 Hz, 1H), 3.71-3.69 (m, 8H), 3.45-3.43 (m, 4H), 3.37-3.33 (m, 1H), 3.12 (brs, 4H), 2.99 (t, J=7.6 Hz, 2H), 2.35 (q, J=7.6 Hz, 2H), 1.75-1.73 (m, 4H), 1.56-1.55 (m, 2H), 1.21-1.19 (m, 3H), 1.01-0.97 (m, 5H). ESI-MS:495[M+H$^+$].

Example 33

Preparation of N-(trans-4-(2-(4-(6-morpholino-4-(1H-pyrrol-2-yl)pyridin-2-yl)piperazin-1-yl)ethyl)cyclohexyl)furan-2-carboxamide (VII-2)

Intermediate 6-7 (5.0 mmol) and furan-2-carbonyl chloride (5.5 mmol) were used as raw materials, and 1.9 g of target compound VII-2 as white solid with a yield of 71% was obtained according to the preparation method of compound I-1.

$^1$H NMR (DMSO-d$_6$, δ:ppm) δ 12.02 (brs, 1H), 7.25-7.23 (m, 2H), 7.20 (d, J=7.8 Hz, 1H), 7.02 (d, J=1.7 Hz, 1H), 6.89-6.87 (m, 2H), 6.43 (dd, J=3.4, 1.8 Hz, 1H), 6.26-6.24 (m, 2H), 3.71-3.69 (m, 8H), 3.45-3.43 (m, 4H), 3.37-3.33 (m, 1H), 3.12 (brs, 4H), 2.98 (t, J=7.6 Hz, 2H), 1.75-1.73 (m, 4H), 1.56-1.55 (m, 2H), 1.21-1.19 (m, 3H), 0.99-0.98 (m, 2H). ESI-MS:533[M+H$^+$].

Example 34

Preparation of N-(trans-4-(2-(4-(6-morpholino-4-(1H-pyrrol-2-yl)pyridin-2-yl)piperazin-1-yl)ethyl)cyclohexyl)cyclohexanecarboxamide (VII-3)

Intermediate 6-7 (2.0 mmol) and cyclohexanecarbonyl chloride (2.4 mmol) were used as raw materials, and 0.8 g of target compound VII-3 as white solid with a yield of 73% was obtained according to the preparation method of compound I-1.

$^1$H NMR (DMSO-d$_6$, δ:ppm) δ 12.02 (brs, 1H), 7.02 (d, J=1.7 Hz, 1H), 6.89 (d, J=3.4 Hz, 1H), 6.43 (dd, J=3.4, 1.8 Hz, 1H), 6.26-6.24 (m, 2H), 5.85 (d, J=7.8 Hz, 1H), 3.71-3.69 (m, 8H), 3.45-3.43 (m, 4H), 3.37-3.33 (m, 1H), 3.12 (brs, 4H), 2.99 (t, J=7.6 Hz, 2H), 2.48-2.46 (m, 1H), 1.75-1.70 (m, 6H), 1.56-1.55 (m, 2H), 1.51-1.41 (m, 8H), 1.21-1.19 (m, 3H), 0.98-0.96 (m, 2H). ESI-MS:549[M+H$^+$].

Example 35

Preparation of 1,1-dimethyl-3-(trans-4-(2-(4-(6-morpholino-4-(1H-pyrrol-2-yl)pyridin-2-yl)piperazin-1-yl)ethyl)cyclohexyl)urea (VII-4)

Intermediate 6-7 (2.0 mmol) and dimethylcarbamoyl chloride (2.4 mmol) were used as raw materials, and 0.8 g of target compound VII-4 as white solid with a yield of 78% was obtained according to the preparation method of compound I-1.

$^1$H NMR (DMSO-d$_6$, δ:ppm) δ 12.02 (brs, 1H), 7.03 (d, J=1.7 Hz, 1H), 6.90 (d, J=3.4 Hz, 1H), 6.44 (dd, J=3.4, 1.8 Hz, 1H), 6.27-6.25 (m, 2H), 5.86 (d, J=7.8 Hz, 1H), 3.71-3.69 (m, 8H), 3.45-3.43 (m, 4H), 3.37-3.33 (m, 1H), 3.12 (brs, 4H), 2.99 (t, J=7.6 Hz, 2H), 2.74 (s, 6H), 1.75-1.73 (m, 4H), 1.56-1.55 (m, 2H), 1.21-1.19 (m, 3H), 0.99-0.97 (m, 2H). ESI-MS:510[M+H$^+$].

Example 36

Preparation of N-(trans-4-(2-(4-(6-morpholino-4-(1H-pyrrol-2-yl)pyridin-2-yl)piperazin-1-yl)ethyl)cyclohexyl)piperidine-1-carboxamide (VII-5) and the salts thereof Intermediate 6-7 (2.0 mmol) and piperidine-1-carbonyl chloride (2.4 mmol) were used as raw materials, and 0.9 g of target compound VII-5 as white solid with a yield of 82% was obtained according to the preparation method of compound I-1.

$^1$H NMR (DMSO-d$_6$, δ:ppm) δ 12.02 (brs, 1H), 7.03 (d, J=1.7 Hz, 1H), 6.90 (d, J=3.4 Hz, 1H), 6.44 (dd, J=3.4, 1.8 Hz, 1H), 6.27-6.25 (m, 2H), 5.86 (d, J=7.8 Hz, 1H), 3.71-3.69 (m, 8H), 3.62-3.60 (m, 4H), 3.45-3.43 (m, 4H), 3.37-3.33 (m, 1H), 3.12 (brs, 4H), 2.99 (t, J=7.6 Hz, 2H), 1.75-1.73 (m, 4H), 1.56-1.51 (m, 6H), 1.39-1.37 (m, 2H), 1.21-1.19 (m, 3H), 0.99-0.97 (m, 2H). ESI-MS:550[M+H$^+$].

Preparation of the Hydrobromide of Compound VII-5

Compound VII-5 (1.0 mmol) and 5% hydrobromic acid aqueous solution (1.0 mmol) were used as raw materials, and 0.51 g of white solid with a yield of 81% was obtained according to the preparation method of the hydrochloride of compound I-1.

Element analysis: $C_{31}H_{47}N_7O_2 \cdot HBr$ (theoretical value %: C, 59.04; H, 7.67; N, 15.55; experimental value %: C, 59.18; H, 7.82; N, 15.31).

Example 37

1. Tablet:

All of the compounds in the examples of the present disclosure 20 mg

Sucrose 150 mg

Corn starch 27 mg

Magnesium stearate 3 mg

Preparation method: The active ingredients were mixed with sucrose and corn starch, and then water was added thereto for moistening. The mixture was stirred evenly, dried, crushed and sieved, and magnesium stearate was added thereto, and then the mixture was mixed evenly, and pressed into tablets. 200 mg of each tablet was weighed and contained 20 mg of active ingredient.

Example 38

2. Injection:

All of the compounds in the examples of the present disclosure 2 mg

Water for injection 98 mg

Preparation method: The active ingredient was dissolved in water for injection, mixed evenly, filtered, and the obtained solution was sub-packed in ampoule bottle under sterile conditions with 10 mg in each bottle, and the active ingredient content was 0.2 mg/bottle.

Example 39

Dopamine D$_2$ Receptor Binding Test

1. Experimental Materials (1) Transfection of D$_2$ Receptor Cells:

In this experiment, HEK293 cells were transfected with plasmid vector containing D$_2$ receptor protein gene, and calcium phosphate transfection method was used and after transfection, the cells were cultured in a culture solution containing G418, and the cell monoclonal and radioligand binding experiments were selected, and finally a stable cell line which could stably express D$_2$ receptor protein was obtained.

(2) Receptor Binding Experimental Materials:

Isotope ligand [$^3$H]Spiperone (113.0 Ci/mmol); purchased from Sigma company; (+)spiperone, purchased from RBI company; GF/B glass fiber filter paper, purchased from Whatman company; Tris imported and sub-packed; PPO, POPOP purchased from Shanghai Reagent No. 1 Factory; lipid-soluble scintillation fluid. Beckman LS-6500 multi-functional liquid scintillation counter.

2. Experimental Method:
(1) Cells:

HeK-293 cells were infected with recombinant viruses containing the above various genes respectively, and after 48-72 hours, the receptor proteins were expressed in large quantities on the membrane, and the cells were centrifuged at 1000 rpm for 5 min and then the culture solution was discarded, and the cells were collected, and stored in a −20° C. refrigerator for later use. Tris-HCl reaction buffer (pH=7.5) was used to resuspend in the experiment.

(2) Receptor Competitive Binding Experiment:

20 µL of the test compound, 20 µL of the radioactive ligand and 160 µL of the receptor protein were added to the reaction tube, so that the final concentration of the test compound and the positive drug cariprazine were both, and after incubation for 50 min in a 30° C. water bath, and the mixture was immediately transferred to an ice bath to terminate the reaction. On the Millipore cell sample collector, the mixture was quickly filtered under reduced pressure through GF/C glass fiber filter paper, and eluted with 3 mL of eluent (50 mMTris-HCl, pH 7.5) for 3 times, then dried under microwave for 5 to 6 min. The filter paper was moved into a 0.5 mL centrifuge tube, and 500 µL of lipid-soluble scintillation solution was added. The mixture was kept in the dark for more than 30 min, and the radioactivity intensity was determined by counting. The inhibition rate percentage of each compound to isotopic ligand binding was calculated according to the following formula:

Inhibition rate ($I\%$)=(total binding tube CPM−compound CPM)/(total binding tube CPM−non-specific binding tube CPM)×100%.

Two replicate tubes were made for each experiment of compound, and two separate experiments were performed.

The inhibition rate of the all compounds of the present disclosure was higher than 95%, and receptor binding tests in a series of concentrations were then performed on the compound of the present disclosure to determine the half inhibition amount ($IC_{50}$, concentration of compound required to inhibit 50% [$^3$H] Spiperone binding to $D_2$ receptor). Two tubes were tested for each concentration and two independent tests were performed for each compound.

$Ki=IC_{50}/(1+[L]/K_D)$ (Ki: affinity of the drug and the receptor, L: concentration of radioactive ligands, $K_D$: affinity value of the radioactive ligand and the receptor)

$D_2$ receptor binding test results of the compound of the present disclosure are shown in table 1. The test results in table 1 show that the compound of the present disclosure has strong or moderate affinity for dopamine $D_2$ receptor.

Example 40

Dopamine $D_3$ Receptor Binding Test

The experimental method was performed with reference to Journal of Pharmacology and Experimental Therapeutics 2010, 333(1): 328. [$^3$H]methyl-spiperone (0.3 nM) was used as the ligand, and (+)-butaclamol (10 µM) was used to determine the non-specific binding, and the binding assay was performed on human recombinant $D_3$ receptor (expressed in CHO cells).

$D_3$ receptor binding test results of the compound of the present disclosure are shown in table 1. It can be seen from table 1 that the compounds of the present disclosure all have strong affinity for $D_3$ receptors, which are comparable to the positive drug cariprazine, and combined with the results of example 39, this series of compounds also have appropriate selectivity for $D_3/D_2$ receptor, that is, the selectivity is between 10 and 60 times.

Example 41

5-$HT_{2A}$ Receptor Binding Test
1. Experimental Materials
(1) Transfection of 5-$HT_{2A}$ Cell:

In this experiment, HEK293 cells were transfected with plasmid vector containing 5-$HT_{2A}$ receptor protein gene, and calcium phosphate transfection method was used and after transfection, the cells were cultured in a culture solution containing G418, and the cell monoclonal and radioligand binding experiments were selected, and finally a stable cell line which could stably express 5-$HT_{2A}$ receptor protein was obtained.

(2) Receptor Binding Experimental Materials:

Isotope ligand [$^3$H]-Ketanserin (67.0 Ci/mmol); purchased from PerkinElmer company; (+)spiperone, purchased from RBI company; GF/B glass fiber filter paper, purchased from Whatman company; Tris imported and sub-packed; PPO, POPOP purchased From Shanghai Reagent No. 1 Factory; lipid-soluble scintillation fluid. Beckman LS-6500 multifunctional liquid scintillation counter.

2. Experimental Method

HeK-293 cells were infected with recombinant viruses containing the above various genes respectively, and after 48-72 hours, the receptor proteins were expressed in large quantities on the membrane, and the cells were centrifuged at 1000 rpm for 5 min and then the culture solution was discarded, and the cells were collected, and stored in a −20° C. refrigerator for later use. Tris-HCl reaction buffer (pH 7.7) was used to resuspend in the experiment.

Receptor competitive binding experiment: 10 µL of the test compound, 10 µL of the radioactive ligand and 80 µL of the receptor protein were added to the reaction tube, so that the final concentration of the test compound and the positive drug were both 10 µmol/L, and after incubation for 15 min in a 37° C. water bath, and the mixture was immediately transferred to an ice bath to terminate the reaction. On the Millipore cell sample collector, the mixture was quickly filtrated under reduced pressure through GF/B glass fiber filter paper, and eluted with 3 mL of eluent (50 mM Tris-HCl, PH 7.7) for 3 times, then dried under microwave for 8 to 9 min. The filter paper was moved into a 0.5 mL centrifuge tube, and 500 µL of lipid-soluble scintillation solution was added. The mixture was kept in the dark for more than 30 min, and the radioactivity intensity was determined by counting. The inhibition rate percentage of each compound to isotopic ligand binding was calculated according to the following formula:

Inhibition rate ($I\%$)=(total binding tube CPM−compound CPM)/(total binding tube CPM−non-specific binding tube CPM)×100%

Two replicate tubes were made for each experiment of compound, and two separate experiments were performed.

The compounds with an inhibition rate greater than 95% were subjected to receptor binding tests in a series of concentrations to determine the half inhibition amount ($IC_{50}$, concentration of compound required to inhibit [$^3$H]-Ketanserin binding to 5-$HT_{2A}$ receptor).

Two tubes were tested for each concentration and two independent tests were performed for each compound.

$Ki=IC_{50}/(1+[L]/K_D)$ (Ki: affinity of the drug and the receptor, L: concentration of radioactive ligands, $K_D$: affinity value of the radioactive ligand and the receptor)

5-$HT_{2A}$ receptor binding test results of the compound of the present disclosure are shown in table 1.

The test results in table 1 show that the compounds of the present disclosure have strong affinity for 5-$HT_{2A}$ receptors, and most of the compound have stronger affinity for 5-$HT_{2A}$ than that of the positive drug cariprazine.

TABLE 1

Affinity of the compound for each receptor (Ki value, nM)

| No. | $D_2$ | $D_3$ | 5-$HT_{2A}$ |
|---|---|---|---|
| I-1 | 3.1 | 0.2 | 1.7 |
| I-2 | 1.2 | 0.1 | 1.9 |
| I-3 | 2.5 | 0.08 | 2.1 |
| I-4 | 2.0 | 0.05 | 3.9 |
| I-5 | 8.6 | 0.9 | 1.1 |
| I-6 | 0.14 | 0.02 | 1.0 |
| I-7 | 0.12 | 0.01 | 0.2 |
| II-1 | 1.7 | 0.2 | 2.3 |
| II-2 | 0.9 | 0.07 | 2.4 |
| II-3 | 1.4 | 0.09 | 1.2 |
| II-4 | 2.8 | 0.3 | 0.9 |
| II-6 | 1.0 | 0.04 | 1.3 |
| III-1 | 3.2 | 0.2 | 10.8 |
| III-2 | 1.9 | 0.07 | 5.1 |
| III-3 | 4.6 | 0.5 | 12.5 |
| III-4 | 11.8 | 1.2 | 6.6 |
| IV-1 | 2.5 | 0.05 | 2.7 |
| IV-2 | 0.9 | 0.03 | 1.1 |
| IV-3 | 2.0 | 0.1 | 3.6 |
| IV-4 | 1.7 | 0.08 | 8.7 |
| V-1 | 8.1 | 0.7 | 1.6 |
| V-2 | 15.2 | 1.2 | 8.8 |
| V-3 | 7.1 | 0.07 | 5.0 |
| V-4 | 10.6 | 0.3 | 2.8 |
| V-5 | 1.0 | 0.04 | 2.9 |
| VI-1 | 0.8 | 0.05 | 1.6 |
| VI-2 | 1.3 | 0.08 | 2.1 |
| VI-3 | 1.9 | 0.8 | 1.7 |
| VI-4 | 2.0 | 0.1 | 0.9 |
| VI-5 | 1.0 | 0.07 | 1.1 |
| VII-1 | 4.5 | 0.28 | 3.2 |
| VII-2 | 2.6 | 0.1 | 0.7 |
| VII-3 | 5.1 | 1.2 | 3.8 |
| VII-4 | 0.6 | 0.03 | 1.1 |
| VII-5 | 4.0 | 0.3 | 7.9 |
| Cariprazine | 0.8 | 0.08 | 22.1 |

Therefore, it can be seen from the results in table 1 that the compounds of the present disclosure have strong affinity for $D_3$ and 5-$HT_{2A}$ receptors, and strong or moderate affinity for $D_2$ receptors. In addition, most of the compounds have appropriate selectivity to $D_2/D_3$ receptor, and the selectivity is between 10 to 60 times, which is better than that of cariprazine (the selectivity is less than 10 times). The affinity of most compounds for 5-$HT_{2A}$ receptor is significantly better than that of positive control drugs. Therefore, such compounds have the potential of simultaneously improving cognitive impairment effects and low EPS side effects.

Example 42

$H_1$ Receptor Binding Test

HEK-293 cell membrane homogenate (12.5 μg/point) infected with recombinant virus containing $H_1$ receptor protein gene and 1 nM [$^3$H]pyrilamine (purchased from Sigma Company) were incubated in buffer solution containing 37 mM NaCl, 2.68 mM KCl, 8.1 mM $Na_2HPO_4$ and 1.47 mM $KH_2PO_4$ (pH 7.4) for 60 min in the presence or absence of test compound. Non-specific binding was determined in the presence of 1 μM pyrilamine. After the incubation, the mixture was quickly filtered under reduced pressure through GF/B glass fiber filter paper, and eluted with 3 mL of eluent (50 mM Tris-HCl, PH 7.7) for 3 times, and dried under microwave for 8 to 9 minutes. The filter paper was moved into a 0.5 mL centrifuge tube and 500 μL lipid-soluble scintillation solution was added. The mixture was kept in the dark for more than 30 min, and the radioactivity intensity was determined by counting. The inhibition rate percentage of each compound to isotopic ligand binding was calculated according to the following formula:

Inhibition rate (I%)=(total binding tube CPM−compound CPM)/(total binding tube CPM−non-specific binding tube CPM)×100%

Two replicate tubes were made for each experiment of compound, and two separate experiments were performed.

The inhibition rate of the all compounds of the present disclosure was higher than 95%, and then receptor binding tests in a series of concentrations were then performed on the compound of the present disclosure to determine the half inhibition amount ($IC_{50}$, concentration of compound required to inhibit 50% [$^3$H] pyrilamine binding to $H_1$ receptor). Two tubes were tested for each concentration and two independent tests were performed for each compound.

$Ki=IC_{50}/(1+[L]/K_D)$ (Ki: affinity of the drug and the receptor, L: concentration of radioactive ligands, $K_D$: affinity value of the radioactive ligand and the receptor)

$H_1$ receptor binding test results of the compound of the present disclosure are shown in table 2. The test results of table 2 show that most of the compounds of the present disclosure have weak or no affinity for $H_1$ receptors, and the affinity is more than 100 times lower than the efficacy target (the affinity of the efficacy target is between 0.03 and 12 nM), which is significantly lower than the marketed drug cariprazine. Therefore, the series of compounds of the present disclosure have low side effects of potential sedation and weight gain.

TABLE 2

Affinity of the compound for $H_1$ receptor (Ki value, nM)

| No. | $H_1$ |
|---|---|
| I-1 | 760 |
| I-2 | 950 |
| I-3 | >1000 |
| I-4 | 550 |
| I-5 | >1000 |
| I-6 | >1000 |
| I-7 | 420 |
| II-1 | 670 |
| II-2 | >1000 |
| II-3 | 980 |
| II-4 | 540 |
| II-5 | 300 |
| II-6 | >1000 |
| III-1 | >1000 |
| III-2 | >1000 |
| III-3 | >1000 |
| III-4 | 980 |
| IV-1 | >1000 |
| IV-2 | >1000 |
| IV-3 | 790 |
| IV-4 | 670 |
| V-1 | 530 |
| V-2 | 740 |

TABLE 2-continued

Affinity of the compound for $H_1$ receptor (Ki value, nM)

| No. | $H_1$ |
|---|---|
| V-3 | 800 |
| V-4 | >1000 |
| V-5 | >1000 |
| VI-1 | >1000 |
| VI-2 | >1000 |
| VI-3 | 740 |
| VI-4 | 590 |
| VI-5 | >1000 |
| VII-1 | 460 |
| VII-2 | 600 |
| VII-3 | 870 |
| VII-4 | >1000 |
| VII-5 | >1000 |
| Cariprazine | 30 |

Example 43

In vivo anti-schizophrenia activity test of the compound of the present disclosure In this example, the compound with $D_2/D_3$ receptor selectivity between 10 and 60 times, with strong affinity for $D_2/D_3/5\text{-}HT_{2A}$ receptor and weak affinity for $H_1$ receptor were selected for in vivo anti-schizophrenia activity test.

1. Apomorphine Model Experiment (1) Test Method

An acute mode of administration was used in the experiment.

The experimental mice were randomly divided into groups, and after the control or test compound was administrated by gavage for 30 minutes, apomorphine (5 mg/kg) was injected intraperitoneally to induce a stereotyped motion model. The following symptoms were observed in the first 30 seconds of every 10 minutes (0-10 minutes, 11-20 minutes, 21-30 minutes, 31-40 minutes, 41-50 minutes, 51-60 minutes, 61-70 minutes) within 70 minutes after the apomorphine solution was administered to mice, and scored according to the following standards:

1) 4 point, continuous biting;

2) 3 point, the cage lid was bit at least once during observation;

3) 2 point, the cage chassis or cage wall was licked at least once during observation;

4) 1 point, compulsive sniffing and bowing activities were appeared;

5) 0 point, no of the above activities.

The total score of the mice was calculated for the above behaviors within 70 min, and the improvement rate was calculated according to the following formula. The data were expressed as mean±standard error (Mean±SEM), and were analyzed using GraphPad Prism software, and data analysis was performed using t-test, and a significant difference was considered to exist when P<0.05.

Improvement rate =

$$\frac{\text{Stereotyped motion scoring in model control group} - \text{Stereotyped motion scoring in administration group}}{\text{Stereotyped motion scoring in model control group}} \times 100\%$$

(2) Experimental Grouping and Administration Design

C57BL/6 mice were randomly divided into 6 groups with at least 9 mice in each group, namely model control group (apomorphine, dissolved in normal saline), cariprazine (positive control drug), the compound of the present disclosure, respectively.

(3) Administration and Observation after Administration

The compound claimed in the present disclosure and the positive drug cariprazine were administered with gradient doses of 0.05, 0.10, 0.20, 0.60, 1.20, 1.50 mg·kg$^{-1}$ (oral gavage). During the experiment, the clinical response symptoms of the animals were recorded.

(4) Statistical Methods

All data were expressed as x̄±SEM, processed with the 11.5 software statistical package, and t-test and one-way analysis of variance were performed for the comparison of the means of the two samples, with P<0.05 as a significant difference.

(5) Experimental Results

The specific experimental results are shown in table 3.

TABLE 3

Inhibition of total stereotyped motion of mouse schizophrenic model induced by Apo. with single oral administration of compound I-3 and other compounds ($ED_{50}$)

| Compound | $ED_{50}$ (mg/kg) |
|---|---|
| I-3 | 0.19 |
| I-6 | 0.43 |
| II-2 | 0.08 |
| II-6 | 0.13 |
| IV-2 | 0.10 |
| V-5 | 0.78 |
| VI-1 | 0.55 |
| VI-5 | 0.16 |
| VII-4 | 0.20 |
| Cariprazine | 0.30 |

The results of this test show that: Compared with the positive control drug cariprazine, the compounds of the present disclosure can significantly improve the stereotyped behavior of mice, and the schizophrenia model induced by apomorphine is a classic model of schizophrenia, so the series of the compounds of the present disclosure have good anti-schizophrenia effect. Compound I-3, II-2, II-6, IV-2, VI-5, VII-4 have better effects ($ED_{50}$) on the stereotyped behavior of mice than the positive control drug cariprazine.

2. MK-801 model Experiment (1) Test Method

An acute mode of administration was used in the experiment. The experimental mice were randomly divided into groups and put into a spontaneous activity box to adapt for 5-10 minutes before the experiment. After 10 minutes of intragastric administration, the animals were intraperitoneally injected with MK-801 (0.5 mg/kg), and put back into the spontaneous activity box to start infrared monitoring, and the video of animal activities was continuously collected for 90 minutes. After the experiment, the video files were analyzed with SPSS 11.5 software statistical package, and the total distance of activities within 90 minutes was obtained. The data were expressed as mean±standard error (Mean±SEM), and were analyzed using GraphPad Prism software, and data analysis was performed using t-test, and a significant difference was considered to exist when P<0.05.

(2) Experimental Grouping and Administration Design

57BL/6 mice were randomly divided into 6 groups with at least 12 mice in each group, namely blank control group, model control group (MK-801, dissolved in normal saline), cariprazine group and compound group of the present disclosure. Cariprazine was used as a positive drug control, and MK-801 was a tool drug for modeling.

(3) Experimental Results

The specific results are shown in table 4.

TABLE 4

Effect of single oral administration on the total distance of open-field motion in mouse model of schizophrenia induced by MK-801 ($ED_{50}$)

| Compound | $ED_{50}$ (mg/kg) |
|---|---|
| I-3 | 0.33 |
| I-6 | 0.20 |
| II-2 | 0.07 |
| II-6 | 0.10 |
| IV-2 | 0.05 |
| V-5 | 0.51 |
| VI-1 | 0.12 |
| VI-5 | 0.08 |
| VII-4 | 0.25 |
| Cariprazine | 0.15 |

The experimental results show that the cariprazine group and the compounds of the present disclosure can obviously improve the total distance of open-field motion in mice, because the open-field motion model induced by MK-801 is a common model of negative symptoms of schizophrenia, so the series of the compounds of the present disclosure have good anti-negative symptoms effect of schizophrenia. The improvement rate of compound II-2, II-6, IV-2, II-2, VI-1 on open-field motion of mice is better than that of the positive drug control cariprazine, indicating that the activity of compound II-2, II-6, IV-2, II-2, VI-1 is better than that of carilazine in this model.

Example 44

Acute Toxicity Experiments of the Compound

In this example, 10 compounds of the present disclosure (I-3, I-6, II-2, II-6, IV-2, V-5, VI-1, VI-5 and VII-4) and cariprazine (positive control drug) were selected for acute toxicity experiments.

(1) Experimental Protocol

1) The toxicity symptoms and death conditions were observed after the oral administration of cariprazine and compound I-3 and other compounds of the present disclosure in ICR mice, and the acute toxicity was compared.

2) Solvent preparation: An appropriate amount of Tween-80 was weighed and diluted with deionized water to a concentration of 5% (g/v) Tween-80.

3) Preparation for administration: The required test samples were weighed respectively, and prepared into suspensions with concentrations of 6.25, 12.50, 25.00, 50.00 and 100.00 mg/mL (equivalent to 125, 250, 500, 1000 and 2000 mg/kg, respectively) with 5% Tween-80 solution.

4) Route of administration: The administration route of the test samples and the solvent control group (0.5% Tween-80) was oral administration.

5) Frequency of administration: Single administration, fasting overnight before administration.

6) Dosing capacity: 20 mL/kg.

General symptom observation: On the day of administration, the observation was performed once about 0.5, 1, 2, 4 and 6 hours after the first administration; the observation period was 2 to 6 days, twice a day, once in the morning and once in the afternoon.

The observation content includes, but is not limited to, general condition, behavioral activity, gait posture, eye, mouth, nose, gastrointestinal tract, skin hair, urogenital tract.

(2) Statistical Analysis

Body weight data were expressed as mean±standard deviation, and were compared between groups using Levene's test and one-way ANOVA. If there were differences, Dunnet t test was used.

(3) Experimental Results 10 compounds of the present disclosure and cariprazine (positive control drug) were selected for acute toxicity experiments as described above. The experimental results are shown in table 5.

In the MTD test, the tolerance of the animals to the drug was investigated, and the maximum tolerated dose was reached when the animals were dying frequently.

TABLE 5

Acute toxicity test results of single oral administration of compound I-3 and other compounds and cariprazine positive drug

| Test sample | MTD (mg/kg) |
|---|---|
| I-3 | 800 mg/kg |
| I-6 | >2000 mg/kg |
| II-2 | 450 mg/kg |
| II-6 | 1100 mg/kg |
| IV-2 | >2000 mg/kg |
| V-5 | 450 mg/kg |
| VI-1 | 900 mg/kg |
| VI-5 | >2000 mg/kg |
| VII-4 | 400 mg/kg |
| Cariprazine | 320 mg/kg |

Note:
MTD maximum tolerance.

The results show that the MTD (maximum tolerance) of compounds I-6, IV-2 and VI-5 of the present disclosure in the above test samples are greater than 2000 mg/kg, and the acute toxicity is much lower than that of carlirazine; compounds I-3, II-2, II-6, V-5, VI-1 and VII-4 have MTD values greater than or equal to 400 mg/kg, which are better than that of cariprazine.

Although the specific embodiments of the present disclosure have been described above, those skilled in the art should understand that these are only embodiments, and various changes or modifications can be made to these embodiments without departing from the principle and essence of the present disclosure. Accordingly, the scope of protection of the present disclosure is defined by the claims.

The invention claimed is:

1. A pyridinyl morpholine compound represented by formula I, a pharmaceutically acceptable salt thereof, or a hydrate of the pharmaceutically acceptable salt thereof:

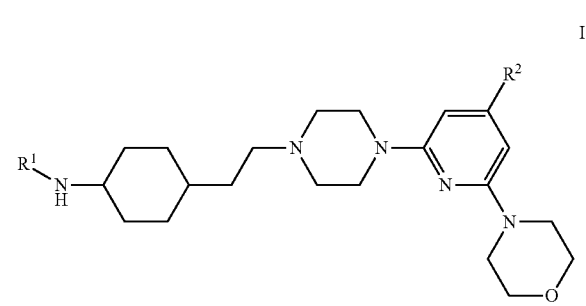

wherein, $R^1$ is

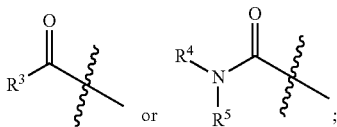

or ;

$R^3$ is $C_1$-$C_3$ alkyl, "$C_1$-$C_3$ alkyl substituted by one $C_1$-$C_3$ alkoxy", $C_3$-$C_6$ cycloalkyl, phenyl, "5- to 6-membered heteroaryl with 1 to 2 heteroatoms selected from one or more of N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom;

$R^4$ and $R^5$ are independently hydrogen or $C_1$-$C_3$ alkyl;

$R^2$ is phenyl, "5- to 6-membered heteroaryl with 1 to 2 heteroatoms selected from one or more of N, O and S", or, phenyl substituted by one or more $R^{2-1}$;

$R^{2-1}$ is independently $C_1$-$C_3$ alkoxy or halogen.

2. The pyridinyl morpholine compound represented by formula I, the pharmaceutically acceptable salt thereof, or the hydrate of the pharmaceutically acceptable salt thereof according to claim 1, wherein, $R^3$ is defined as any one of the definitions (1) to (6), definition (1), $R^3$ is $C_1$-$C_3$ alkyl,

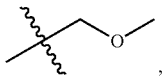 [SMILES: *COC]

, $C_3$-$C_6$ cycloalkyl, or "5- to 6-membered heteroaryl with one heteroatom selected from N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom;

definition (2), $R^3$ is $C_1$-$C_3$ alkyl,

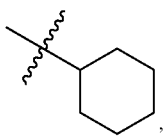 [SMILES: *C1CCCCC1]

, furanyl, pyridyl, tetrahydropyrrolyl, morpholinyl, piperidinyl or piperazinyl;

definition (3), $R^3$ is furanyl, pyridyl or tetrahydropyrrolyl;
definition (4), $R^3$ is $C_1$-$C_3$ alkyl,

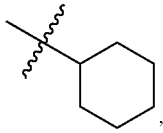

, furanyl, pyridyl, tetrahydropyrrolyl or piperazinyl;

definition (5), $R^3$ is "5- to 6-membered heteroaryl with 1 heteroatom selected from N and O" or tetrahydropyrrolyl;

and, definition (6), $R^3$ is $C_3$ alkyl, "$C_1$-$C_3$ alkyl substituted by one $C_1$-$C_3$ alkoxy", phenyl, tetrahydropyrrolyl, morpholinyl, piperidinyl, piperazinyl or methylpiperazinyl; or, $R^2$ is defined as definition (a) or definition (b); definition (a), phenyl, "5- to 6-membered heteroaryl with 1 heteroatom selected from N, O and S" or phenyl substituted by one $R^{2-1}$;

definition (b), $R^2$ is phenyl, "5- to 6-membered heteroaryl with 1 heteroatom selected from N and S" or phenyl substituted with one $R^{2-1}$, or, $R^4$ and $R^5$ are independently $C_1$-$C_3$ alkyl;

or, $R^{2-1}$ is independently $C_1$-$C_3$ alkoxy or fluorine.

3. The pyridinyl morpholine compound represented by formula I, the pharmaceutically acceptable salt thereof, or the hydrate of the pharmaceutically acceptable salt thereof according to claim 2, wherein, the definitions of the groups of the pyridinyl morpholine compound represented by formula I are as described in scheme 1, scheme 2, scheme 3, scheme 4 or scheme 5;

scheme 1:
$R^3$ is $C_1$-$C_3$ alkyl,

, $C_3$-$C_6$ cycloalkyl, "5- to 6-membered heteroaryl with 1 heteroatom selected from N, O and S", "5- to 6-membered heterocycloalkyl with one heteroatom of N, and 0 or 1 heteroatom selected from N, O and S", or, "5- to 6-membered heterocycloalkyl with one heteroatom of N, and 0 or 1 heteroatom selected from N, O and S" substituted by one $C_1$-$C_3$ alkyl; the heterocycloalkyl is connected to the carbonyl in $R^1$ by N atom;

$R^2$ is phenyl, "5- to 6-membered heteroaryl with 1 heteroatom selected from N, O and S", or phenyl substituted by one or more $R^{2-1}$;

$R^{2-1}$ is independently $C_1$-$C_3$ alkoxy or halogen;

scheme 2:
$R^3$ is $C_1$-$C_3$ alkyl,

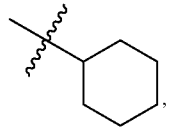

, furanyl, pyridyl, tetrahydropyrrolyl, morpholinyl, piperidinyl or piperazinyl;

$R^4$ and $R^5$ are independently $C_1$-$C_3$ alkyl;

$R^2$ is phenyl, "5- to 6-membered heteroaryl with 1 heteroatom selected from N and S", or phenyl substituted by one or more $R^{2-1}$;

$R^{2-1}$ is independently $C_1$-$C_3$ alkoxy or halogen;

scheme 3:
$R^3$ is furanyl, pyridyl or tetrahydropyrrolyl;
$R^4$ and $R^5$ are independently $C_1$-$C_3$ alkyl;

R² is phenyl, "5- to 6-membered heteroaryl with 1 heteroatom selected from N and S", or phenyl substituted by one or more R²⁻¹;
R²⁻¹ is independently $C_1$-$C_3$ alkoxy or halogen;
scheme 4:
R³ is $C_1$-$C_3$ alkyl,

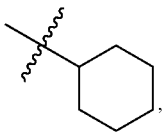 [SMILES: *C1CCCCC1]

furanyl, pyridyl, tetrahydropyrrolyl or piperazinyl;
R⁴ and R⁵ are independently $C_1$-$C_3$ alkyl;
R² is phenyl, "5- to 6-membered heteroaryl with 1 heteroatom selected from N and S", or phenyl substituted by one or more R²⁻¹;
R²⁻¹ is independently $C_1$-$C_3$ alkoxy or halogen;
scheme 5:
R³ is $C_3$ alkyl, "$C_1$-$C_3$ alkyl substituted by one $C_1$-$C_3$ alkoxy", phenyl, tetrahydropyrrolyl, morpholinyl, piperidinyl, piperazinyl or methylpiperazinyl;
R⁴ and R⁵ are independently $C_1$-$C_3$ alkyl;
R² is phenyl, "5- to 6-membered heteroaryl with 1 heteroatom selected from N and S", or phenyl substituted by one or more R²⁻¹.

4. The pyridinyl morpholine compound represented by formula I, the pharmaceutically acceptable salt thereof, or the hydrate of the pharmaceutically acceptable salt thereof according to claim 1, wherein, the pyridinyl morpholine compound represented by formula I is the pyridinyl morpholine compound represented by formula I-1 or the pyridinyl morpholine compound represented by formula I-2:

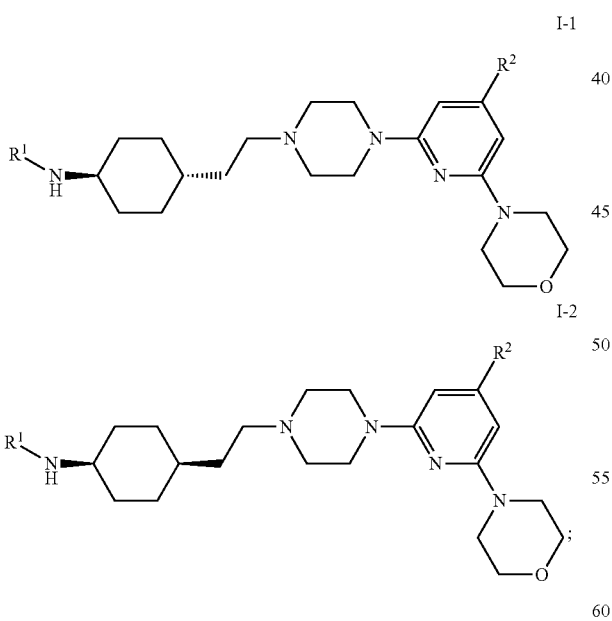

or, in the pharmaceutically acceptable salt, the salt is hydrochloride, hydrobromide, sulfate, methanesulfonate or trifluoroacetate;
or, in the pharmaceutically acceptable salt, relative to the pyridinyl morpholine compound represented by formula I, the number of acid molecular contained in the salt is 0.5 to 2;
or, in the hydrate of the pharmaceutically acceptable salt, the salt is hydrochloride, bromate, sulfate, trifluoroacetate, methanesulfonate or palmitate;
or, in the hydrate of the pharmaceutically acceptable salt, relative to the pyridinyl morpholine compound represented by formula I, the number of acid molecular contained in the hydrate of the salt is 0.5 to 2;
or, in the hydrate of the pharmaceutically acceptable salt, relative to the pyridinyl morpholine compound represented by formula I, the number of water molecular contained in the hydrate of the salt is 0.5 to 2.

5. The pyridinyl morpholine compound represented by formula I, the pharmaceutically acceptable salt thereof, or the hydrate of the pharmaceutically acceptable salt thereof according to claim 4, wherein, the pyridinyl morpholine compound represented by formula I is the pyridinyl morpholine compound represented by formula I-1:

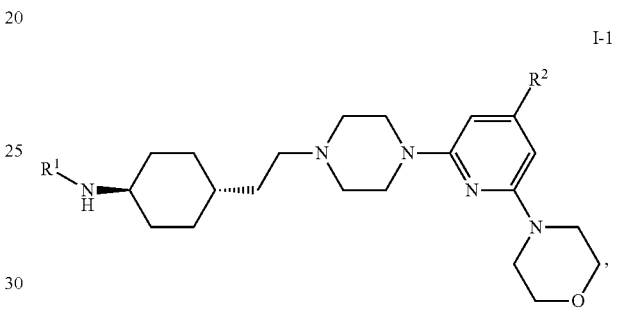

when R³ is $C_1$-$C_3$ alkyl substituted by one $C_1$-$C_3$ alkoxy, the $C_1$-$C_3$ alkyl substituted by one $C_1$-$C_3$ alkoxy is

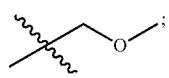 [SMILES: *COC]

when R³ is "5- to 6-membered heteroaryl with 1 heteroatom selected from N, O and S", the "5- to 6-membered heteroaryl with 1 heteroatom selected from N, O and S" is furanyl or pyridyl;
when R³ is "5- to 6-membered heterocycloalkyl with one heteroatom of N, and 0 or 1 heteroatom selected from N, O and S substituted by one $C_1$-$C_3$ alkyl", the $C_1$-$C_3$ alkyl is methyl;
when R³ is "5- to 6-membered heterocycloalkyl with one heteroatom of N, and 0 or 1 heteroatom selected from N, O and S substituted by one $C_1$-$C_3$ alkyl", the "5- to 6-membered heterocycloalkyl with one heteroatom of N, and 0 or 1 heteroatom selected from N, O and S substituted by one $C_1$-$C_3$ alkyl" is

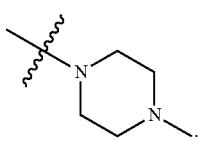 [SMILES: *N1CCN(C)CC1]

6. The pyridinyl morpholine compound represented by formula I, the pharmaceutically acceptable salt thereof, or the hydrate of the pharmaceutically acceptable salt thereof according to claim 5, wherein, when R³ is "5- to 6-membered heteroaryl with 1 heteroatom selected from N, O and S", the "5- to 6-membered heteroaryl with 1 heteroatom selected from N, O and S" is

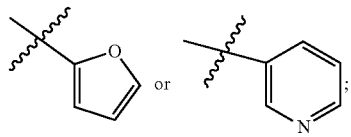 [SMILES: *c1ccco1 ; *c1cccnc1]

or, when R² is "5- to 6-membered heteroaryl with 1 heteroatom selected from N, O and S", the "5- to 6-membered heteroaryl with 1 heteroatom selected from N, O and S" is

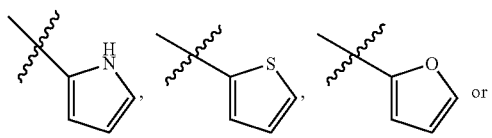

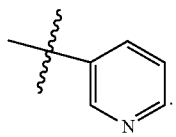

7. The pyridinyl morpholine compound represented by formula I, the pharmaceutically acceptable salt thereof, or the hydrate of the pharmaceutically acceptable salt thereof according to claim 6, wherein, R¹ is

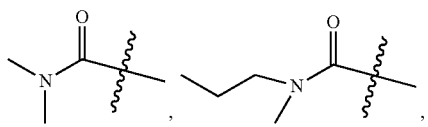

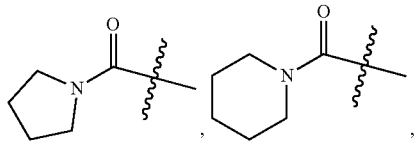

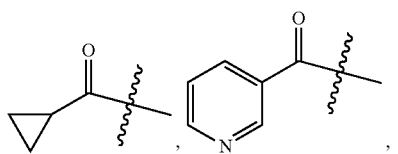

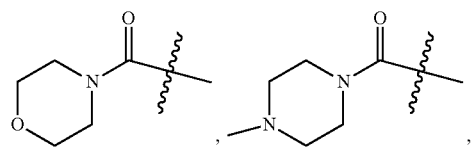

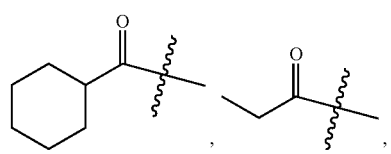

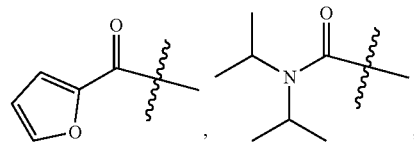

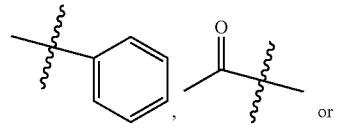

or, R² is

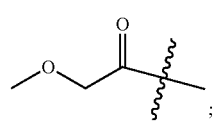

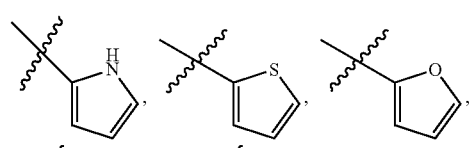

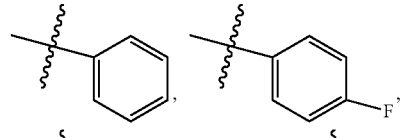

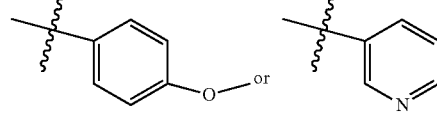

8. The pyridinyl morpholine compound represented by formula I, the pharmaceutically acceptable salt thereof, or the hydrate of the pharmaceutically acceptable salt thereof according to claim 1, wherein, the pyridinyl morpholine compound represented by formula I is any one of the following compounds:

| No. | Structure |
|---|---|
| I-1 | 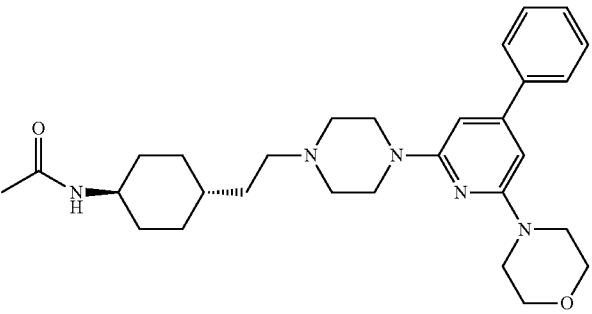 [SMILES: CC(=O)N[C@H]1CC[C@H](CCN2CCN(c3cc(-c4ccccc4)cc(N4CCOCC4)n3)CC2)CC1] |
| I-2 | 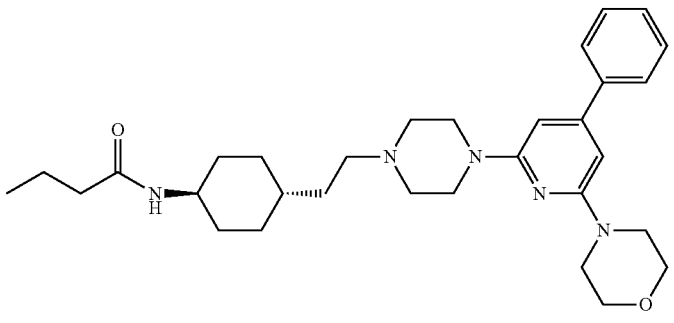 [SMILES: CCCC(=O)N[C@H]1CC[C@H](CCN2CCN(c3cc(-c4ccccc4)cc(N4CCOCC4)n3)CC2)CC1] |
| I-3 | 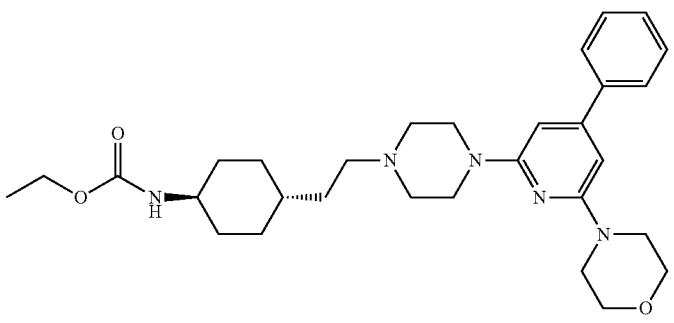 [SMILES: CCOC(=O)N[C@H]1CC[C@H](CCN2CCN(c3cc(-c4ccccc4)cc(N4CCOCC4)n3)CC2)CC1] |
| I-4 | 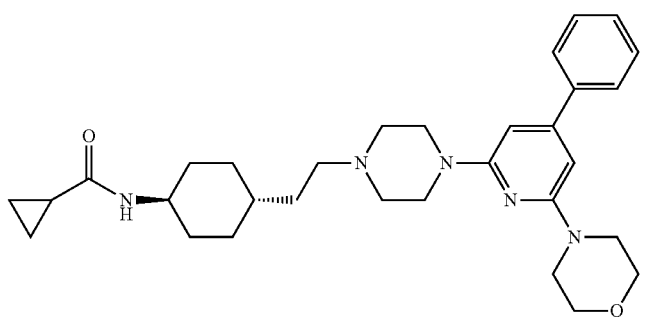 [SMILES: O=C(N[C@H]1CC[C@H](CCN2CCN(c3cc(-c4ccccc4)cc(N4CCOCC4)n3)CC2)CC1)C1CC1] |
| I-5 | 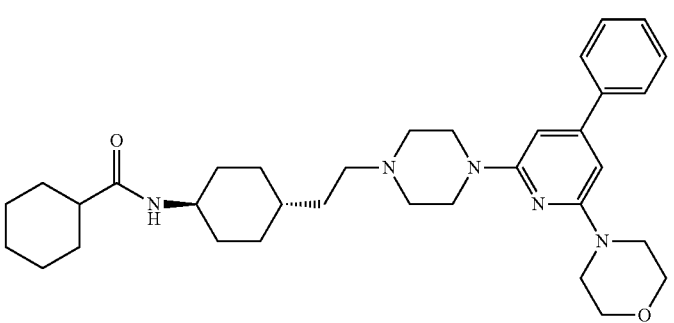 [SMILES: O=C(N[C@H]1CC[C@H](CCN2CCN(c3cc(-c4ccccc4)cc(N4CCOCC4)n3)CC2)CC1)C1CCCCC1] |

-continued
| No. | Structure |
|---|---|
| I-6 | 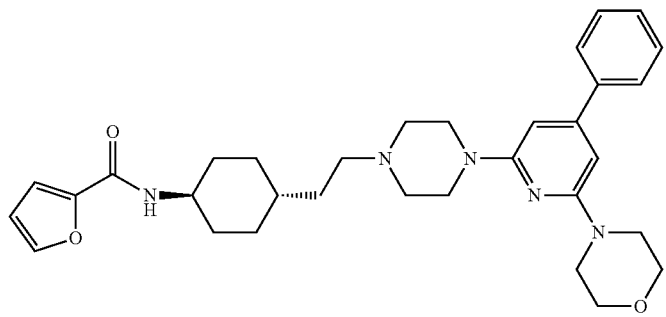 [SMILES: O=C(N[C@H]1CC[C@H](CCN2CCN(c3cc(-c4ccccc4)cc(N4CCOCC4)n3)CC2)CC1)c1ccco1] |
| I-7 | 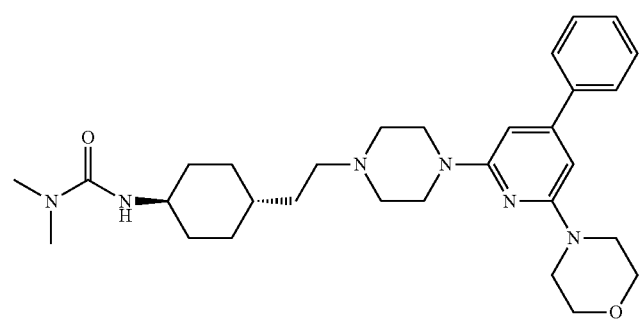 [SMILES: CN(C)C(=O)N[C@H]1CC[C@H](CCN2CCN(c3cc(-c4ccccc4)cc(N4CCOCC4)n3)CC2)CC1] |
| II-1 | 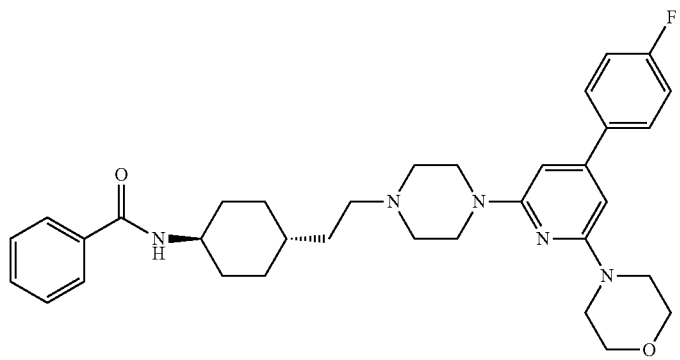 [SMILES: O=C(N[C@H]1CC[C@H](CCN2CCN(c3cc(-c4ccc(F)cc4)cc(N4CCOCC4)n3)CC2)CC1)c1ccccc1] |
| II-2 | 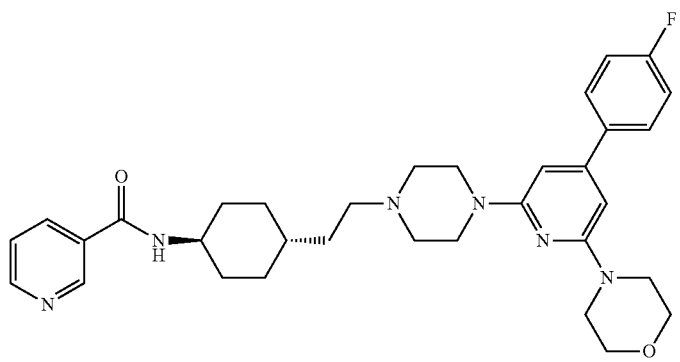 |

| No. | Structure |
|---|---|
| II-3 | 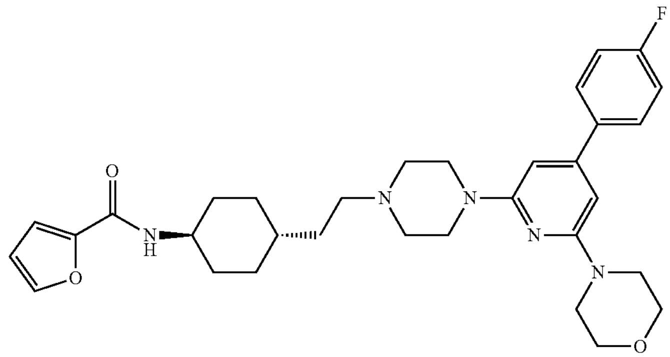 [SMILES: O=C(N[C@H]1CC[C@H](CCN2CCN(c3cc(-c4ccc(F)cc4)cc(N4CCOCC4)n3)CC2)CC1)c1ccco1] |
| II-4 | 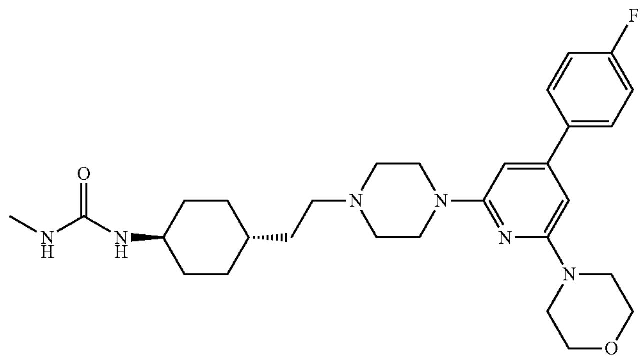 [SMILES: CNC(=O)N[C@H]1CC[C@H](CCN2CCN(c3cc(-c4ccc(F)cc4)cc(N4CCOCC4)n3)CC2)CC1] |
| II-5 | 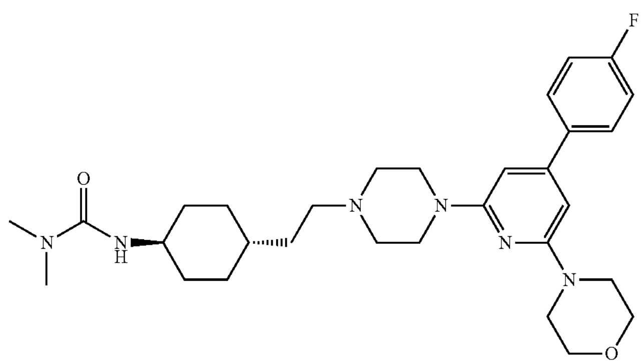 [SMILES: CN(C)C(=O)N[C@H]1CC[C@H](CCN2CCN(c3cc(-c4ccc(F)cc4)cc(N4CCOCC4)n3)CC2)CC1] |
| II-6 | 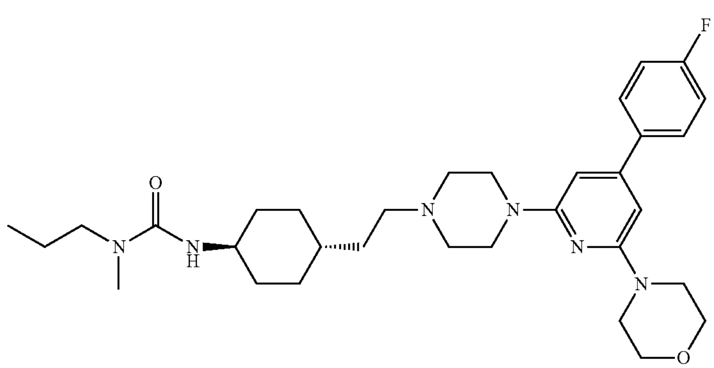 [SMILES: CCCN(C)C(=O)N[C@H]1CC[C@H](CCN2CCN(c3cc(-c4ccc(F)cc4)cc(N4CCOCC4)n3)CC2)CC1] |

-continued

| No. | Structure |
|---|---|
| III-1 | 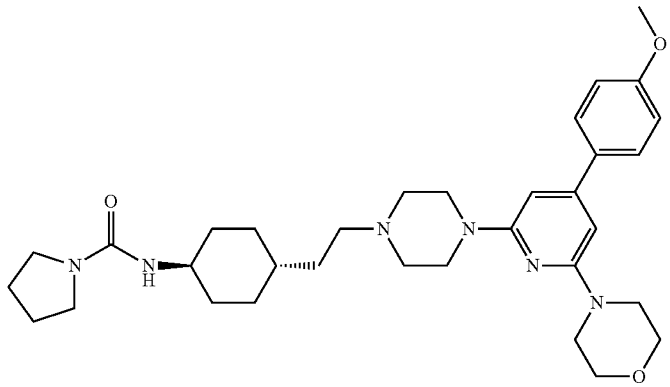 [SMILES: COc1ccc(-c2cc(N3CCOCC3)nc(N3CCN(CC[C@H]4CC[C@H](NC(=O)N5CCCC5)CC4)CC3)c2)cc1] |
| III-2 | 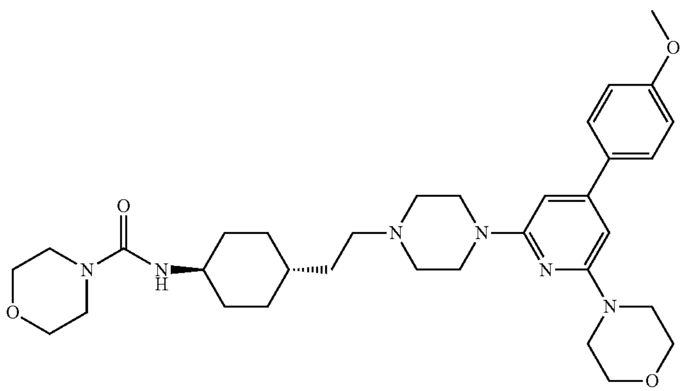 [SMILES: COc1ccc(-c2cc(N3CCOCC3)nc(N3CCN(CC[C@H]4CC[C@H](NC(=O)N5CCOCC5)CC4)CC3)c2)cc1] |
| III-3 | 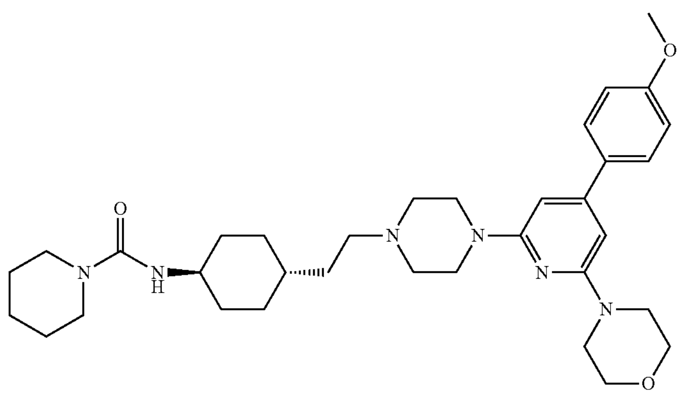 [SMILES: COc1ccc(-c2cc(N3CCOCC3)nc(N3CCN(CC[C@H]4CC[C@H](NC(=O)N5CCCCC5)CC4)CC3)c2)cc1] |
| III-4 | 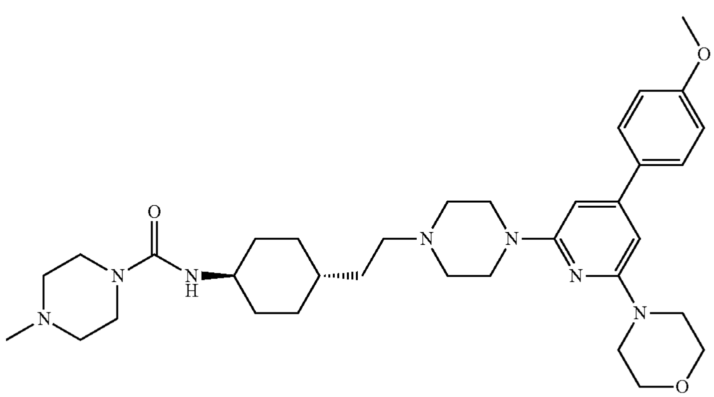 [SMILES: COc1ccc(-c2cc(N3CCOCC3)nc(N3CCN(CC[C@H]4CC[C@H](NC(=O)N5CCN(C)CC5)CC4)CC3)c2)cc1] |

-continued

| No. | Structure |
|---|---|
| IV-1 | 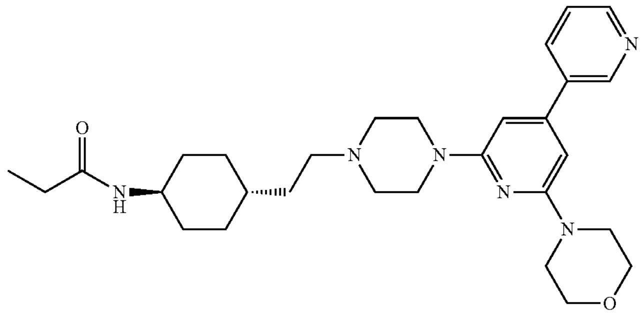 [SMILES: CCC(=O)N[C@H]1CC[C@H](CCN2CCN(c3cc(-c4cccnc4)cc(N4CCOCC4)n3)CC2)CC1] |
| IV-2 | 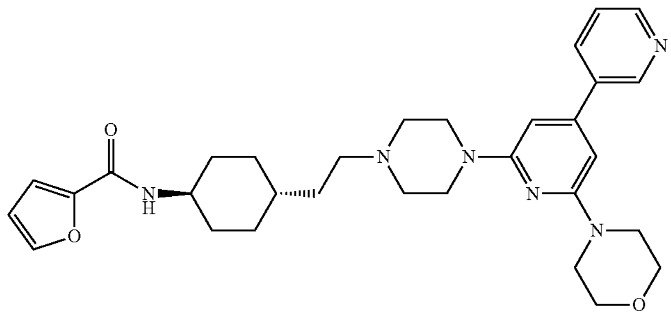 [SMILES: O=C(N[C@H]1CC[C@H](CCN2CCN(c3cc(-c4cccnc4)cc(N4CCOCC4)n3)CC2)CC1)c1ccco1] |
| IV-3 | 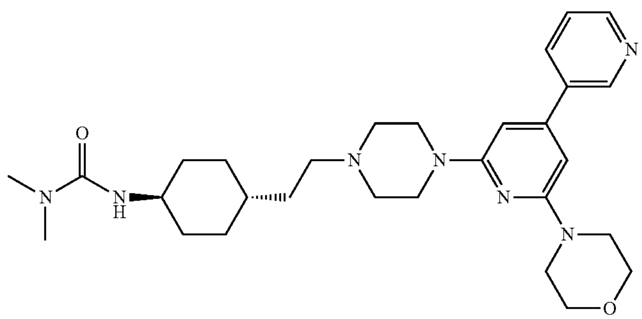 |
| IV-4 | 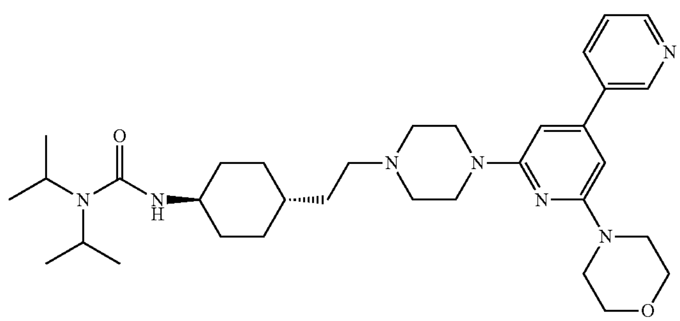 [SMILES: CC(C)N(C(=O)N[C@H]1CC[C@H](CCN2CCN(c3cc(-c4cccnc4)cc(N4CCOCC4)n3)CC2)CC1)C(C)C] |
| V-1 | 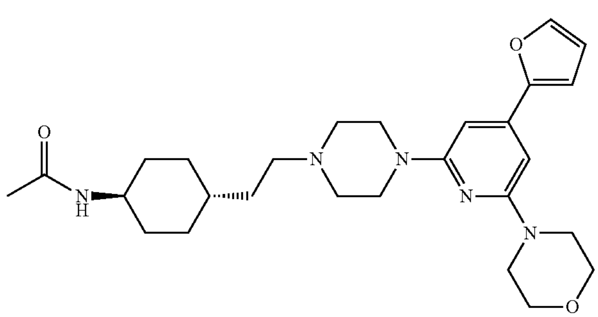 [SMILES: CC(=O)N[C@H]1CC[C@H](CCN2CCN(c3cc(-c4ccco4)cc(N4CCOCC4)n3)CC2)CC1] |

| No. | Structure |
|---|---|
| V-2 | 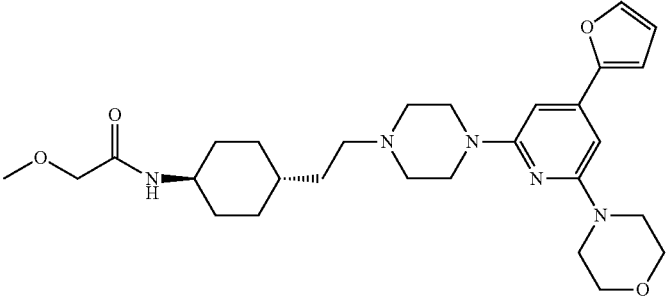 [SMILES: COCC(=O)N[C@H]1CC[C@H](CCN2CCN(c3cc(-c4ccco4)cc(N4CCOCC4)n3)CC2)CC1] |
| V-3 | 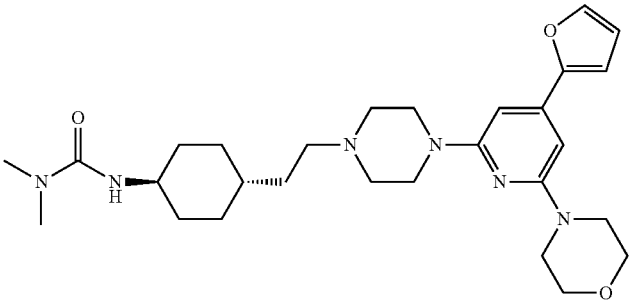 |
| V-4 | 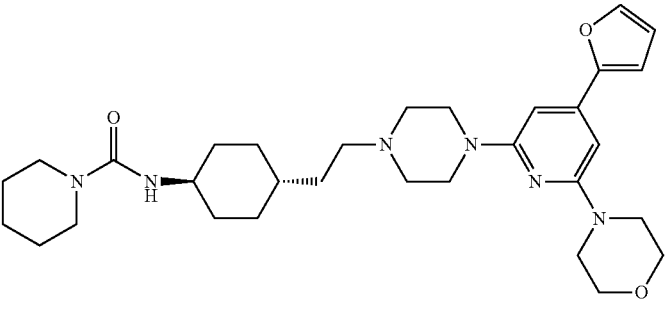 [SMILES: O=C(N[C@H]1CC[C@H](CCN2CCN(c3cc(-c4ccco4)cc(N4CCOCC4)n3)CC2)CC1)N1CCCCC1] |
| V-5 | 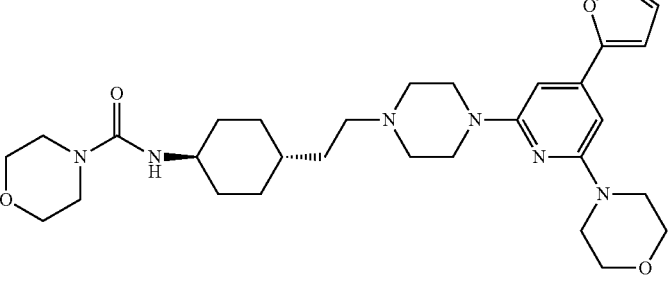 |
| VI-1 | 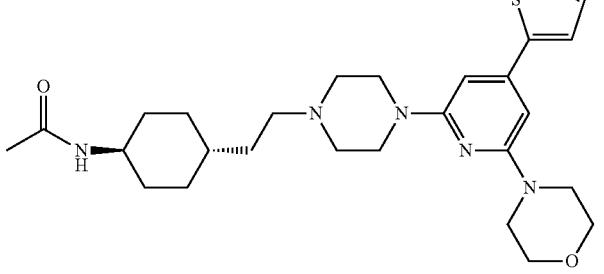 |

| No. | Structure |
|---|---|
| VI-2 | 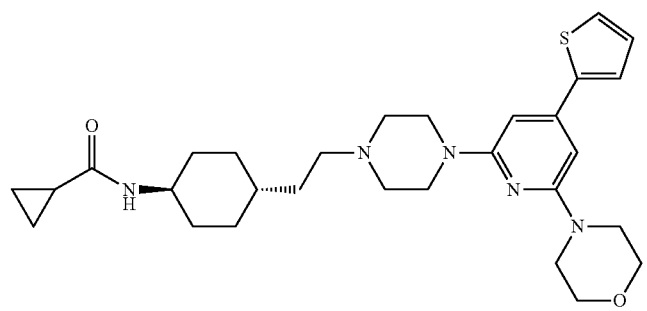 [SMILES: O=C(N[C@H]1CC[C@H](CCN2CCN(c3cc(-c4cccs4)cc(N4CCOCC4)n3)CC2)CC1)C1CC1] |
| VI-3 | 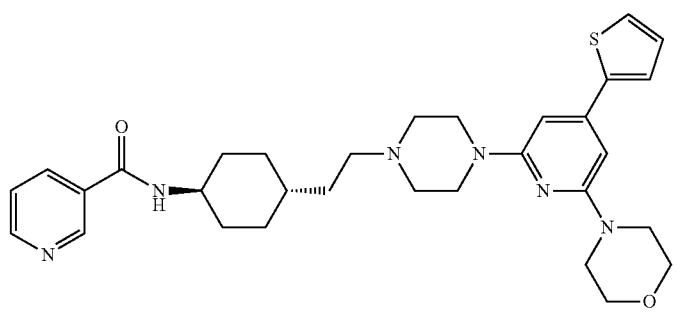 [SMILES: O=C(N[C@H]1CC[C@H](CCN2CCN(c3cc(-c4cccs4)cc(N4CCOCC4)n3)CC2)CC1)c1cccnc1] |
| VI-4 | 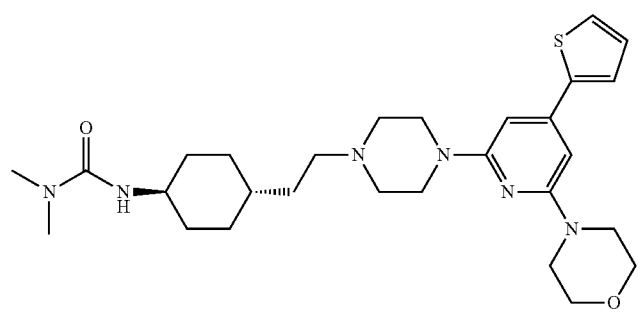 |
| VI-5 | 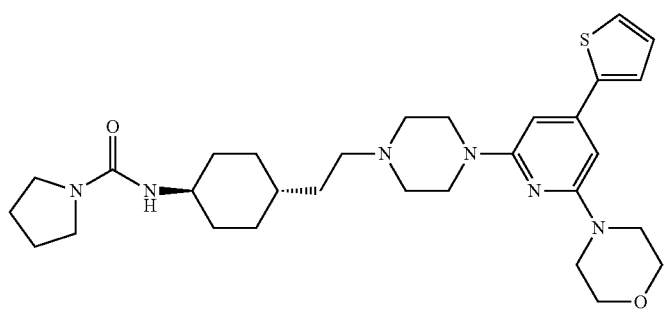 [SMILES: O=C(N[C@H]1CC[C@H](CCN2CCN(c3cc(-c4cccs4)cc(N4CCOCC4)n3)CC2)CC1)N1CCCC1] |
| VII-1 | 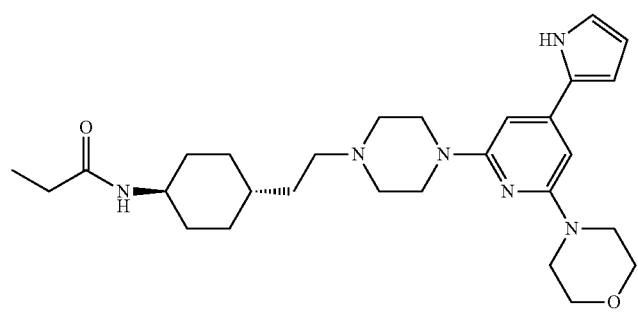 [SMILES: CCC(=O)N[C@H]1CC[C@H](CCN2CCN(c3cc(-c4ccc[nH]4)cc(N4CCOCC4)n3)CC2)CC1] |

| No. | Structure |
|---|---|
| VII-2 | 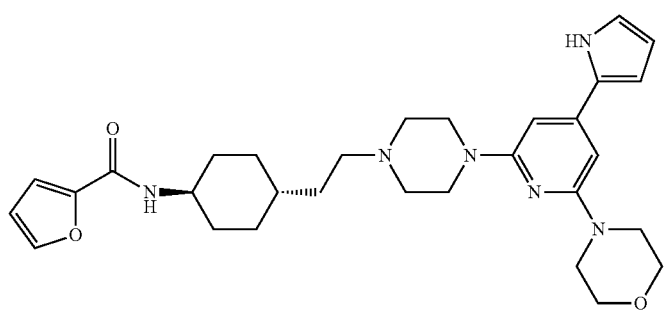 [SMILES: O=C(N[C@H]1CC[C@H](CCN2CCN(c3cc(-c4ccc[nH]4)cc(N4CCOCC4)n3)CC2)CC1)c1ccco1] |
| VII-3 | 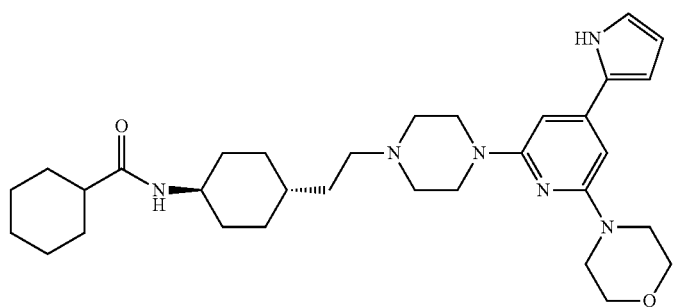 [SMILES: O=C(N[C@H]1CC[C@H](CCN2CCN(c3cc(-c4ccc[nH]4)cc(N4CCOCC4)n3)CC2)CC1)C1CCCCC1] |
| VII-4 | 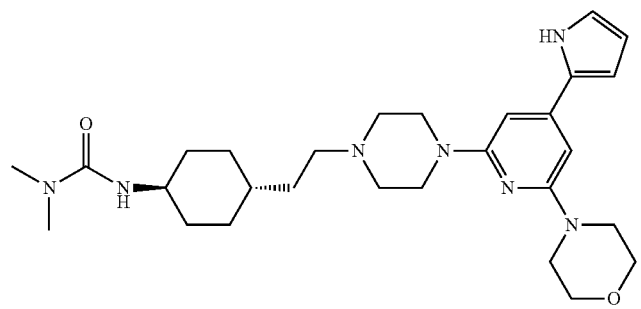 |
| VII-5 | 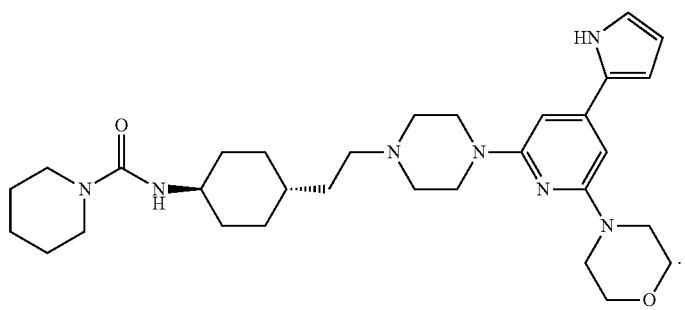 [SMILES: O=C(N[C@H]1CC[C@H](CCN2CCN(c3cc(-c4ccc[nH]4)cc(N4CCOCC4)n3)CC2)CC1)N1CCCCC1] |

9. A preparation method of the pyridinyl morpholine compound represented by formula I according to claim 1, wherein, comprising conducting an amidation reaction as shown below with a compound represented by formula 6 and substance Y to obtain the pyridinyl morpholine compound represented by formula I; the substance Y is a compound represented by formula A or formula B;

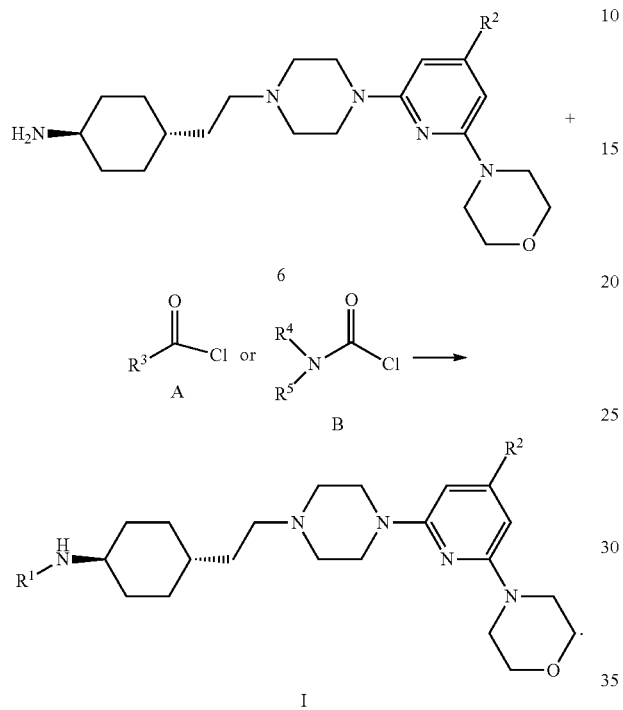

10. A pharmaceutical composition, wherein, comprising substance X and pharmaceutical excipients; the substance X is the pyridinyl morpholine compound represented by formula I, the pharmaceutically acceptable salt thereof, or the hydrate of the pharmaceutically acceptable salt thereof according to claim 1.

11. A method for treating or antagonizing schizophrenia in a subject in need thereof, comprising administering an effective amount of substance X to the subject, wherein, the substance X is the pyridinyl morpholine compound represented by formula I, the pharmaceutically acceptable salt thereof, or the hydrate of the pharmaceutically acceptable salt thereof according to claim 1.

12. The pyridinyl morpholine compound represented by formula I, the pharmaceutically acceptable salt thereof, or the hydrate of the pharmaceutically acceptable salt thereof according to claim 4, wherein,
when $R^3$ is $C_1$-$C_3$ alkyl, the $C_1$-$C_3$ alkyl is methyl, ethyl, n-propyl, or isopropyl;
when $R^3$ is $C_1$-$C_3$ alkyl substituted by one $C_1$-$C_3$ alkoxy, the $C_1$-$C_3$ alkoxy is methoxy;
when $R^3$ is $C_1$-$C_3$ alkyl substituted by one $C_1$-$C_3$ alkoxy, the $C_1$-$C_3$ alkyl is methyl;
when $R^3$ is $C_1$-$C_3$ alkoxy, the $C_1$-$C_3$ alkoxy is ethoxy;
when $R^3$ is $C_3$-$C_6$ cycloalkyl, the $C_3$-$C_6$ cycloalkyl is cyclopropyl or cyclohexyl;
when $R^3$ is "5- to 6-membered heteroaryl with 1 to 2 heteroatoms selected from one or more of N, O and S", the "5- to 6-membered heteroaryl with 1 to 2 heteroatoms selected from one or more of N, O and S" is "5- to 6-membered heteroaryl with 1 heteroatom selected from N, O and S":
when $R^3$ is "5- to 6-membered heterocycloalkyl with one heteroatom of N, and 0 or 1 heteroatom selected from N, O and S", the "5- to 6-membered heterocycloalkyl with one heteroatom of N, and 0 or 1 heteroatom selected from N, O and S" is

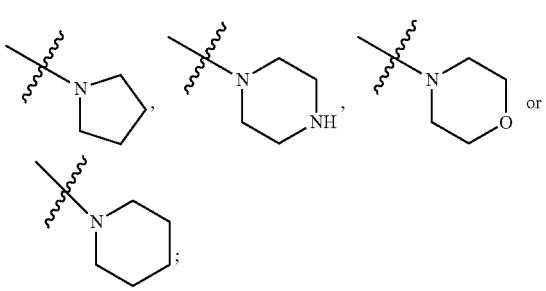

when $R^3$ is "5- to 6-membered heterocycloalkyl with one heteroatom of N, and 0 or 1 heteroatom selected from N, O and S substituted by one $C_1$-$C_3$ alkyl", the $C_1$-$C_3$ alkyl is methyl, ethyl, n-propyl, or isopropyl;
when $R^3$ is "5- to 6-membered heterocycloalkyl with one heteroatom of N, and 0 or 1 heteroatom selected from N, O and S substituted by one $C_1$-$C_3$ alkyl", the "5- to 6-membered heterocycloalkyl with one heteroatom of N, and 0 or 1 heteroatom selected from N, O and S" is

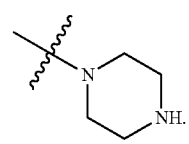 [SMILES: *N1CCNCC1]

13. The pyridinyl morpholine compound represented by formula I, the pharmaceutically acceptable salt thereof, or the hydrate of the pharmaceutically acceptable salt thereof according to claim 4, wherein,
when $R^4$ is $C_1$-$C_3$ alkyl, the $C_1$-$C_3$ alkyl is methyl, ethyl, n-propyl, or isopropyl;
or, when $R^5$ is $C_1$-$C_3$ alkyl, the $C_1$-$C_3$ alkyl is methyl, ethyl, n-propyl, or isopropyl;
or, when $R^2$ is "5- to 6-membered heteroaryl with 1 to 2 heteroatoms selected from one or more of N, O and S", the "5- to 6-membered heteroaryl with 1 to 2 heteroatoms selected from one or more of N, O and S" is "5- to 6-membered heteroaryl with 1 heteroatom selected from N, O and S".

14. The pyridinyl morpholine compound represented by formula I, the pharmaceutically acceptable salt thereof, or the hydrate of the pharmaceutically acceptable salt thereof according to claim 4, wherein,
when $R^{2-1}$ is $C_1$-$C_3$ alkoxy, the $C_1$-$C_3$ alkoxy is methoxy, ethoxy, propoxy or isopropoxy;
or, when $R^{2-1}$ is halogen, the halogen is fluorine, chlorine, bromine or iodine.

15. The pyridinyl morpholine compound represented by formula I, the pharmaceutically acceptable salt thereof, or the hydrate of the pharmaceutically acceptable salt thereof according to claim 5, wherein, when $R^{2-1}$ is $C_1$-$C_3$ alkoxy, the $C_1$-$C_3$ alkoxy is methoxy;

or, when $R^2$ is "5- to 6-membered heteroaryl with 1 heteroatom selected from N, O and S", the "5- to 6-membered heteroaryl with 1 heteroatom selected from N, O and S" is furanyl, thienyl, pyrrolyl or pyridyl.

16. The pyridinyl morpholine compound represented by formula I, the pharmaceutically acceptable salt thereof, or the hydrate of the pharmaceutically acceptable salt thereof according to claim 1, wherein, the pharmaceutically acceptable salt of the pyridinyl morpholine compound represented by formula I is any one of the following compounds:

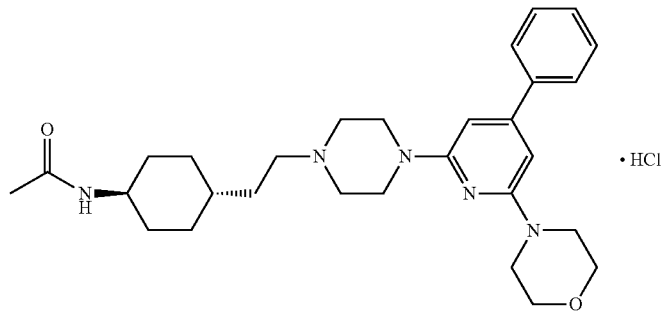

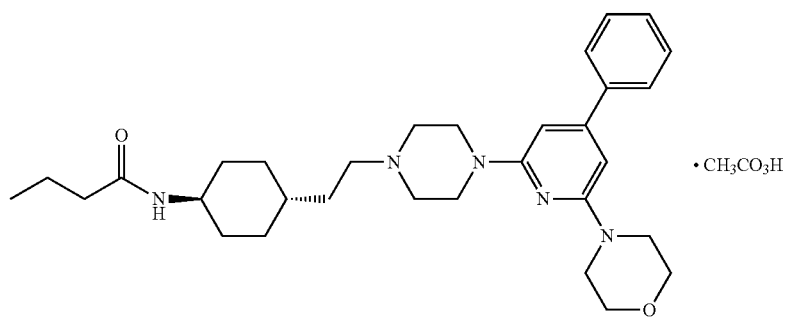

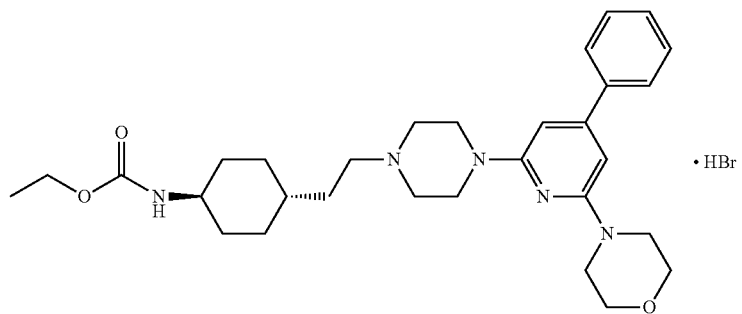

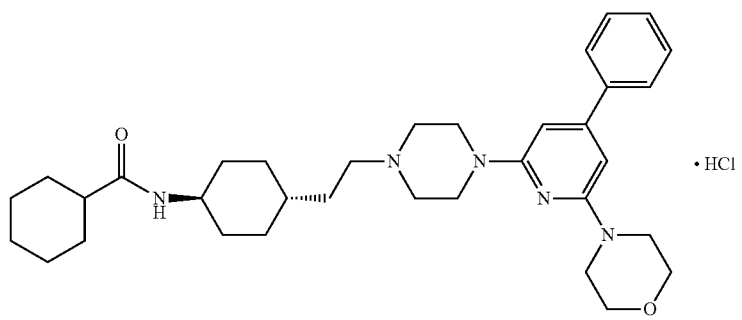

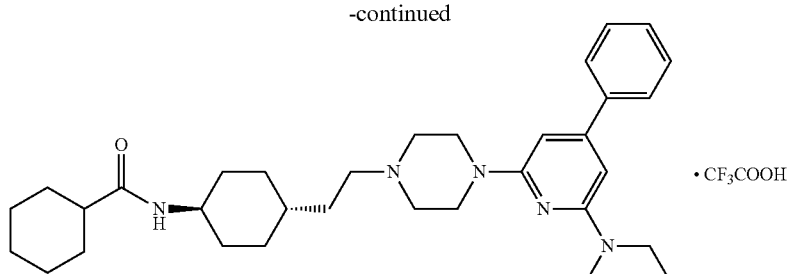

· CF₃COOH

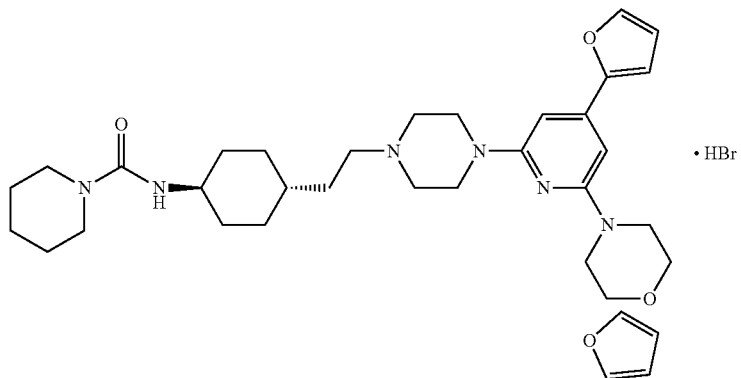

· HBr

· 1/2H₂CO₄

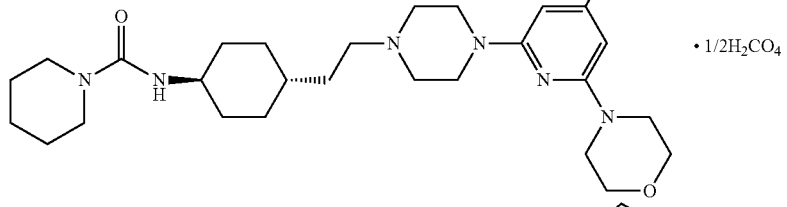

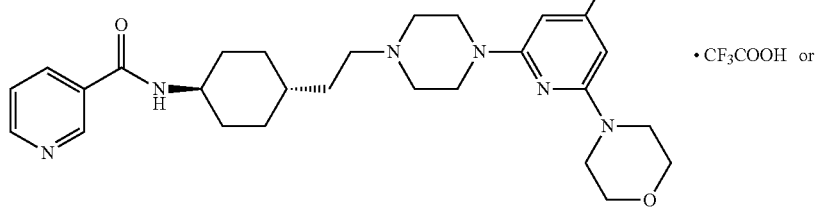

· CF₃COOH   or

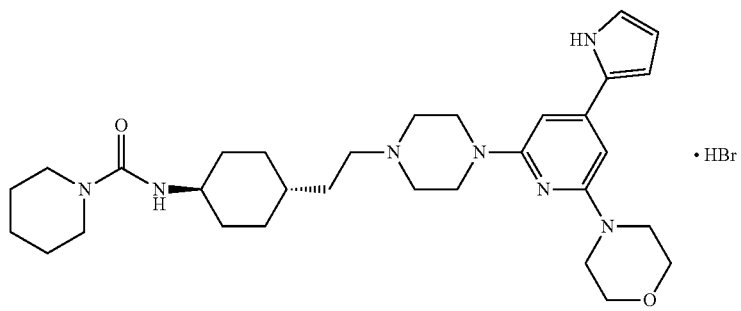

· HBr

17. The pyridinyl morpholine compound represented by formula I, the pharmaceutically acceptable salt thereof, or the hydrate of the pharmaceutically acceptable salt thereof according to claim 1, wherein, the hydrate of the pharmaceutically acceptable salt of the pyridinyl morpholine compound represented by formula I is the following compound:

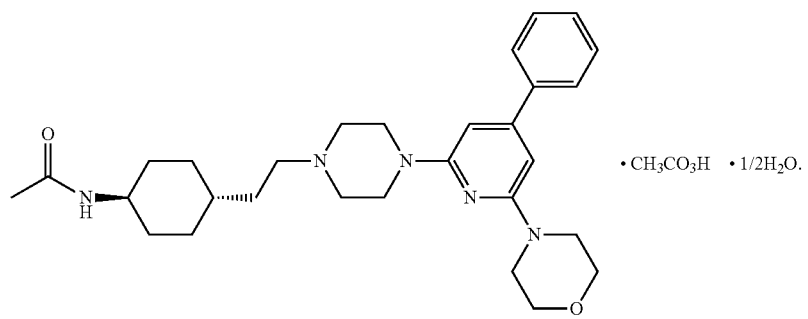
15
18. The method according to claim 11, wherein, the antagonizing refers to antagonizing one or more than one of $D_2$, $D_3$ and $5\text{-}HT_{2A}$.
* * * * *

UNITED STATES PATENT AND TRADEMARK OFFICE
CERTIFICATE OF CORRECTION

PATENT NO. : 12,410,136 B2
APPLICATION NO. : 18/007840
DATED : September 9, 2025
INVENTOR(S) : Jianqi Li et al.

Page 1 of 1

It is certified that error appears in the above-identified patent and that said Letters Patent is hereby corrected as shown below:

In the Claims

Claim 16, Column 84, please delete the second formula and replace with:

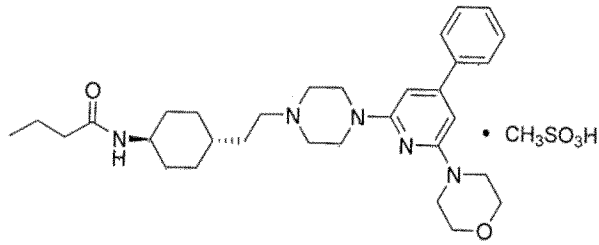

Claim 16, Column 86, please delete the third formula and replace with:

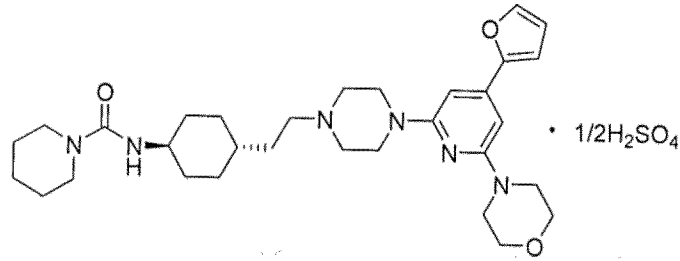

Claim 17, Column 87, please delete the formula and replace with:

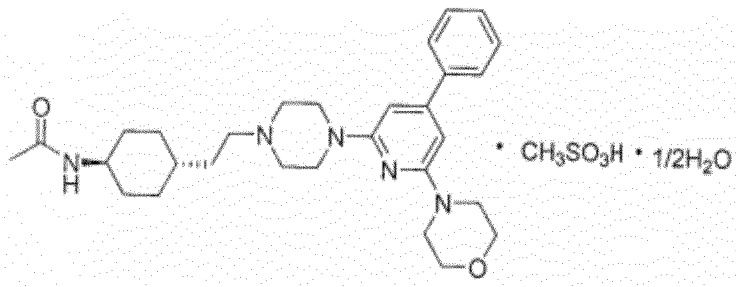

Signed and Sealed this
Twenty-fifth Day of November, 2025

John A. Squires
*Director of the United States Patent and Trademark Office*